US008404642B2

(12) United States Patent
Jørgensen et al.

(10) Patent No.: US 8,404,642 B2
(45) Date of Patent: Mar. 26, 2013

(54) TREATMENT OF ALLODYNIA, HYPERALGESIA, SPONTANEOUS PAIN AND PHANTOM PAIN

(75) Inventors: Jesper Roland Jørgensen, Frederiksberg (DK); Lars Ulrik Wahlberg, Tiverton, RI (US); Teit E. Johansen, Hørsholm (DK)

(73) Assignee: NsGene A/S, Ballerup (DK)

( * ) Notice: Subject to any disclaimer, the term of this patent is extended or adjusted under 35 U.S.C. 154(b) by 0 days.

(21) Appl. No.: 13/251,630

(22) Filed: Oct. 3, 2011

(65) Prior Publication Data

US 2012/0108518 A1 May 3, 2012

Related U.S. Application Data

(60) Provisional application No. 61/390,791, filed on Oct. 7, 2010.

(30) Foreign Application Priority Data

Oct. 1, 2010 (DK) .................................. 2010 70423
Sep. 30, 2011 (WO) ................ PCT/DK2011/050369

(51) Int. Cl.
*A61K 38/00* (2006.01)
*A61K 38/16* (2006.01)
*A61K 38/17* (2006.01)
*A61K 38/18* (2006.01)
*C07K 14/475* (2006.01)

(52) U.S. Cl. ...... 514/18.3; 514/7.6; 514/17.7; 514/21.2; 530/350

(58) Field of Classification Search .................. None
See application file for complete search history.

(56) References Cited

FOREIGN PATENT DOCUMENTS

| WO | WO 93/22437 | 11/1993 |
|---|---|---|
| WO | WO 95/05452 | 2/1995 |
| WO | WO 97/44065 | 11/1997 |
| WO | WO 01/25427 | 4/2001 |
| WO | WO 01/39786 | 6/2001 |
| WO | WO 01/54474 | 8/2001 |
| WO | WO 01/55301 | 8/2001 |
| WO | WO 01/55440 | 8/2001 |
| WO | WO 01/57190 | 8/2001 |
| WO | WO 01/83510 | 11/2001 |
| WO | WO 02/078730 | 10/2002 |
| WO | WO 03/066877 | 8/2003 |
| WO | WO 2004/035732 | 4/2004 |
| WO | WO 2004/079014 | 9/2004 |
| WO | WO 2005/095460 | 10/2005 |
| WO | WO 2006/110593 | 10/2006 |
| WO | WO 2007/100808 | 9/2007 |
| WO | WO 2010/009732 | 1/2010 |
| WO | PCT/DK2011/050369 | 9/2011 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Skolnick et al. (2000). From genes to protein structure and function: novel applications of computational approaches in the genomic era, Trends in Biotech. 18(1):34-39.*
International Search Report and Written Opinion of the International Searching Authority for International Application No. PCT/DK2011/050369, dated Feb. 28, 2012.
Claims from International Application No. PCT/DK2011/050369, published Apr. 5, 2012.
Tanaka et al., "Increased expression of the neurotrophic growth factor meteorin-like protein in lesional skin of individuals with familial primary localized cutaneous amyloidosis," *Journal of Investigative Dermatology* 129:54, 2009 (Abstract Only).
Alexi et al.; Neuroprotective strategies for basal ganglia degeneration: Parkinson's and Huntington's diseases; Progress in Neurobiology 60 (2000) 409-470.
Anderson et al.; Ciliary neurotrophic factor protects striatal output neurons in an animal model of Huntington desease; Proc. Natl. Acad. Sci. USA, vol. 93, pp. 7346-7351, Jul. 1996, Neurobiology.
Clark K. Colton; Engineering challenges in cell-encapsulation technology; Elsevier Publications, Cambridge, GB LNKD-DOI:10.1016/0167-7799(96) 10021-4, vol. 14, No. 5, May 1, 1996, pp. 156-162 Trends in Biotechnology.
EP 09156744.6, Communication 94(3) from EPO, Aug. 12, 2010.
Fransen et al: "Molecular cloning of a novel macrophage-drived cytokine (SMAF-1) and its immunomodulating capacities". Cytokine, vol. 11, No. 11, Nov. 1999, p. 975 abstract 254, Seventh Annual Conference of the iNternational CytokineSociety; Hilton Head, South Carolina USA; Dec. 5-9, 1999 ISSN: 1043-4666.
Fransson et al, Karolinska Institutet, NsGene A/S, Poster: A Novel neurotrophic factor supports spiral ganglion neuron survival and their electrical responsiveness in vivo. Presented Mar. 2, 2010 at the ANS/AuPS 2010 Joint Meeting in Sydney by A. Fransson.
GenBank, ABA06589, Jan. 10, 2002.
GenBank, ABA06759, Jan. 10, 2002.
GenBank, ABB10367, Jan. 10, 2002.
GenBank, ABB10537, Jan. 10, 2002.
GenBank, ABB57447, Mar. 15, 2002.
GenBank, ADP29324, Aug. 12, 2004.
GenBank, BG806341, Dec. 21, 2001.
GenBank, CAB56188, Sep. 17, 1999.
GenBank, NP_076947, Feb. 27, 2001.
GenBank, AAH00662, Nov. 29, 2000.
GenBank, AAH37181, Sep. 23, 2002.
GenBank, AAH88383, Dec. 22, 2004.
GenBank, AAK61247, Jun. 8, 2001.
GenBank, AAM78739, Nov. 6, 2001.
GenBank, AAM79723, Nov. 6, 2001.
Gong W Y et al: "Metrnl: A new secreted protein inhibit differentiation of MG-63" Journal of Bone and Mineral Research, vol. 22, No. Suppl. 1, Sep. 2007, p. S142.

(Continued)

*Primary Examiner* — Christine J Saoud
*Assistant Examiner* — Jon M Lockard
(74) *Attorney, Agent, or Firm* — Kristina Bieker-Brady; Clark & Elbing LLP

(57) ABSTRACT

The present invention relates to the use of Meteorin for the treatment of allodynia, hyperalgesia, spontaneous pain and phantom pain. In a preferred embodiment the disorder to be treated is allodynia, and hyperalgesia, more preferably allodynia including thermal and tactile allodynia.

39 Claims, 14 Drawing Sheets

OTHER PUBLICATIONS

Grønborg et al. "Identification of secreted neurotrophic factors using bioinformatics combined with expression analysis", program No. 825.2, abstract viewer/itinerary planner, Washington, DC: Society for Neuroscience (2005).

Handbook of psychology, Michela Gallagher, Randy J. Nelson, Irving B. Weiner. (2003) p. 391.

Heijne, von G. "A new method for predicting signal sequence cleavage sites", Nucleic acids research, Oxford University Press, Surrey, GB, vol. 14., No. 11, Jan. 1, 1986, pp. 4683-4690.

Jackowski, :Neural Injury Repair: Hope for the Future as Barriers to Effective CNS Regeneration Become Clearer, British Journal of Neurosurgery 9:303-317 (1995).

Jørgensen et al, Poster 323.8, presented at SfN meeting in 2008: Meteorin and Meteorin-like, initial characterization of a novel growth factor family.

Jørgensen et al, Poster: Meteorin protects striatal neurons and improves behavior in a rat model of huntington's Disease. Published Jan. 28, 2010.

Jørgensen et al., "Characterization of Meteorin—An Evolutionary Conserved Neurotrophic Factor", Humana Press 2009; J Mol Neurosci DOI 10:1O07/s12031-009-9189-4.

Jørgensen et al.: Lentiviral delivery of Meteroin protects striatal neurons against excitotoxicity and reverses motor deficits in the quinolinic acid rat model. Neurobiology of Disease, YNBDI-02246; No. of pp. 9; 4C:4. 2010.

Mizuno et al.: Brain-derived neurotrophic factor promotes differentiation of striatal GABAergic neurons. Abstract ; Dev. Biol. Sep. 1994; 165(1):243-256.

Mu et al., "Gene expression in the developing mouse retina by EST sequencing and microarray analysis", Nucl.Acids Res., 29(24):4983-4993 (2001.

Navarro-Galve et al., "HNSG33 effects on survivial and differentiation of human neural stem cell-derived neuronal and glial progeny", program No. 248.14, abstract viewer/itineary planner, Washington, DC: Society for Neuroscience (2005).

Navarro-Galve et al; "hNsG33 effects on survival and differentiation of human neural stem cells". Conference presentation Nov. 13, 2005.

Nielsen et al. "A neural network method for identification of prokaryotic and eukaryotic signal peptides and prediction of their cleavage sites", International journal of Neural Systems , Singapore, vol. 8, No. 5-6, Oct. 1, 1997, pp. 581-599.

Nishino et al., "Meterorin: a secreted protein that regulates glial cell differentitaion and promotes axonal extension", EMBO J., 23(9):1998-2008 (2004).

Ramialison et al, Genome Biology 2008, 9: R145 Published Oct. 1, 2008: Rapid identification of PAX2/5/8 direct downstream targets in the otic vesicle by combinatorial use of bioinformatics tools.

Todoroki et al., "Ropivacaine Inhibits Neurite Outgrowth in PC-12 Cells", Department of Anesthesiology, Nagasaki University School of Medicine, Japan, Anesth Analg 2004;99:828-32.

Ventimiglia et al: "The neurotrophins BDNF, NT-3 and NT-4/5 promote survival and morphological and biochemical differentiation of striatal neurons in vitro". Eur. J Neurosci. Feb. 1, 1995;7(2)213-22 (Abstract).

Rudinger, "Characteristics of teh Amino Acids as Components of a Peptide Hormone Sequence" in "Peptide Hormones" (Ed. J.A. Parsons), University Park Press, Baltimore, pp. 1-7 (1976).

* cited by examiner

Figure 6a

```
Mouse    --MLVATLLCALCCGLLAASAHAGYSEDRCSWRGSGLTQEPGSVGQLTLDCTEGAIEWLY  58
Rat      --MLVAALLCALCCGLLAASARAGYSEDRCSWRGSGLTQEPGSVGQLTLDCTEGAIEWLY  58
Human    MGFPAAALLCALCCGLLAPAARAGYSEERCSWRGSGLTQEPGSVGQLALACAEGAVEWLY  60
           .*:*:*********..*:*****:********************:* *:***:****

Mouse    PAGALRLTLGGPDPGTRPSIVCLRPERPFAGAQVFAERMTGNLELLLAEGPDLAGGRCMR  118
Rat      PAGALRLTLGGSDPGTRPSIVCLRPTRPFAGAQVFAERMAGNLELLLAEGQGLAGGRCMR  118
Human    PAGALRLTLGGPDPRARPGIACLRPVRPFAGAQVFAERAGGALELLLAEGPGPAGGRCVR  120
         ***********.**.:**.*.****  **********    .*********  :*****:*

Mouse    WGPRERRALFLQATPHRDISRRVAAFRFELHEDQRAEMSPQAQGLGVDGACRPCSDAELL  178
Rat      WGPRERRALFLQATPHRDISRRVAAFQFELHEDQRAEMSPQAQGFGVDGACRPCSDAELL  178
Human    WGPRERRALFLQATPHQDISRRVAAFRFELREDGRPELPPQAHGLGVDGACRPCSDAELL  180
         ****************:*********:***:**  *.:.***:*:*************

Mouse    LAACTSDFVIHGTIHGVAHDTELQESVITVVVARVIRQTLPLFKEGSSEGQGRASIRTLL  238
Rat      LTACTSDFVIHGTIHGVVHDMELQESVITVVATRVIRQTLPLFQEGSSEGRGQASVRTLL  238
Human    LAACTSDFVIHGIIHGVTHDVELQESVITVVAARVLRQTPPLFQAGRSGDQGLTSIRTPL  240
         *:**********  ****.** ********* :**:***  ***: .   ::*:** *

Mouse    RCGVRPGPGSFLFMGWSRFGEAWLGCAPRFQEFSRVYSAALTTHLNPCEMALD  291
Rat      RCGVRPGPGSFLFMGWSRFGEAWLGCAPRFQEFSRVYSAALAAHLNPCEVALD  291
Human    RCGVHPGPGTFLFMGWSRFGEARLGCAPRFQEFRRAYEAARAAHLHPCEVALH  293
         ****:****:*********** *********.:.**  ::**:***:**.
```

Figure 6b

```
Mouse    GYSEDRCSWRGSGLTQEPGSVGQLTLDCTEGAIEWLYPAGALRLTLGGPDPGTRPSIVCL  60
Rat      GYSEDRCSWRGSGLTQEPGSVGQLTLDCTEGAIEWLYPAGALRLTLGGSDPGTRPSIVCL  60
Human    GYSEERCSWRGSGLTQEPGSVGQLALACAEGAVEWLYPAGALRLTLGGPDPRARPGIACL  60
         ****:*******************:** *:**:***************.**.:**.*.*

Mouse    RPERPFAGAQVFAERMTGNLELLLAEGPDLAGGRCMRWGPRERRALFLQATPHRDISRRV  120
Rat      RPTRPFAGAQVFAERMAGNLELLLAEGQGLAGGRCMRWGPRERRALFLQATPHRDISRRV  120
Human    RPVRPFAGAQVFAERAGGALELLLAEGPGPAGGRCVRWGPRERRALFLQATPHQDISRRV  120
         ** ************   .*******   :*****:****************:******

Mouse    AAFRFELHEDQRAEMSPQAQGLGVDGACRPCSDAELLLAACTSDFVIHGTIHGVAHDTEL  180
Rat      AAFQFELHEDQRAEMSPQAQGFGVDGACRPCSDAELLLTACTSDFVIHGTIHGVVHDMEL  180
Human    AAFRFELREDGRPELPPQAHGLGVDGACRPCSDAELLLAACTSDFVIHGIIHGVTHDVEL  180
         ***:***:**.* *:.***:*:***************:**********  ****.** **

Mouse    QESVITVVVARVIRQTLPLFKEGSSEGQGRASIRTLLRCGVRPGPGSFLFMGWSRFGEAW  240
Rat      QESVITVVATRVIRQTLPLFQEGSSEGRGQASVRTLLRCGVRPGPGSFLFMGWSRFGEAW  240
Human    QESVITVVAARVLRQTPPLFQAGRSGDQGLTSIRTPLRCGVHPGPGTFLFMGWSRFGEAR  240
         *********:**:*** ***: .  *: * .:*:** ****:****:*************

Mouse    LGCAPRFQEFSRVYSAALTTHLNPCEMALD  270
Rat      LGCAPRFQEFSRVYSAALAAHLNPCEVALD  270
Human    LGCAPRFQEFRRAYEAARAAHLHPCEVALH  270
         **********.:.**  ::**:***:**.
```

Figure 6c

| | |
|---|---|
| Consensus | GYSEXRCSWRGSGLTQEPGSVGQLXLXCXEGAXEWLYPAGALRLTLGGXDPXXRPXIXCL 60 |
| Consensus | RPXRPFAGAQVFAERXXGXLELLLAEGXXXAGGRCXRWGPRERRALFLQATPHXDISRRV 120 |
| Consensus | AAFXFELXEDXRXEXXPQAXGXGVDGACRPCSDAELLLXACTSDFVIHGXIHGVXHDXEL 180 |
| Consensus | QESVITVVXXRVXRQTXPLFXXGXSXXXGXXSXRTXLRCGVXPGPGXFLFMGWSRFGEAX 240 |
| Consensus | LGCAPRFQEFXRXYXAAXXXHLXPCEXALX 270 |

TREATMENT OF ALLODYNIA, HYPERALGESIA, SPONTANEOUS PAIN AND PHANTOM PAIN

CROSS-REFERENCE TO RELATED APPLICATIONS

The present application claims the benefit of U.S. Provisional Application No. 61/390,791 filed on 7 Oct., 2010, Denmark Application No. PA 2010 70423 filed on 1 Oct. 2010, and International Patent Application No. PCT/DK2011/050369 filed on 30 Sep. 2011, the contents of each are hereby incorporated by reference.

All patent and non-patent references cited in the application, or in the present application, are also hereby incorporated by reference in their entirety.

FIELD OF INVENTION

The present invention relates to the use of Meteorin for the treatment of allodynia, hyperalgesia, spontaneous pain and phantom pain. In a preferred embodiment the disorder to be treated is allodynia, and hyperalgesia, more preferably allodynia including thermal and tactile allodynia. In another preferred embodiment the disorder is thermal hyperalgesia.

BACKGROUND OF INVENTION

Many therapies have been explored for the treatment of allodynia, hyperalgesia, spontaneous pain and phantom pain with varying degree of success, including non-steroidal anti-inflammatory drugs (NSAIDs), opioids, anticonvulsants, anti-arrhythmics, tricyclic antidepressants and topical agents. Alternative approaches include anaesthetic blocks, epidural administration of steroids and neurosurgical lesions. However, all of the present therapies have modest efficacy in most patients and are palliative rather than curative and their side effects represent significant limitations.

Hence, there is a high unmet need for therapies that treat allodynia, hyperalgesia, spontaneous pain and phantom pain effectively, preferably with only minor side effects not affecting the general health of the patients.

SUMMARY OF INVENTION

The present invention provides methods for treatment of allodynia, hyperalgesia, spontaneous pain and phantom pain. The methods use Meteorin protein, nucleotide sequences encoding Meteorin, expression vectors containing the nucleotide sequence encoding Meteorin, cell lines transformed/transfected with the expression vector encoding Meteorin, or biocompatible capsule delivering secreted Meteorin.

Thus, in a first aspect the present invention relates to an isolated polypeptide for use in a method of treatment of allodynia, hyperalgesia, spontaneous pain and/or phantom pain, said polypeptide comprising an amino acid sequence selected from the group consisting of:
  i. The amino acid sequence of SEQ ID NO: 3;
  ii. A biologically active sequence variant of the amino acid sequence of SEQ ID NO:3, wherein the variant has at least 70% sequence identity to SEQ ID NO:3; and
  iii. A biologically active fragment of at least 50 contiguous amino acids of i) or ii) wherein the fragment is at least 70% identical to SEQ ID NO: 3.

The inventors have found that Meteorin is capable of alleviating allodynia in animal models of both thermal and mechanical allodynia and spontaneous pain (weight bearing deficit). Importantly the animals did not experience any weight loss or signs of toxicity over the duration of the experiment and no painful side effects were observed. The positive effects have been observed independently in several different models of allodynia and spontaneous pain and using both systemic (subcutaneous) and local (intrathecal) administration In a further aspect the invention relates to an isolated nucleic acid molecule for use in a method of treatment of allodynia, hyperalgesia, spontaneous pain and/or phantom pain, said nucleic acid molecule comprising a nucleic acid sequence encoding a polypeptide, said polypeptide comprising an amino acid sequence selected from the group consisting of:
  i. The amino acid sequence of SEQ ID NO: 3;
  ii. A biologically active sequence variant of the amino acid sequence of SEQ ID NO:3, wherein the variant has at least 70% sequence identity to SEQ ID NO:3; and
  iii. A biologically active fragment of at least 50 contiguous amino acids of i) or ii) wherein the fragment is at least 70% identical to SEQ ID NO:3.

In a further aspect the invention relates to an expression vector comprising a nucleic acid molecule of the invention for use in a method of treatment of allodynia, hyperalgesia, spontaneous pain and/or phantom pain.

In a still further aspect the invention relates to an isolated host cell comprising an expression vector according to the invention for use in a method of treatment of allodynia, hyperalgesia, spontaneous pain and/or phantom pain. In particular the invention relates to host cells useful for cell based therapy, either naked cell based therapy or encapsulated cell therapy for use in a method of treatment of allodynia, hyperalgesia, spontaneous pain and/or phantom pain.

In a further aspect the invention relates to an implantable biocompatible capsule for use in a method of treatment of allodynia, hyperalgesia, spontaneous pain and/or phantom pain by delivery of secreted biologically active Meteorin to a subject, said capsule comprising:
  i. A biocompatible outer membrane and an inner core,
  ii. Said inner core comprising cells according to the invention,
  iii. Said cells comprising a vector according to the invention.

In a further aspect the invention relates to a composition comprising:
  i. The isolated polypeptide according to the invention; or
  ii. The isolated nucleic acid according to the invention; or
  iii. The expression vector according to the invention; or
  iv. The cell line according to the invention; or
  v. An implantable biocompatible capsule according to the invention;
for use in a method of treatment of allodynia, hyperalgesia, spontaneous pain and/or phantom pain.

In a further aspect the invention relates to use of:
  i. The isolated polypeptide according to the invention;
  ii. The isolated nucleic acid according to the invention;
  iii. The expression vector according to the invention;
  iv. The cell line according to the invention; and
  v. An implantable biocompatible capsule according to the invention;
in the manufacture of a medicament for the treatment of allodynia, hyperalgesia, spontaneous pain and/or phantom pain.

In a further aspect the invention relates to a method of treatment of allodynia, hyperalgesia, spontaneous pain and/or phantom pain in a subject comprising administrating to said subject in need thereof therapeutically effective amounts of the isolated polypeptide according to the invention.

DESCRIPTION OF DRAWINGS

FIG. 6. CLUSTAL W (1.82) multiple sequence alignment of Meteorin.

FIG. 6a: alignment of Meteorin precursors from human (SEQ ID NO: 2), rat (SEQ ID NO: 8), and mouse (SEQ ID NO: 5).

FIG. 6b: alignment of mature Meteorin from human (SEQ ID NO: 3), rat (SEQ ID NO: 9), and mouse (SEQ ID NO: 6).

FIG. 6c: mature Meteorin, consensus sequence (SEQ ID NO: 11) generated from fully conserved residues in the human, mouse and rat sequences. X represents any of the 21 naturally occurring amino acid encoded by DNA.

DETAILED DESCRIPTION OF THE INVENTION

Definitions

Figure 1:
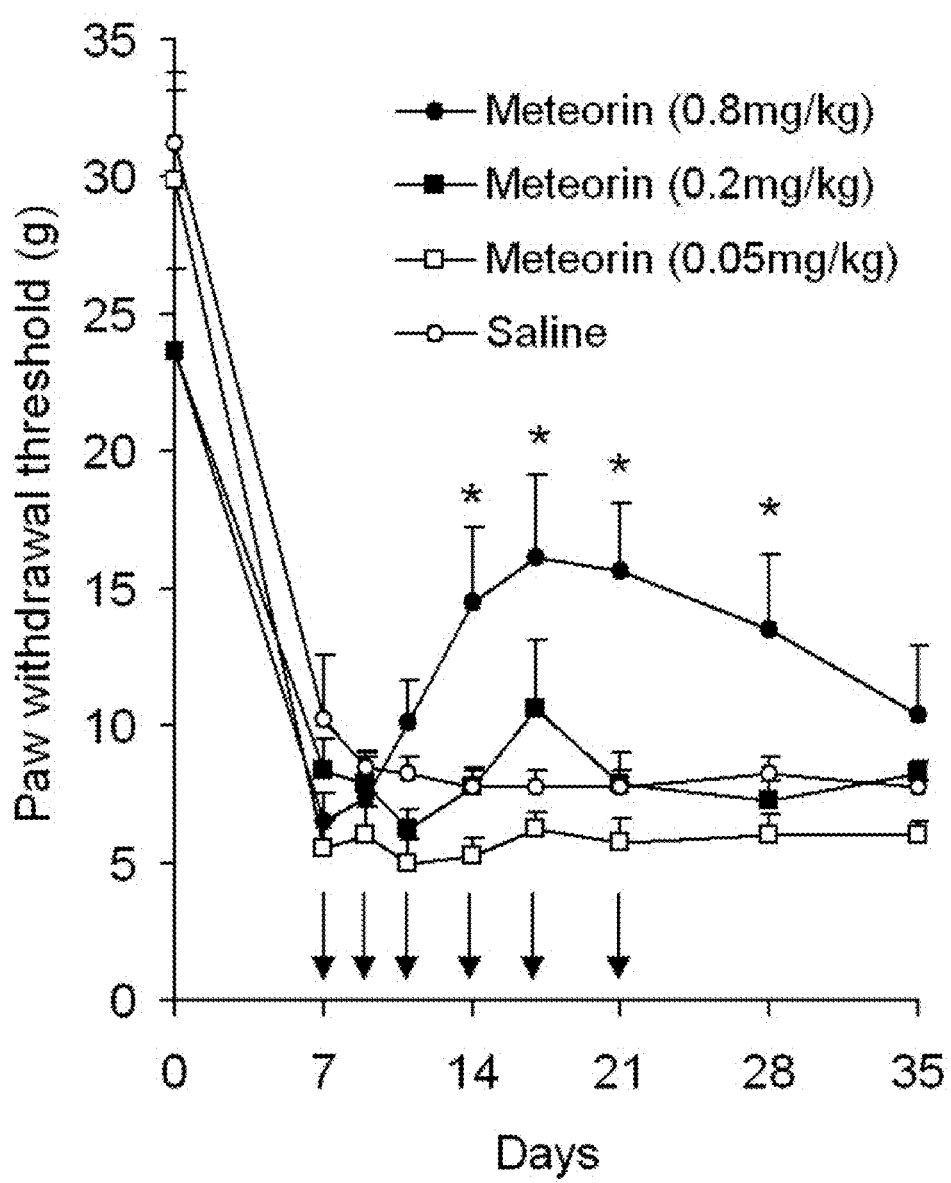
FIG. 1. Ipsilateral hind paw withdrawal threshold to mechanical stimulation with von Frey hairs following sciatic nerve injury. Note that Meteorin treatment dose-dependently alleviates mechanical allodynia. Arrows indicate treatment time points. The data are shown as mean±SEM and scoring was done blinded. *$p<0.05$.

As used herein "a biocompatible capsule" means that the capsule, upon implantation in a host mammal, does not elicit a detrimental host response sufficient to result in the rejection of the capsule or to render it inoperable, for example through degradation.

As used herein, a "coding sequence" is a polynucleotide sequence which is transcribed and translated into a polypeptide.

As used herein, the term "Control sequence" refers to polynucleotide sequences which are necessary to effect the expression of coding and non-coding sequences to which they are ligated. Control sequences generally include promoter, ribosomal binding site, and transcription termination sequence. In addition, "control sequences" refers to sequences which control the processing of the peptide encoded within the coding sequence; these can include, but are not limited to sequences controlling secretion, protease cleavage, and glycosylation of the peptide. The term "control sequences" is intended to include, at a minimum, components whose presence can influence expression, and can also include additional components whose presence is advantageous, for example, leader sequences and fusion partner sequences.

"Down regulation" of a promoter means the reduction in the expression of the product of transgene to a level, which may lead to a lack of significant biological activity of the transgene product after in vivo implantation. As used herein "a promoter not subject to down regulation" means a promoter, which, after in vivo implantation in a mammalian host, drives or continues to drive the expression of transgene at a level which is biologically active.

As used herein, the term "expression vectors" refers to vectors that are capable of directing the expression of genes to which they are operatively-linked. In general, expression vectors of utility in recombinant DNA techniques are often in the form of plasmids.

As used herein, the terms "genetic modification" and "genetic engineering" refer to the stable or transient alteration of the genotype of a cell by intentional introduction of exogenous DNA. DNA may be synthetic, or naturally derived, and may contain genes, portions of genes, or other useful DNA sequences. The term "genetic modification" is not meant to include naturally occurring alterations such as that which occurs through natural viral activity, natural genetic recombination, or the like.

As used herein "an immunoisolatory capsule" means that the capsule upon implantation into a mammalian host minimizes the deleterious effects of the host's immune system on the cells within its core.

As used herein "long-term, stable expression of a biologically active compound" means the continued production of a biologically active compound at a level sufficient to maintain its useful biological activity for periods greater than one month, preferably greater than three months and most preferably greater than six months.

By a "mammalian promoter" is intended a promoter capable of functioning in a mammalian cell.

Meteorin, as used herein, refers to polypeptides having the amino acid sequences of substantially purified Meteorin obtained from any species, particularly mammalian, including chimpanzee, bovine, ovine, porcine, murine, equine, and preferably human, from any source whether natural, synthetic, semi-synthetic, or recombinant. The term also refers to biologically active fragments of Meteorin obtained from any of these species, as well as to biologically active sequence variants of these and to proteins subject to posttranslational modifications.

Growth factor characteristics as used herein define sequence-related features similar to those of classical growth factors, which are secreted proteins acting on a target cell through a receptor to cause one or more of the following responses in the target cell: growth including proliferation, differentiation, survival, regeneration, migration, regain of function, improvement of function trophic support such as neurotrophic support.

As used herein, the term "operatively-linked" is intended to mean that the nucleotide sequence of interest is linked to the regulatory sequence(s) within a recombinant expression vector, in a manner that allows for expression of the nucleotide sequence (e.g., in an in vitro transcription/translation system or in a host cell when the vector is introduced into the host cell).

As used herein, the term "regulatory sequence" is intended to include promoters, enhancers and other expression control elements (e.g., polyadenylation signals).

"Sequence identity": A high level of sequence identity indicates likelihood that the first sequence is derived from the second sequence. Amino acid sequence identity requires identical amino acid sequences between two aligned sequences. Thus, a candidate sequence sharing 70% amino acid identity with a reference sequence, requires that, following alignment, 70% of the amino acids in the candidate sequence are identical to the corresponding amino acids in the reference sequence. Identity may be determined by aid of computer analysis, such as, without limitations, the ClustalW computer alignment program (Higgins D., Thompson J., Gibson T., Thompson J. D., Higgins D. G., Gibson T. J., 1994. CLUSTAL W: improving the sensitivity of progressive multiple sequence alignment through sequence weighting, position-specific gap penalties and weight matrix choice. Nucleic Acids Res. 22:4673-4680), and the default parameters suggested therein. The ClustalW software is available as a ClustalW WWW Service at the European Bioinformatics Institute. Using this program with its default settings, the mature (bioactive) part of a query and a reference polypeptide are aligned. The number of fully conserved residues are counted and divided by the length of the reference polypeptide.

The ClustalW algorithm may similarly be used to align nucleotide sequences. Sequence identities may be calculated in a similar way as indicated for amino acid sequences.

The term "subject" used herein is taken to mean any mammal to which Meteorin polypeptide or polynucleotide, therapeutic cells or biocompatible capsules may be administered. Subjects specifically intended for treatment with the method of the invention include humans, as well as nonhuman primates, sheep, horses, cattle, goats, pigs, dogs, cats, rabbits, guinea pigs, hamsters, gerbils, rats and mice, as well as the organs, tumors, and cells derived or originating from these hosts.

As used herein, the term "Transformation" refers to the insertion of an exogenous polynucleotide (i.e., a "transgene") into a host cell. The exogenous polynucleotide is integrated within the host genome.

"Treatment" can be performed in several different ways, including curative, ameliorating and as prophylaxis. Curative treatment generally aims at curing a clinical condition, such as a disease or an infection, which is already present in the treated individual. Ameliorating treatment generally means treating in order to improve, in an individual, an existing clinical condition. Prophylactic treatment generally aims at preventing a clinical condition or reducing the risk of contracting the condition or reducing the extent of the condition.

A treatment that can alter the underlying course of the disease. By impacting the actual disease process, "disease modification" therapy can delay, reverse or prevent progression of symptoms, or can change the long term course of the disease As used herein, the term "vector" refers to a nucleic acid molecule capable of transporting another nucleic acid to which it has been linked. One type of vector is a "plasmid", which refers to a circular double stranded DNA loop into which additional DNA segments can be ligated. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Allodynia

Allodynia, meaning "other pain", is a pain due to a stimulus which does not normally provoke pain and can be either thermal or mechanical/tactile. It is pain from a stimulus that does not normally lead to the sensation of pain, and may occur after injury to a site. Allodynia is different from hyperalgesia and spontaneous pain, which is described in the section "hyperalgesia" and "spontaneous pain" respectively.

There are different kinds or types of allodynia:
Mechanical allodynia (also known as tactile allodynia)
  Static mechanical allodynia—pain in response to light touch/pressure
  Dynamic mechanical allodynia—pain in response to brushing
Thermal (heat or cold) allodynia—pain from normally mild skin temperatures in the affected area Allodynia is a clinical feature of many painful conditions, such as neuropathies, complex regional pain syndrome, postherpetic neuralgia, fibromyalgia, and migraine. Allodynia may also be caused by some populations of stem cells used to treat nerve damage including spinal cord injury. In a preferred embodiment of the present invention the allodynia to be treated is cold allodynia. In another preferred embodiment of the present invention the allodynia to be treated is heat allodynia.

The cell types involved in nociception and mechanical sensation are the cells responsible for allodynia. In healthy individuals, nociceptors sense information about cell stress or damage and temperature at the skin and transmit it to the spinal cord. The cell bodies of these neurons lie in dorsal root ganglia, important structures located on both sides of the spinal cord. The axons then pass through the dorsal horn to make connections with secondary neurons. The secondary neurons cross over to the other (contralateral) side of the spinal cord and reach nuclei of the thalamus. From there, the information is carried through one or more neurons to the somatosensory cortex of the brain. Mechanoreceptors follow the same general pathway. However, they do not cross over at the level of the spinal cord, but at the lower medulla instead. In addition, they are grouped in tracts that are spatially distinct from the nociceptive tracts.

Despite this anatomical separation, mechanoreceptors can influence the output of nociceptors by making connections with the same interneurons, the activation of which can reduce or completely eliminate the sensation of pain. Another way to modulate the transmission of pain information is via descending fibers from the brain. These fibers act through different interneurons to block the transmission of information from the nociceptors to secondary neurons.

Both of these mechanisms for pain modulation have been implicated in the pathology of allodynia. Several studies suggest that injury to the spinal cord might lead to loss and re-organization of the nociceptors, mechanoreceptors and interneurons, leading to the transmission of pain information by mechanoreceptors. A different study reports the appearance of descending fibers at the injury site. All of these changes ultimately affect the circuitry inside the spinal cord, and the altered balance of signals probably leads to the intense sensation of pain associated with allodynia.

Different cell types have also been linked to allodynia. For example, there are reports that microglia in the thalamus might contribute to allodynia by changing the properties of the secondary nociceptors. The same effect is achieved in the spinal cord by the recruitment of immune system cells such as monocytes/macrophages and T lymphocytes.

As already mentioned, there are descending neurons that modulate the perception of pain. Many of these neurons originate in nuclei in the brainstem and pass through the periaqueductal gray (PAG) area of the midbrain.

The body possesses an additional mechanism to control pain: the release of endogenous opioids, especially at the level of the PAG. There are neurons that release enkephalins, endorphins, and dynorphins at the PAG, and in this way modulate its ability to modulate pain perception. Other neurons can release their endogenous opioids at the source of the pain, as well. If this occurs, the transmission of pain information from the nociceptors to the secondary neurons is blocked, and no pain is felt. Unfortunately, these endogenous mechanisms are often damaged and nonfunctional in people suffering from allodynia, so the application of pharmaceuticals is needed.

Numerous compounds alleviate the pain from allodynia. Some are specific for certain types of allodynia while others are general. They include non-steroidal anti-inflammatory drugs (NSAIDs), opioids, and compounds targeting different ion channels.

The present invention relates to the use of Meteorin for treatment of allodynia. Preferably the allodynia to be treated is thermal allodynia.

As documented by example 4 full reversal to normal sensory function was achieved in the majority of animals in the group receiving the highest dosage of Meteorin (1.8 mg/kg). It is thus conceivable that Meteorin can result in substantially full reversal of allodynia in at least a subset of the treated subjects. In a preferred embodiment, the treatment results in disease modification in at least a subset of the treated subjects.

Hyperalgesia

Hyperalgesia is an extreme response to a stimulus which is normally perceived as painful. The stimulus can be mechanical/tactile or thermal.

Hyperalgesia is similar to other sorts of pain associated with nerve damage such as allodynia, and consequently may respond to standard treatment for this condition as described in the section "allodynia".

In one embodiment the present invention relates to the use of Meteorin for treatment of hyperalgesia. Preferably the hyperalgesia to be treated is thermal hyperalgesia. In one embodiment of the present invention the hyperalgesia to be treated is cold hyperalgesia. In another embodiment of the present invention the hyperalgesia to be treated is heat hyperalgesia. As stated above substantially full reversal of normal sensory function was achieved in animals receiving the highest dosage of Meteorin. It is thus conceivable that Meteorin can result in full reversal of hyperalgesia in at least a subset of the treated subjects. In a preferred embodiment, the treatment results in disease modification in at least a subset of the treated subjects.

Spontaneous Pain

Spontaneous pain is characterized by being pain occurring without any trigger. The clinical symptoms of spontaneous pain include sensations of pins and needles, shooting, burning, stabbing and paroxysmal (electric shock-like) pain sometimes associated with dysesthesia and/or paresthesia. Dysesthesia is defined as an unpleasant, abnormal sense of touch, and it may be considered as a kind of pain occurring spontaneously. Paresthesia is defined as a sensation of tingling, pricking or numbness of a subjects skin with no apparent long-term physical effect. Spontaneous pain seems likely to be caused by spontaneous activity of neurons in the afferent pathway.

In one embodiment the present invention relates to the use of meteorin for treatment of spontaneous pain. It is thus conceivable that Meteorin can result in full reversal of spontaneous pain in at least a subset of the treated subjects. In a preferred embodiment, the treatment results in disease modification in at least a subset of the treated subjects.

Phantom Pain

Phantom pain sensations are described as perceptions that a subject experiences relating to a limb or an organ that is not physically part of the body. Phantom pain sensations are recorded most frequently following the amputation of an arm or a leg, but may also occur following the removal of a breast or an internal organ. The phantom pain sensation varies from individual to individual. Phantom pain can be experienced as sensations related to movement, touch, temperature, pressure and itchiness.

In one embodiment the present invention relates to the use of meteorin for treatment of phantom pain.

Causes of Allodynia, and Hyperalgesia

Allodynia, hyperalgesia and in general hypersensitivity can arise from a variety of disorders, some of which are listed below.

| Class | Sub-type of cause |
|---|---|
| Traumatic mechanical injury | Entrapment neuropathy |
| | Nerve transection |
| | Spinal cord injury |
| | Post-surgical pain |
| | Phantom limb pain |
| | Scar formation |
| | Sciatica |
| Metabolic or nutritional | Alcoholic neuropathy |
| | Pellagra |
| | Beriberi |
| | Burning foot syndrome |
| Viral | Post-herpetic neuralgia |
| | HIV/AIDS pain |
| Neurotoxicity | Vincristine |
| | Cisplatine |
| | Taxol |
| | Thallium |
| | Arsenic |
| | Radiation therapy |
| Disease (non-viral) | Diabetes |
| | Malignancies |
| | Multiple sclerosis |
| | Trigeminal neuralgia |
| | Guillain-Barre syndrome |
| | Fabry's disease |
| | Tangier disease |
| | Vasculitic/angiopathic |
| | Amyloid |
| | Idiopathic |
| Ischaemia | Thalamic syndrome |
| | Post-stroke pain |
| Neurotransmitter function | Complex regional pain syndrome |

Thus in one embodiment the invention relates to treatment of allodynia, hyperalgesia, or hypersensitivity in a subject diagnosed with a disorder listed in the table above. Preferably, the invention relates to treatment of hypersensitivity in a subject diagnosed with painful diabetic neuropathy, post-herpetic neuralgia, or sciatica. More preferably, the invention relates to treatment of allodynia or hyperalgesia in a subject diagnosed with painful diabetic neuropathy, post-herpetic neuralgia, or sciatica. In an even more preferred embodiment, the invention relates to treatment of allodynia in a subject diagnosed with painful diabetic neuropathy, post-herpetic neuralgia, or sciatica.

Method of Treatment of Allodynia, Hyperalgesia, Spontaneous Pain and/or Phantom Pain In one embodiment the present invention relates to the use of Meteorin for the treatment of allodynia, hyperalgesia, spontaneous pain and/or phantom pain. In a more preferred embodiment the present invention relates to the use of Meteorin for the treatment of allodynia, hyperalgesia and/or spontaneous pain. In an even one embodiment the present invention relates to the use of Meteorin for treatment of hyperalgesia and/or allodynia.

In a preferred embodiment the present invention relates to the use of Meteorin for treatment of allodynia. In a more preferred embodiment the present invention relates to the use of Meteorin for the treatment of mechanical allodynia. In an even more preferred embodiment the present invention relates to the use of Meteorin for treatment of thermal allodynia. In an even more preferred embodiment the present invention relates to the use of Meteorin for treatment of cold allodynia. In an even more preferred embodiment the present invention relates to the use of Meteorin for treatment of heat allodynia.

In another preferred embodiment the present invention relates to the use of Meteorin for the treatment of spontaneous pain.

In another preferred embodiment the present invention relates to the use of Meteorin for the treatment of hyperalgesia. In a more preferred embodiment the present invention relates to the use of Meteorin for the treatment of mechanical hyperalgesia. In an even more preferred embodiment the present invention relates to the use of Meteorin for the treatment of thermal hyperalgesia. In an even more preferred embodiment the present invention relates to the use of Meteorin for the treatment of cold hyperalgesia. In an even more preferred embodiment the present invention relates to the use of Meteorin for treatment of heat hyperalgesia.

Figure 11:
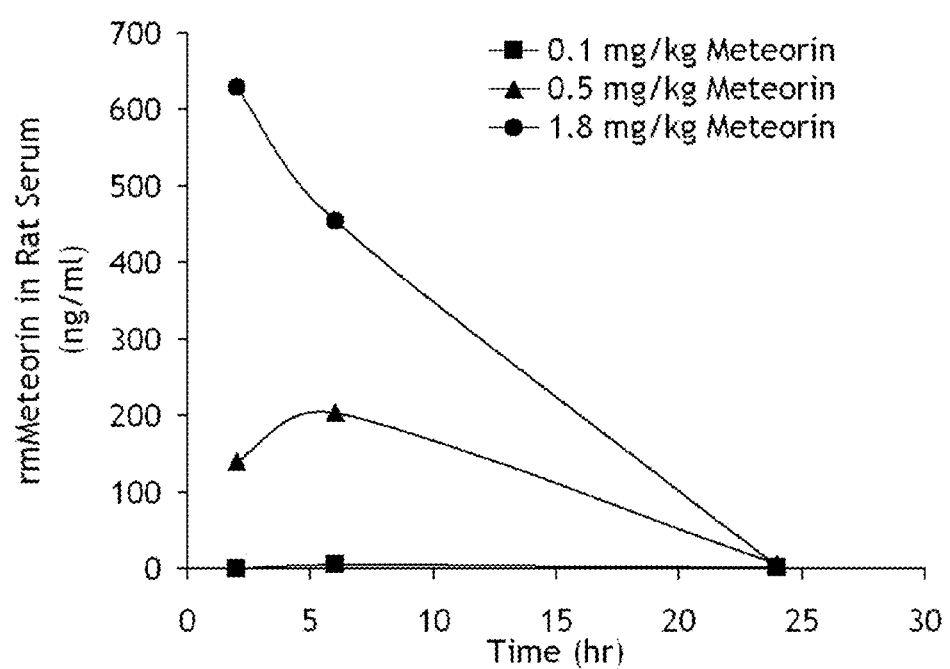
FIG. 11. Meteorin in rat serum post systemic administration. Animals were systemically injected with 0.1 mg/kg, 0.5 mg/kg or 1.8 mg/kg recombinant Meteorin at Day 39 (t=0). Serum samples were collected at 2, 6, 24 hr after injection and the concentration of Meteorin determined using ELISA. Meteorin was not detectable in serum samples from naïve control rats.

The appended examples (example 4) demonstrate that the effect of Meteorin is long-lasting in particular in view of the relatively short serum half-life of Meteorin (FIG. 11). This indicates that Meteorin not only alleviates the symptoms of hyperalgesia, hypersensitivity, allodynia and spontaneous pain, but that Meteorin may actually be capable of modifying the underlying disease or disorder. Thus, in one embodiment, the treatment is a disease modifying treatment.

The examples also demonstrate that some of the tested subject experienced full reversal of their sensory dysfunction. Thus in one embodiment, the treatment results in full reversal of sensory dysfunction, preferably full reversal of allodynia, more preferably full reversal of tactile allodynia in at least a subset of the treated subjects. In another preferred embodiment, the treatment results in substantially full reversal of hyperalgesia in at least a subset of the treated subjects.

Treatment of Neuropathic Pain

Neuropathic pain is a category of pain that includes several forms of chronic pain and which results from dysfunction of nervous rather than somatic tissue. Neuropathic pain, that is pain deriving from dysfunction of the central or peripheral nervous system, may also be a consequence of damage to peripheral nerves or to regions of the central nervous system, may result from disease, or may be idiopathic. Symptoms of neuropathic pain include sensations of burning, tingling, electricity, pins and needles, paresthesia, dysesthesia, stiffness, numbness in the extremities, feelings of bodily distortion, allodynia (pain evoked by stimulation that is normally innocuous), hyperalgesia (abnormal sensitivity to pain), hyperpathia (an exaggerated pain response persisting long after the pain stimuli cease), phantom pain, and spontaneous pain.

Current therapies for the management of neuropathic pain are of limited benefit to many patients, and involve undesirable side effects or dose-limiting toxicities. In addition, current therapies are symptomatic, not disease modifying. Needs remain for improved therapies for the management and treatment of neuropathic pain, especially those that have the capacity to modify the disease.

In a series of animal studies the present inventors have observed that administration of dosages of Meteorin leads to long lasting improvement in tactile and thermal allodynia as well as spontaneous pain. In several cases, the therapeutic effect is still detectable in the animals one week after administration of the last dosage. In other cases the therapeutic effect is still detectable and significantly different from control treatment as long as two or even three weeks after the last dosage.

In the observed cases, Meteorin polypeptide has been delivered as subcutaneous or intrathecal injections every second or third day for 9 or 11 days. Meteorin is undetectable in the serum of animals 24 hours after subcutaneous injection. Therefore any build-up of Meteorin under the observed administration schemes used is unlikely. The long lasting effect of Meteorin may be caused by epigenetic changes or by repair of the nerve damages in the animals. Repair may be through regain of function, neurogenesis or differentiation of neuronal precursors.

In any event it is highly surprising that a therapeutic effect can be observed so long time after treatment cessation. In approved neuropathic pain drugs, such as gabapentin, serotonin-norepinephrine reuptake inhibitors, tricyclic antidepressants, pain killers, cannabinoids, and opiods therapeutic therapeutic effect is not seen so long time after administration of the latest dosage. For example, in the case of opioids, efficacy is contingent on the drug being present in blood serum. When the blood serum level of the drug drops below a certain threshold, no therapeutic effect is observed.

As the present inventors have demonstrated the Meteorin administered at long dosage intervals is effective in treating different symptoms of different types neuropathic pain including thermal and tactile allodynia and spontaneous pain, the present inventors contemplate that neuropathic pain in general can be treated by administering Meteorin polypeptide at relatively long dosage intervals.

By a relatively long dosage interval is intended at least 2 days between dosages, such as at least 3 days between dosages, for example 2 dosages per week. More preferably the long dosages interval is at least one week, such as at least 2 weeks, more preferably at least 3 weeks, such as at least 4 weeks, or at least one month.

Expressed in a different way the dosage intervals are so long that following one dosage of Meteorin polypeptide, the polypeptide is no longer detectable in the serum of the subject to be treated when the next dosage is administered. In another embodiment the blood serum level is below 10 ng/mL, such as below 5 ng/mL, more preferably below 1 ng/mL, such as below 0.5 ng/mL, for example below 0.1 ng/mL.

In some embodiments, the long dosage range is preceded by more frequent initial administration of Meteorin, e.g., twice daily, daily, once every two days, once every three days, or once every four days. This initial dosing schedule may be maintained e.g., for 2, 3, 4, 5, 6, 7, 9, 11, 14, 21 days, or more. After completion of this dosing schedule, meteorin can be administered less frequently, e.g., as described above.

Thus in one aspect, the invention relates to a method of treating neuropathic pain in a human subject in need thereof comprising administering to the subject a therapeutically effective amount of a neurotrophic polypeptide comprising an amino acid sequence having at least 70% identity to the amino acid sequence of SEQ ID NO: 3. wherein said administration is three times per week or more infrequently.

Preferably, the administration is weekly or more infrequent administration. Even more preferably the administration is bi-weekly or more infrequent administration.

In one embodiment the therapeutic effect of said treatment ameliorates at least one symptom of neuropathic pain for the entire period between polypeptide administrations. The at least one symptom may be selected from the group consisting of allodynia, hyperalgesia, spontaneous pain, phantom pain, sensations of burning, tingling, electricity, pins and needles, paresthesia, dysesthesia, stiffness, numbness in the extremities, feelings of bodily distortion, and hyperpathia (an exaggerated pain response persisting long after the pain stimuli cease). Preferably the at least one symptom is selected from allodynia, hyperalgesia and spontaneous pain. More preferably allodynia.

Preferably said treatment does not maintain measurable levels of said polypeptide in the serum of said subject for the entire period between polypeptide administrations. Preferably, the level of said polypeptide in the serum of said subject falls below 10 ng/mL, such as below 5 ng/mL, more preferably below 1 ng/mL, such as below 0.5 ng/mL, for example below 0.1 ng/mL between polypeptide administrations.

In another related aspect, the invention relates to a method of treating neuropathic pain in a human subject in need thereof comprising administering to the subject a therapeutically effective amount of a neurotrophic polypeptide comprising an amino acid sequence having at least 70% identity to the amino acid sequence of SEQ ID NO: 3, wherein said treatment does not maintain measurable levels of said polypeptide in the serum of said subject for the entire interval between polypeptide administrations.

The invention also relates to use of the polypeptide of the invention in said methods of treatment of neuropathic pain and to use of the polypeptides of the invention in the manufacture of a medicament for said treatment of neuropathic pain.

Preferably the level of said polypeptide in the serum of said subject falls below 10 ng/mL, such as below 5 ng/mL, more preferably below 1 ng/mL, such as below 0.5 ng/mL, for example below 0.1 ng/mL between polypeptide administrations.

For these aspects of the invention relating to treatment of neuropathic pain using long dosage intervals, the neurotrophic polypeptide preferably has at least 85% sequence identity to the amino acid sequence of SEQ ID NO: 3, more preferably at least 90%, more preferably at least 95%, more preferably at least 98%.

In one embodiment the neurotrophic polypeptide comprises the consensus sequence of SEQ ID NO:11.

Preferably the neurotrophic polypeptide has cysteine residues at positions 7, 28, 59, 95, 148, 151, 161, 219, 243, and 265 relative to the amino acid sequence of SEQ ID NO:3.

Meteorin

The present invention relates to the use of polypeptides being identified as Meteorin protein and polynucleotides encoding said protein, in the treatment of allodynia, hyperalgesia, spontaneous pain and/or phantom pain. The delivery is in one embodiment contemplated to be by use of a capsule for delivery of a secreted biologically active Meteorin and/or a homologue thereof to a subject. The Meteorin protein has been identified in human beings (SEQ ID No. 2), mouse (SEQ ID No. 5), and rat (SEQ ID No. 8) and a variety of other species.

Human Meteorin exists as a 293 amino acid precursor, which can be processed to give rise to at least one biologically active peptide. Meteorin is expressed at high levels in the nervous system and the eye, and in particular subregions of the brain. The mouse (SEQ ID No 5) and rat (SEQ ID No 8) Meteorin precursors consist of 291 amino acids, and the % identities with the human Meteorin protein (SEQ ID NO: 2) are 80.3 and 80.2, respectively (See FIG. 6).

Human Meteorin contains an N-terminal signal peptide sequence of 23 amino acids, which is cleaved at the sequence motif ARA-GY. This signal peptide cleavage site is predicted by the SignalP method. The N-terminal of mouse Meteorin has been has been verified by N-terminal sequencing (Jør- gensen et al., Characterization of meteorin—An evolutionary conserved neurotrophic factor, J mol Neurosci 2009 September; 39 (1-2): 104-116).

Table 1 shows the % sequence identity between full length human Meteorin versus mouse and rat sequences. See alignment in FIG. 6a.

| Sequence | % id |
|---|---|
| human | — |
| mouse | 80.3 |
| rat | 80.2 |

Table 2 shows the % sequence identity between human Meteorin versus mouse and rat sequences after removal of N-terminal signal peptide. See alignment in FIG. 6b.

| Sequence | % id |
|---|---|
| human | — |
| mouse | 81.9 |
| rat | 79.6 |

Based on the fully conserved residues, a consensus sequence for mature Meteorin can be derived (FIG. 6c), wherein X is independently selected from any of the 21 naturally occurring amino acid encoded by DNA. In a preferred embodiment a variant Meteorin comprises the consensus sequence.

The therapeutic effect of Meteorin may be mediated through a neurotrophic effect, an effect on growth including proliferation, regeneration, regain of function, improvement of function, survival, migration, and/or differentiation of targeted cells.

One biological function of Meteorin is the ability to induce neurite outgrowth in dissociated dorsal root ganglia (DRG) cultures as described in Jorgensen et al., Characterization of meteorin—An evolutionary conserved neurotrophic factor, J mol Neurosci 2009 September; 39 (1-2): 104-116 and Nishino et al., "Meteorin: a secret3ed protein that regulates glial cell differentitaion and promotes axonal extension", EMBO J., 23(9):1998-2008 (2004).

Due to the high conservation of the cysteines, it is expected that these residues play an important role in the secondary and tertiary structure of the bioactive protein. One or more of the cysteines may participate in the formation of intra- and/or intermolecular cystin-bridges.

It has been demonstrated that Meteorin has a stimulating effect on the percentage of neurons generated by a human neural stem cell line (hNS1, formerly called HNSC. 100) and Meteorin also has a stimulating effect on generation of neurons in a primary culture of rat striatal cells (see WO 2005/095450).

Administration and Formulation

Meteorin polypeptides may be administered in any manner, which is medically acceptable. This may include injections, by parenteral routes such as intravenous, intravascular, intraarterial, subcutaneous, intramuscular, intratumor, intraperitoneal, intraventricular, intraepidural, intrathecal, intracerebroventricular, intercerebral, or others as well as nasal, or topical. Slow release administration is also specifically included in the invention, by such means as depot injections or erodible implants.

Administration of Meteorin according to this invention may be achieved using any suitable delivery means, including:

injection, either subcutaneously, intravenously, intra-arterially, intramuscularly, intrathecally or to other suitable site;
pump (see, e.g., Annals of Pharmacotherapy, 27:912 (1993); Cancer, 41:1270 (1993); Cancer Research, 44:1698 (1984), incorporated herein by reference),
microencapsulation (see, e.g., U.S. Pat. Nos. 4,352,883; 4,353,888; and 5,084,350, herein incorporated by reference),
slow release polymer implants (see, e.g., Sabel, U.S. Pat. No. 4,883,666, incorporated herein by reference),
encapsulated cells (see, "Biocompatible capsules"),
unencapsulated cell grafts (see, e.g., U.S. Pat. Nos. 5,082, 670 and 5,618,531, each incorporated herein by reference); and
inhalation.

Administration may be by periodic injections of a bolus of the preparation, or may be made more continuous by intravenous or intraperitoneal administration from a reservoir which is external (e.g., an IV bag) or internal (e.g., a bioerodable implant, a bioartificial organ, a biocompatible capsule of Meteorin production cells, or a colony of implanted Meteorin production cells). See, e.g., U.S. Pat. Nos. 4,407,957, 5,798, 113, and 5,800,828, each incorporated herein by reference.

Localised delivery may be by such means as delivery via a catheter to one or more arteries. In one embodiment of the present invention localised delivery comprises delivery using encapsulated cells (as described in the section "biocompatible capsule"). A further type of localised delivery comprises local delivery of gene therapy vectors, which are normally injected.

In a preferred embodiment of the present invention the administration is parenteral injection, preferably subcutaneous injection or intrathecal injection.

Whilst it is possible for the compounds of the present invention to be administered as the raw chemical, it is preferred to present them in the form of a pharmaceutical formulation. The pharmaceutical formulations may be prepared by conventional techniques, e.g. as described in Remington: The Science and Practice of Pharmacy 2005, Lippincott, Williams & Wilkins.

The term "pharmaceutically acceptable carrier" means one or more organic or inorganic ingredients, natural or synthetic, with which Meteorin polypeptide is combined to facilitate its application. A suitable carrier includes sterile saline although other aqueous and non-aqueous isotonic sterile solutions and sterile suspensions known to be pharmaceutically acceptable are known to those of ordinary skill in the art.

The compounds of the present invention may be formulated for parenteral administration and may be presented in unit dose form in ampoules, pre-filled syringes, small volume infusion or in multi-dose containers, optionally with an added preservative. The compositions may take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and may contain agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount can be determined by one of ordinary skill in the art employing such factors and using no more than routine experimentation.

A liposome system may be any variety of unilamellar vesicles, multilamellar vesicles, or stable plurilamellar vesicles, and may be prepared and administered according to methods well known to those of skill in the art, for example in accordance with the teachings of U.S. Pat. Nos. 5,169,637, 4,762,915, 5,000,958 or 5,185,154. In addition, it may be desirable to express the novel polypeptides of this invention, as well as other selected polypeptides, as lipoproteins, in order to enhance their binding to liposomes. A recombinant Meteorin protein is purified, for example, from CHO cells by immunoaffinity chromatography or any other convenient method, then mixed with liposomes and incorporated into them at high efficiency. The liposome-encapsulated protein may be tested in vitro for any effect on stimulating cell growth.

Where slow-release administration of a Meteorin polypeptide is desired in a formulation with release characteristics suitable for the treatment of any disease or disorder requiring administration of a Meteorin polypeptide, microencapsulation of a Meteorin polypeptide is contemplated. Microencapsulation of recombinant proteins for sustained release has been successfully performed with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Hora et al., Bio/Technology, 8:755-758 (1990); Cleland, "Design and Production of Single Immunization Vaccines Using Polylactide Polyglycolide Microsphere Systems," in Vaccine Design The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010.

The slow-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41.

In one embodiment of the present invention a composition comprising Meteorin is contemplated. The composition may comprise an isolated polypeptide as described herein, an isolated nucleic acid as described herein, a Meteorin encoding expression vector as described herein, a cell line expressing Meteorin as described herein or a biocompatible capsule secreting Meteorin as described herein.

Dosages

Various dosing regimes for systemic administration are contemplated. In one embodiment, methods of administering to a subject a formulation comprising a Meteorin polypeptide include administering Meteorin at a dosage of between 1 µg/kg and 10,000 µg/kg body weight of the subject, per dose. In another embodiment, the dosage is between 1 µg/kg and 7,500 µg/kg body weight of the subject, per dose. In a further embodiment, the dosage is between 1 µg/kg and 5,000 µg/kg body weight of the subject, per dose. In a different embodiment, the dosage is between 1 µg/kg and 2,000 µg/kg body weight of the subject, per dose. In yet another embodiment, the dosage is between 1 µg/kg and 1,000 µg/kg body weight of the subject, per dose. In yet another embodiment, the dosage is between 1 µg/kg and 700 µg/kg body weight of the subject, per dose. In a more preferable embodiment, the dosage is between 5 µg/kg and 500 µg/kg body weight of the subject, per dose. In a most preferable embodiment, the dosage is between 10 µg/kg and 100 µg/kg body weight of the subject, per dose. In a preferred embodiment the subject to be treated is human.

Guidance as to particular dosages and methods of delivery is provided in the literature; see, for example, WO 02/78730 and WO 07/100,898. Guidance to the calculation of the human equivalent dosages based on dosages used in animal experiments is provided in Reagan-Shaw et al., FASEB J, 22, 659-661 (2007).

The dose administered must be carefully adjusted to the age, weight and condition of the individual being treated, as well as the route of administration, dosage form and regimen, and the result desired, and the exact dosage should be determined by the practitioner.

In one embodiment of the present invention the administration is repeated daily. In another embodiment the administration is repeated at least 1-3 times weekly, such as 2-5 times weekly, such as 3-6 times weekly, once every three days, once every four days, once every five days, once every six days, or once every 7 days.

In other embodiments, meteorin is administered at relatively long dosage interval. A relatively long dosage interval is intended to include at least 2 days between dosages, such as at least 3 days between dosages, for example 2 dosages per week. More preferably the long dosages intervals is at least one week, such as at least 2 weeks, more preferably at least 3 weeks, such as at least 4 weeks, or at least one month.

Expressed in a different way the dosage intervals are so long that following one dosage of Meteorin polypeptide, the polypeptide is no longer detectable in the serum of the subject to be treated when the next dosage is administered. In another embodiment the blood serum level is below 10 ng/mL, such as below 5 ng/mL, more preferably below 1 ng/mL, such as below 0.5 ng/mL, for example below 0.1 ng/mL.

In some embodiments, the initial administration of Meteorin is, e.g., twice daily, daily, once every two days, once every three days, or once every four days. This dosing schedule may be maintained e.g., for 2, 3, 4, 5, 6, 7, 9, 11, 14, 21 days, or more. After completion of this dosing schedule, meteorin can be administered less frequently, e.g., as described above.

Meteorin Polypeptides

In addition to full-length Meteorin, substantially full-length Meteorin, and to pro-Meteorin, the present invention provides for biologically active variants of the polypeptides. A Meteorin polypeptide or fragment is biologically active if it exhibits a biological activity of naturally occurring Meteorin as described herein, such as being neurotrophic. It is to be understood that the invention relates to Meteorin as herein defined.

The invention relates to an isolated polypeptide molecule for use in a method of treatment of allodynia, hyperalgesia, spontaneous pain and/or phantom pain, said polypeptide comprising an amino acid sequence selected from the group consisting of:
a) the amino acid sequence selected from the group consisting of SEQ ID No. 3, 6 and 9;
b) a biologically active sequence variant of the amino acid sequence selected from the group consisting of SEQ ID No. 3, 6 and 9, wherein the variant has at least 70% sequence identity to said SEQ ID No.; and c) a biologically active fragment of at least 50 contiguous amino acids of any of a) or b) wherein the fragment is at least 70% identical to said SEQ ID NO.

In one embodiment the invention relates to an isolated polypeptide selected from the group consisting of:

i) $AA_{30}$-$AA_{288}$ of SEQ ID No 2, and polypeptides having from one to five extra amino acids from the native sequence in one or both ends, up to $AA_{25}$-$AA_{293}$ of SEQ ID No 2;

ii) $AA_{28}$-$AA_{286}$ of SEQ ID No 8 and polypeptides having from one to five extra amino acids from the native sequence in one or both ends, up to $AA_{23}$-$AA_{291}$ of SEQ ID No 8;

iii) $AA_{31}$-$AA_{289}$ of SEQ ID No 5 and polypeptides having from one to five extra amino acids from the native sequence in one or both ends, up to $AA_{26}$-$AA_{294}$ of SEQ ID No 5; and iv) variants of said polypeptides, wherein any amino acid specified in the chosen sequence is changed to a different amino acid, provided that no more than 20 of the amino acid residues in the sequence are so changed.

Biological activity preferably is neurotrophic activity. Neurotrophically active variants may be defined with reference to one or more of the other in vitro and/or in vivo neurotrophic assays described above in WO 2005/095450, in particular the DRG assay.

A preferred biological activity is the ability to elicit substantially the same response as in the DRG assay described in Jorgensen et al., Characterization of meteorin—An evolutionary conserved neurotrophic factor, J mol Neurosci 2009 September; 39 (1-2): 104-116. In this assay DRG cells are grown in the presence of full length human Meteorin coding sequence (SEQ ID NO 3). By substantially the same response in the DRG assay is intended that the neurite outgrowth from DRG cells is at least 20% of the number obtained in the DRG assay described in Jorgensen et al., Characterization of meteorin—An evolutionary conserved neurotrophic factor, J mol Neurosci 2009 September; 39 (1-2): 104-116, more preferably at least 30%, more preferably at least 40%, more preferably at least 50%, more preferably at least 60%, more preferably at least 70%, more preferably at least 75%, more preferably at least 80%, more preferably at least 85%, more preferably at least 90%. The biological activity of a fragment or variant of Meteorin may also be higher than that of the naturally occurring Meteorin (SEQ ID NO 3).

Variants can differ from naturally occurring Meteorin in amino acid sequence or in ways that do not involve sequence, or in both ways. Variants in amino acid sequence ("sequence variants") are produced when one or more amino acids in naturally occurring Meteorin is substituted with a different natural amino acid, an amino acid derivative or non-native amino acid. Particularly preferred variants include naturally occurring Meteorin, or biologically active fragments of naturally occurring Meteorin, whose sequences differ from the wild type sequence by one or more conservative and/or semi-conservative amino acid substitutions, which typically have minimal influence on the secondary and tertiary structure and hydrophobic nature of the protein or peptide. Variants may also have sequences, which differ by one or more non-conservative amino acid substitutions, deletions or insertions, which do not abolish the Meteorin biological activity. The Clustal W alignment in FIG. 6 can be used to predict which amino acid residues can be substituted without substantially affecting the biological activity of the protein. In a preferred embodiment a variant Meteorin sequence comprises the consensus sequence having SEQ ID NO 11.

Substitutions within the following group (Clustal W, 'strong' conservation group) are to be regarded as conservative substitutions within the meaning of the present invention
S,T,A; N,E,Q,K; N,H,Q,K; N,D,E,Q; Q,H,R,K; M,I,L,V; M,I,L,F; H,Y; F,Y,W.

Substitutions within the following group (Clustal W, 'weak' conservation group) are to be regarded as semi-conservative substitutions within the meaning of the present invention
C,S,A; A,T,V; S,A,G; S,T,N,K; S,T,P,A; S,G,N,D; S,N,D,E,Q,K; N,D,E,Q,H,K; N,E,Q,H,R,K; V,L,I,M; H,F,Y.

Other variants within the invention are those with modifications which increase peptide stability. Such variants may contain, for example, one or more nonpeptide bonds (which replace the peptide bonds) in the peptide sequence. Also included are: variants that include residues other than naturally occurring L-amino acids, such as D-amino acids or non-naturally occurring or synthetic amino acids such as beta or gamma amino acids and cyclic variants. Incorporation of D-amino acids instead of L-amino acids into the polypeptide may increase its resistance to proteases. See, e.g., U.S. Pat. No. 5,219,990. Splice variants are specifically included in the invention.

When the result of a given substitution cannot be predicted with certainty, the derivatives may be readily assayed according to the methods disclosed herein to determine the presence or absence of neurotrophic activity, preferably using the DRG assay described in Jorgensen et al., Characterization of meteorin—An evolutionary conserved neurotrophic factor, J mol Neurosci 2009 September; 39 (1-2): 104-116.

In one embodiment, the polypeptide is a naturally occurring allelic variant of the sequence selected from the group consisting of SEQ ID No. 3, 6 and 9. This polypeptide may comprise an amino acid sequence that is the translation of a nucleic acid sequence differing by a single nucleotide from a nucleic acid sequence selected from the group consisting of SEQ ID No. 1, 4 and 7.

A variant polypeptide as described herein, in one embodiment comprises a polypeptide wherein any amino acid specified in the chosen sequence is changed to provide a conservative substitution.

Variants within the scope of the invention in one embodiment include proteins and peptides with amino acid sequences having at least 70 percent identity with human, murine or rat Meteorin (SEQ ID NO: 3, 6, and 9). More preferably the sequence identity is at least 75%, more preferably at least 80%, more preferably at least 85%, more preferably at least 90%, more preferably at least 95%, more preferably at least 98%.

In a preferred embodiment the sequence identity of the variant Meteorin is determined with reference to a human Meteorin polypeptide (SEQ ID No 3).

In one embodiment, the variants include proteins comprising an amino acid sequence having at least 70% sequence identity to SEQ ID NO 3, more preferably at least 75%, more preferably at least 80%, more preferably at least 85%, more preferably at least 90%, more preferably at least 95%, more preferably at least 98%.

In one embodiment, preferred variants include proteins comprising an amino acid sequence having at least 70% sequence identity to SEQ ID NO 6, more preferably at least 75%, more preferably at least 80%, more preferably at least 85%, more preferably at least 90%, more preferably at least 95%, more preferably at least 98%.

In one embodiment, preferred variants include proteins comprising an amino acid sequence having at least 70% sequence identity to SEQ ID NO 9, more preferably at least 75%, more preferably at least 80%, more preferably at least 85%, more preferably at least 90%, more preferably at least 95%, more preferably at least 98%.

In one embodiment, preferred variants of Meteorin include proteins comprising 50-270 amino acids, more preferably 75-270 amino acids, more preferably 90-270 amino acids, more preferably 100-270 amino acids, more preferably 125-270 amino acids, more preferably 150-270 amino acids, more preferably 175-270 amino acids, more preferably 200-270 amino acids, more preferably 225-270 amino acids, more preferably 250-270 amino acids.

In one embodiment, a variant Meteorin at corresponding positions comprises the residues marked in FIG. 6 as fully conserved (*), more preferably a variant Meteorin also comprises at corresponding positions the residues marked in FIG. 6 as strongly conserved (: strongly conserved groups include: S,T,A; N,E,Q,K; N,H,Q,K; N,D,E,Q; Q,H,R,K; M,I,L,V; M,I,L,F; H,Y; F,Y,W), more preferably a variant Meteorin also comprises at corresponding positions the residues marked in FIG. 6 as less conserved (. less conserved groups include: C,S,A; A,T,V; S,A,G; S,T,N,K; S,T,P,A; S,G,N,D; S,N,D,E,Q,K; N,D,E,Q,H,K; N,E,Q,H,R,K; V,L,I,M; H,F,Y). In particular, it is contemplated that the conserved cysteines must be located at corresponding positions in a variant Meteorin. Thus in one embodiment, a variant Meteorin sequence has cysteine residues at positions 7, 28, 59, 95, 148, 151, 161, 219, 243, and 265 relative to the amino acid sequence of SEQ ID NO: 3.

In one embodiment the neurotrophic polypeptide comprises the consensus sequence of SEQ ID NO:11. The consensus sequence comprises the amino acid residues conserved in human, mouse and rat meteorin as shown in FIG. 6. Preferably the neurotrophic polypeptide has cysteine residues at positions 7, 28, 59, 95, 148, 151, 161, 219, 243, and 265 relative to the amino acid sequence of SEQ ID NO:3.

Non-sequence modifications may include, for example, in vivo or in vitro chemical derivatisation of portions of naturally occurring Meteorin, as well as acetylation, methylation, phosphorylation, carboxylation, PEG-ylation, or glycosylation. Just as it is possible to replace substituents of the protein, it is also possible to substitute functional groups, which are bound to the protein with groups characterized by similar features. Such modifications do not alter primary sequence. These will initially be conservative, i.e., the replacement group will have approximately the same size, shape, hydrophobicity and charge as the original group.

Many amino acids, including the terminal amino acids, may be modified in a given polypeptide, either by natural processes such as glycosylation and other post-translational modifications, or by chemical modification techniques which are well known in the art. Among the known modifications which may be present in polypeptides of the present invention are, to name an illustrative few, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance, I. E. Creighton, Proteins-Structure and Molecular Properties, 2nd Ed., W. H. Freeman and Company, New York, 1993. Many detailed reviews are available on this subject, such as, for example, those provided by Wold, F., in Posttranslational Covalent Modification of Proteins, B. C. Johnson, Ed., Academic Press, New York, pp 1-12, 1983; Seifter et al., Meth. Enzymol. 182: 626-646, 1990 and Rattan et al., Protein Synthesis: Posttranslational Modifications and Aging, Ann. N.Y. Acad. Sci. 663: 48-62, 1992.

In addition, the protein may comprise a protein tag to allow subsequent purification and optionally removal of the tag using an endopeptidase. The tag may also comprise a protease cleavage site to facilitate subsequent removal of the tag. Non-limiting examples of affinity tags include a polyhis tag, a GST tag, a HA tag, a Flag tag, a C-myc tag, a HSV tag, a V5 tag, a maltose binding protein tag, a cellulose binding domain tag. Preferably for production and purification, the tag is a polyhistag. Preferably, the tag is in the C-terminal portion of the protein.

The native signal sequence of Meteorin may also be replaced in order to increase secretion of the protein in recombinant production in other mammalian cell types.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell's posttranslational modification capacity and the modification signals present in the polypeptide amino acid sequence. For instance, glycosylation often does not occur in bacterial hosts such as E. coli. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation, inter alia. Similar considerations apply to other modifications.

It will be appreciated that the same type of modification may be present to the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

Meteorin Nucleotide Sequences

The invention provides medical use of genomic DNA and cDNA coding for Meteorin, including for example the human cDNA nucleotide sequence (SEQ ID No. 1 and 10), the mouse cDNA sequences (SEQ ID NO 4) and rat cDNA sequences (SEQ ID No. 7).

Variants of these sequences are also included within the scope of the present invention.

The invention relates to an isolated nucleic acid molecule for use in a method of treatment of allodynia, hyperalgesia, spontaneous pain and/or phantom pain, said nucleic acid molecule comprising a nucleic acid sequence encoding a polypeptide, said polypeptide comprising an amino acid sequence selected from the group consisting of:
  i. The amino acid sequence of SEQ ID NO: 3;
  ii. A biologically active sequence variant of the amino acid sequence of SEQ ID NO:3, wherein the variant has at least 70% sequence identity to SEQ ID NO:3; and
  iii. A biologically active fragment of at least 50 contiguous amino acids of i) or ii) wherein the fragment is at least 70% identical to SEQ ID NO: 3.

In one embodiment the invention relates to an isolated nucleic acid molecule for use in a method of treatment of allodynia, hyperalgesia, spontaneous pain and/or phantom pain encoding a polypeptide, said polypeptide comprising an amino acid sequence selected from the group consisting of:
  i) $AA_{30}$-$AA_{288}$ of SEQ ID No 2, and polypeptides having from one to five extra amino acids from the native sequence in one or both ends, up to $AA_{25}$-$AA_{293}$ of SEQ ID No 2;
  ii) $AA_{28}$-$AA_{286}$ of SEQ ID No 8 and polypeptides having from one to five extra amino acids from the native sequence in one or both ends, up to $AA_{23}$-$AA_{291}$ of SEQ ID No 8;
  iii) $AA_{31}$-$AA_{289}$ of SEQ ID No 5 and polypeptides having from one to five extra amino acids from the native sequence in one or both ends, up to $AA_{26}$-$AA_{294}$ of SEQ ID No 5; and
  iv) variants of said polypeptides, wherein any amino acid specified in the chosen sequence is changed to a different amino acid, provided that no more than 20 of the amino acid residues in the sequence are so changed.

The nucleic acid molecule may comprise the nucleotide sequence of a naturally occurring allelic nucleic acid variant.

The nucleic acid molecule of the invention may encode a variant polypeptide, wherein the variant polypeptide has the polypeptide sequence of a naturally occurring polypeptide variant.

In one embodiment the nucleic acid molecule differs by a single nucleotide from a nucleic acid sequence selected from the group consisting of SEQ ID No. 1, 4, 7 and 10.

Preferably the encoded polypeptide has at least 60% sequence identity to a sequence selected from the group consisting of SEQ ID No. 3 preferably at least 65% sequence identity, more preferably at least 70% sequence identity, more preferably, 75% sequence identity, more preferably at least 80% sequence identity, more preferably at least 85% sequence identity, more preferably at least 90% sequence identity, more preferably at least 95% sequence identity, more preferably at least 98% sequence identity, more preferably wherein the polypeptide has a sequence selected from the group consisting of said SEQ ID No.s. Said sequences constitute human Meteorin.

In a preferred embodiment, the encoded polypeptide comprises the consensus sequence having SEQ ID NO:11.

In a preferred embodiment the encoded polypeptide has at least 70% sequence identity to SEQ ID No. 3, more preferably at least 75%, more preferably at least 80%, more preferably at least 95%, more preferably at least 98%, more preferably wherein said polypeptide has the sequence of SEQ ID No. 3.

In one aspect the nucleic acid molecule comprises a nucleotide sequence selected from the group consisting of
a) the nucleotide sequence selected from the group consisting of SEQ ID No. 1, 4, 7 and 10;
b) a nucleotide sequence having at least 70% sequence identity to a nucleotide sequence selected from the group consisting of SEQ ID No. 1, 4, 7 and 10; and
c) a nucleic acid sequence of at least 150 contiguous nucleotides of a sequence selected from the group consisting of SEQ ID No. 1, 4, 7 and 10;

In one embodiment, the isolated polynucleotide of the invention has at least 60, more preferably at least 65%, more preferably at least 70%, more preferably at least 75%, more preferably at least 80%, preferably at least 85%, more preferred at least 90%, more preferred at least 95%, more preferred at least 98% sequence identity to the polynucleotide sequence presented as SEQ ID NO: 1.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence presented as SEQ ID NO: 10.

In one embodiment, preferred isolated polynucleotide variants of the invention comprises 150-900 nucleic acids, more preferably 175-900 nucleic acids, more preferably 200-900 nucleic acids, more preferably 225-900 nucleic acids, more preferably 250-900 nucleic acids, more preferably 300-900 nucleic acids, more preferably 350-900 nucleic acids, more preferably 400-900 nucleic acids, more preferably 450-900 nucleic acids, more preferably 500-900 nucleic acids, more preferably 550-900 nucleic acids, more preferably 600-900 nucleic acids, more preferably 650-900 nucleic acids, more preferably 700-900 nucleic acids, more preferably 750-900 nucleic acids, more preferably 800-900 nucleic acids, more preferably 850-900 nucleic acids.

A preferred group of isolated polynucleotides include SEQ ID No 1 and 10, which are human Meteorin cDNA sequences. Generally the cDNA sequence is much shorter than the genomic sequences are more easily inserted into an appropriate expression vector and transduced/fected into a production cell or a human cell in vivo or ex vivo.

In addition, the nucleotide sequences of the invention include sequences, which are derivatives of these sequences. The invention also includes vectors, liposomes and other carrier vehicles, which encompass one of these sequences or a derivative of one of these sequences. The invention also includes proteins transcribed and translated from Meteorin cDNA, preferably human Meteorin cDNA, including but not limited to human Meteorin and derivatives and variants.

Codon optimised nucleic acid molecules for enhanced expression in selected host cells, including but not limited to *E. coli*, yeast species, Chinese Hamster, Baby Hamster, insect, fungus, and human are also contemplated.

Variant nucleic acids can be made by state of the art mutagenesis methods. Methods for shuffling coding sequences from human with those of mouse, rat or chimpanzee are also contemplated.

Variant nucleic acids made by exchanging amino acids present in human Meteorin with the amino acid present in mouse or rat Meteorin at the corresponding position, should this amino acid be different from the one present in human Meteorin.

Viral Vectors

Broadly, gene therapy seeks to transfer new genetic material to the cells of a patient with resulting therapeutic benefit to the patient. Such benefits include treatment or prophylaxis of a broad range of diseases, disorders and other conditions.

Ex vivo gene therapy approaches involve modification of isolated cells (including but not limited to stem cells, neural and glial precursor cells, and foetal stem cells), which are then infused, grafted or otherwise transplanted into the patient. See, e.g., U.S. Pat. Nos. 4,868,116, 5,399,346 and 5,460,959. In vivo gene therapy seeks to directly target host patient tissue in vivo.

Viruses useful as gene transfer vectors include papovavirus, adenovirus, vaccinia virus, adeno-associated virus, herpesvirus, and retroviruses. Suitable retroviruses include the group consisting of HIV, SIV, FIV, EIAV, MoMLV. A further group of suitable retroviruses includes the group consisting of HIV, SIV, FIV, EAIV, CIV. Another group of preferred virus vectors includes the group consisting of alphavirus, adenovirus, adeno associated virus, baculovirus, HSV, coronavirus, Bovine papilloma virus, Mo-MLV, preferably adeno associated virus.

Preferred viruses for treatment of disorders of the nervous system are lentiviruses and adeno-associated viruses. Both types of viruses can integrate into the genome without cell divisions, and both types have been tested in pre-clinical animal studies for indications of the nervous system, in particular the central nervous system.

Methods for preparation of AAV are described in the art, e.g. U.S. Pat. No. 5,677,158. U.S. Pat. Nos. 6,309,634 and 6,683,058 describe examples of delivery of AAV to the central nervous system.

Preferably, a lentivirus vector is a replication-defective lentivirus particle. Such a lentivirus particle can be produced from a lentiviral vector comprising a 5' lentiviral LTR, a tRNA binding site, a packaging signal, a promoter operably linked to a polynucleotide signal encoding said fusion protein, an origin of second strand DNA synthesis and a 3' lentiviral LTR. Methods for preparation and in vivo administration of lentivirus to neural cells are described in US 20020037281 (Methods for transducing neural cells using lentiviral vectors).

Retroviral vectors are the vectors most commonly used in human clinical trials, since they carry 7-8 kb and since they have the ability to infect cells and have their genetic material stably integrated into the host cell with high efficiency. See, e.g., WO 95/30761; WO 95/24929. Oncovirinae require at least one round of target cell proliferation for transfer and integration of exogenous nucleic acid sequences into the patient. Retroviral vectors integrate randomly into the patient's genome. Retroviruses can be used to target stem cells of the nervous system as very few cell divisions take place in other cells of the nervous system (in particular the CNS).

Three classes of retroviral particles have been described; ecotropic, which can infect murine cells efficiently, and amphotropic, which can infect cells of many species. The third class includes xenotrophic retrovirus which can infect cells of another species than the species which produced the virus. Their ability to integrate only into the genome of dividing cells has made retroviruses attractive for marking cell lineages in developmental studies and for delivering therapeutic or suicide genes to cancers or tumors.

For use in human patients, the retroviral vectors must be replication defective. This prevents further generation of infectious retroviral particles in the target tissue—instead the replication defective vector becomes a "captive" transgene stable incorporated into the target cell genome. Typically in replication defective vectors, the gag, env, and pol genes have been deleted (along with most of the rest of the viral genome). Heterologous DNA is inserted in place of the deleted viral genes. The heterologous genes may be under the control of the endogenous heterologous promoter, another heterologous promoter active in the target cell, or the retroviral 5' LTR (the viral LTR is active in diverse tissues). Typically, retroviral vectors have a transgene capacity of about 7-8 kb.

Replication defective retroviral vectors require provision of the viral proteins necessary for replication and assembly in trans, from, e.g., engineered packaging cell lines. It is important that the packaging cells do not release replication competent virus and/or helper virus. This has been achieved by expressing viral proteins from RNAs lacking the ψ signal, and expressing the gag/pol genes and the env gene from separate transcriptional units. In addition, in some 2. and 3. generation retriviruses, the 5' LTR's have been replaced with non-viral promoters controlling the expression of these genes, and the 3' promoter has been minimised to contain only the proximal promoter. These designs minimize the possibility of recombination leading to production of replication competent vectors, or helper viruses.

Expression Vectors

Construction of vectors for recombinant expression of Meteorin polypeptides for use in the invention may be accomplished using conventional techniques which do not require detailed explanation to one of ordinary skill in the art. For review, however, those of ordinary skill may wish to consult Maniatis et al., in Molecular Cloning: A Laboratory Manual, Cold Spring Harbor Laboratory, (NY 1982). Expression vectors may be used for generating producer cells for recombinant production of Meteorin polypeptides for medical use, and for generating therapeutic cells secreting Meteorin polypeptides for naked or encapsulated therapy.

Briefly, construction of recombinant expression vectors employs standard ligation techniques. For analysis to confirm correct sequences in vectors constructed, the genes are sequenced using, for example, the method of Messing, et al., (Nucleic Acids Res., 9: 309-, 1981), the method of Maxam, et al., (Methods in Enzymology, 65: 499, 1980), or other suitable methods which will be known to those skilled in the art.

Size separation of cleaved fragments is performed using conventional gel electrophoresis as described, for example, by Maniatis, et al., (Molecular Cloning, pp. 133-134, 1982).

For generation of efficient expression vectors, these should contain regulatory sequences necessary for expression of the encoded gene in the correct reading frame. Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many genes consists of the promoter and in some cases enhancer or regulator elements (Banerji et al., Cell 27: 299 (1981); Corden et al., Science 209: 1406 (1980); and Breathnach and Chambon, Ann. Rev. Biochem. 50: 349 (1981)). For retroviruses, control elements involved in the replication of the retroviral genome reside in the long terminal repeat (LTR) (Weiss et al., eds., The molecular biology of tumor viruses: RNA tumor viruses, Cold Spring Harbor Laboratory, (NY 1982)). Moloney murine leukemia virus (MLV) and Rous sarcoma virus (RSV) LTRs contain promoter and enhancer sequences (Jolly et al., Nucleic Acids Res. 11: 1855 (1983); Capecchi et al., In: Enhancer and eukaryotic gene expression, Gulzman and Shenk, eds., pp. 101-102, Cold Spring Harbor Laboratories (NY 1991). Other potent promoters include those derived from cytomegalovirus (CMV) and other wild-type viral promoters.

Promoter and enhancer regions of a number of non-viral promoters have also been described (Schmidt et al., Nature 314: 285 (1985); Rossi and deCrombrugghe, Proc. Natl. Acad. Sci. USA 84: 5590-5594 (1987)). Methods for maintaining and increasing expression of transgenes in quiescent cells include the use of promoters including collagen type I (1 and 2) (Prockop and Kivirikko, N. Eng. J. Med. 311: 376 (1984); Smith and Niles, Biochem. 19: 1820 (1980); de Wet et al., J. Biol. Chem., 258: 14385 (1983)), SV40 and LTR promoters.

According to one embodiment of the invention, the promoter is a constitutive promoter selected from the group consisting of: ubiquitin promoter, CMV promoter, JeT promoter (U.S. Pat. No. 6,555,674), SV40 promoter, Elongation Factor 1 alpha promoter (EF1-alpha), RSV, CAG. Examples of inducible/repressible promoters include: Tet-On, Tet-Off, Rapamycin-inducible promoter, Mx1, Mo-MLV-LTR, progesterone, RU486.

A group of preferred promoters include CAG, CMV, human UbiC, JeT, SV40, RSV, Tet-regulatable promoter, Mo-MLV-LTR, Mx1, Mt1 and EF-1alpha.

In addition to using viral and non-viral promoters to drive transgene expression, an enhancer sequence may be used to increase the level of transgene expression. Enhancers can increase the transcriptional activity not only of their native gene but also of some foreign genes (Armelor, Proc. Natl. Acad. Sci. USA 70: 2702 (1973)). For example, in the present invention collagen enhancer sequences may be used with the collagen promoter 2 (I) to increase transgene expression. In addition, the enhancer element found in SV40 viruses may be used to increase transgene expression. This enhancer sequence consists of a 72 base pair repeat as described by Gruss et al., Proc. Natl. Acad. Sci. USA 78: 943 (1981); Benoist and Chambon, Nature 290: 304 (1981), and Fromm and Berg, J. Mol. Appl. Genetics, 1: 457 (1982), all of which are incorporated by reference herein. This repeat sequence can increase the transcription of many different viral and cellular genes when it is present in series with various promoters (Moreau et al., Nucleic Acids Res. 9: 6047 (1981).

Further expression enhancing sequences include but are not limited to Woodchuck hepatitis virus post-transcriptional regulation element, WPRE, SP163, CMV enhancer, and Chicken [beta]-globin insulator or other insulators.

Cell Lines

In one aspect the invention relates to isolated host cells genetically modified with the vector according to the invention.

The invention also relates to cells suitable for biodelivery of Meteorin via naked or encapsulated cells, which are genetically modified to overexpress Meteorin, and which can be transplanted to the patient to deliver bioactive Meteorin polypeptide locally. Such cells may broadly be referred to as therapeutic cells.

For ex vivo gene therapy, the preferred group of cells includes neuronal cells, neuronal precursor cells, neuronal progenitor cells, neuronal stem cells, human glial stem cells, human precursor cells, stem cells and foetal cells.

For encapsulation the preferred cells include retinal pigmented epithelial cells, including ARPE-19 cells; human immortalised fibroblasts; and human immortalised astrocytes.

The ARPE-19 cell line is a superior platform cell line for encapsulated cell based delivery technology and is also useful for unencapsulated cell based delivery technology. The ARPE-19 cell line is hardy (i.e., the cell line is viable under stringent conditions, such as implantation in the central nervous system or the intra-ocular environment). ARPE-19 cells can be genetically modified to secrete a substance of therapeutic interest. ARPE-19 cells have a relatively long life span. ARPE-19 cells are of human origin. Furthermore, encapsulated ARPE-19 cells have good in vivo device viability. ARPE-19 cells can deliver an efficacious quantity of growth factor. ARPE-19 cells elicit a negligible host immune reaction. Moreover, ARPE-19 cells are non-tumorigenic. Methods for culture and encapsulation of ARPE-19 cells are described in U.S. Pat. No. 6,361,771.

In another embodiment the therapeutic cell line is selected from the group consisting of: human fibroblast cell lines, human astrocyte cell lines, human mesencephalic cell line, and human endothelial cell line, preferably immortalised with TERT, SV40T or vmyc.

Extracellular Matrix

The present invention further comprises culturing Meteorin producing cells in vitro on a extracellular matrix prior to implantation into the mammalian nervous system. The preadhesion of cells to microcarriers prior to implantation is designed to enhance the long-term viability of the transplanted cells and provide long term functional benefit.

Materials of which the extracellular matrix can be comprised include those materials to which cells adhere following in vitro incubation, and on which cells can grow, and which can be implanted into the mammalian body without producing a toxic reaction, or an inflammatory reaction which would destroy the implanted cells or otherwise interfere with their biological or therapeutic activity. Such materials may be synthetic or natural chemical substances, or substances having a biological origin.

The matrix materials include, but are not limited to, glass and other silicon oxides, polystyrene, polypropylene, polyethylene, polyvinylidene fluoride, polyurethane, polyalginate, polysulphone, polyvinyl alcohol, acrylonitrile polymers, polyacrylamide, polycarbonate, polypentent, nylon, amylases, natural and modified gelatin and natural and codified collagen, natural and modified polysaccharides, including dextrans and celluloses (e.g., nitrocellulose), agar, and magnetite. Either resorbable or non-resorbable materials may be used. Also intended are extracellular matrix materials, which are well-known in the art. Extracellular matrix materials may be obtained commercially or prepared by growing cells which secrete such a matrix, removing the secreting cells, and allowing the cells which are to be transplanted to interact with and adhere to the matrix. The matrix material on which the cells to be implanted grow, or with which the cells are mixed, may be an indigenous product of RPE cells. Thus, for example, the matrix material may be extracellular matrix or basement membrane material, which is produced and secreted by RPE cells to be implanted.

To improve cell adhesion, survival and function, the solid matrix may optionally be coated on its external surface with factors known in the art to promote cell adhesion, growth or survival. Such factors include cell adhesion molecules, extracellular matrix, such as, for example, fibronectin, laminin, collagen, elastin, glycosaminoglycans, or proteoglycans or growth factors.

Alternatively, if the solid matrix to which the implanted cells are attached is constructed of porous material, the growth- or survival promoting factor or factors may be incorporated into the matrix material, from which they would be slowly released after implantation in vivo.

The configuration of the support is preferably spherical, as in a bead, but may be cylindrical, elliptical, a flat sheet or strip, a needle or pin shape, and the like. A preferred form of support matrix is a glass bead. Another preferred bead is a polystyrene bead.

Bead sizes may range from about 10 μm to 1 mm in diameter, preferably from about 90 μm to about 150 μm. For a description of various microcarrier beads, see, for example, isher Biotech Source 87-88, Fisher Scientific Co., 1987, pp. 72-75; Sigma Cell Culture Catalog, Sigma Chemical Co., St, Louis, 1991, pp. 162-163; Ventrex Product Catalog, Ventrex Laboratories, 1989; these references are hereby incorporated by reference. The upper limit of the bead's size may be dictated by the bead's stimulation of undesired host reactions, which may interfere with the function of the transplanted cells or cause damage to the surrounding tissue. The upper limit of the bead's size may also be dictated by the method of administration. Such limitations are readily determinable by one of skill in the art.

Biocompatible Capsule

In one aspect the invention relates to a biocompatible capsule containing isolated host cells genetically modified with the vector according to the invention.

Encapsulated cell biodelivery therapy is based on the concept of isolating cells from the recipient host's immune system by surrounding the cells with a semipermeable biocompatible material before implantation within the host. The invention includes a capsule in which cells are encapsulated in an immunoisolatory capsule. Cells are immunoisolated from the host by enclosing them within implantable polymeric capsules formed by a microporous membrane. This approach prevents the cell-to-cell contact between host and implanted tissues, eliminating antigen recognition through direct presentation.

The cell capsule, in the following referred to as the capsule, has a membrane which is tailored to control diffusion of molecules, such as growth factor hormones, neurotransmitters, peptides, antibodies and complements, based on their molecular weight (Lysaght et al., 56 J. Cell Biochem. 196 (1996), Colton, 14 Trends Biotechnol. 158 (1996)). Using encapsulation techniques, cells can be transplanted into a host without immune rejection, either with or without use of immunosuppressive drugs. Useful biocompatible polymer capsules usually contain a core that contains cells, either suspended in a liquid medium or immobilised within an immobilising matrix, and a surrounding or peripheral region of permselective matrix or membrane ("jacket") that does not contain isolated cells, that is biocompatible, and that is sufficient to protect cells in the core from detrimental immunological attack. Encapsulation hinders elements of the immune system from entering the capsule, thereby protecting the encapsulated cells from immune destruction. The semipermeable nature of the capsule membrane also permits the biologically active molecule of interest to easily diffuse from the capsule into the surrounding host tissue and allows nutrients to diffuse easily into the capsule and support the encapsulated cells. The capsule can be made from a biocompatible material. A "biocompatible material" is a material that, after implantation in a host, does not elicit a detrimental host response sufficient to result in the rejection of the capsule or to render it inoperable, for example through degradation. The biocompatible material is relatively impermeable to large molecules, such as components of the host's immune system, but is permeable to small molecules, such as insulin, growth factors, and nutrients, while allowing metabolic waste to be removed. A variety of biocompatible materials are suitable for delivery of growth factors by the composition of the invention. Numerous biocompatible materials are known, having various outer surface morphologies and other mechanical and structural characteristics. Preferably the capsule of this invention will be similar to those described by WO 92/19195, WO 95/05452 or WO 2005/095450, incorporated by reference; or U.S. Pat. Nos. 5,639,275; 5,653,975; 4,892,538; 5,156,844; 5,283,187; or 5,550,050, incorporated by reference.

Such capsules allow for the passage of metabolites, nutrients and therapeutic substances while minimizing the detrimental effects of the host immune system. Components of the biocompatible material may include a surrounding semipermeable membrane and the internal cell-supporting scaffolding. Preferably, the recombinant cells are seeded onto the scaffolding, which is encapsulated by the permselective membrane. The filamentous cell-supporting scaffold may be made from any biocompatible material selected from the group consisting of acrylic, polyester, polyethylene, polypropylene polyacetonitrile, polyethylene teraphthalate, nylon, polyamides, polyurethanes, polybutester, silk, cotton, chitin, carbon, or biocompatible metals. Also, bonded fibre structures can be used for cell implantation (U.S. Pat. No. 5,512,600). Biodegradable polymers include those comprised of poly(lactic acid) PLA, poly(lactic-coglycolic acid) PLGA, and poly(glycolic acid) PGA and their equivalents. Foam scaffolds have been used to provide surfaces onto which transplanted cells may adhere (WO 2005/095450 and WO 98/05304). Woven mesh tubes have been used as vascular grafts (WO 99/52573). Additionally, the core can be composed of an immobilizing matrix formed from a hydrogel, which stabilizes the position of the cells. A hydrogel is a 3-dimensional network of cross-linked hydrophilic polymers in the form of a gel, substantially composed of water.

The jacket preferably has a molecular weight cutoff, defined as that molecular weight, where the membrane (the jacket) will reject 90% of the solutes, of less than 1000 kD, more preferably between 50-700 kD, more preferably between 70-300 kD, more preferably between 70-150 kD, such as between 70 and 130 kD. The molecular weight cutoff should be selected to ensure that the bioactive molecule can escape from the capsule while protecting the encapsulated cells from the immune system of the patient.

The thickness of the jacket typically lies in the range of 2 to 200 microns, more preferably from 50 to 150 microns. The jacket should have a thickness to give the capsule sufficient strength to keep the cells encapsulated and should with this in mind be kept as thin as possible to take up as little space as possible.

Various polymers and polymer blends can be used to manufacture the surrounding semipermeable membrane, including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly(acrylonitrile/covinyl chloride), as well as derivatives, copolymers and mixtures thereof. Preferably, the surrounding semipermeable membrane is a biocompatible semipermeable hollow fibre membrane. Such membranes, and methods of making them are disclosed by U.S. Pat. Nos. 5,284,761 and 5,158,881. The surrounding semipermeable membrane may be formed from a polyether sulfone hollow fibre, such as those described by U.S. Pat. Nos. 4,976,859 or 4,968,733. An alternate surrounding semipermeable membrane material is poly(acrylonitrile/covinyl chloride) (Pan-PVC).

The capsule can be any configuration appropriate for maintaining biological activity and providing access for delivery of the product or function, including for example, cylindrical, rectangular, disk-shaped, patch-shaped, ovoid, stellate, or spherical. Moreover, the capsule can be coiled or wrapped into a mesh-like or nested structure. If the capsule is to be retrieved after it is implanted, configurations, which tend to lead to migration of the capsules from the site of implantation, such as spherical capsules small enough to travel in the recipient host's blood vessels, are not preferred. Certain shapes, such as rectangles, patches, disks, cylinders, and flat sheets offer greater structural integrity and are preferable where retrieval is desired. A particularly preferred shape is cylinder-shaped as such a shape is easily produced from hollow fibres which can be produced industrially.

A macrocapsule in the present context is a capsule having a volume of at least 1 µL, such as from 1 to 10 µL.

When macrocapsules are used, preferably at least $10^3$ cells are encapsulated, such as between $10^3$ and $10^8$ cells are encapsulated, most preferably $10^5$ to $10^7$ cells are encapsulated in each device. Of course, the number of cells in each capsule depends on the size of the capsule. As a rule of thumb, in a capsule with foam (described below) the present inventors have found that loading between 10,000 and 100,000 cells per µL of capsule (volume calculated as the internal volume including foam) results in a good filling of the capsule, more preferably from 25,000 to 50,000 cells per µL, more preferably from 30,000 to 40,000 cells per µL. The number of cells to be loaded also depends on the size of the cells.

Dosage may be controlled by varying the dimensions (length, diameter) of the capsule and/or by implanting a fewer or greater number of capsules, preferably between 1 and 10 capsules per patient.

The scaffolding may be coated with extracellular matrix (ECM) molecules. Suitable examples of extracellular matrix molecules include, for example, collagen, laminin, and fibronectin. The surface of the scaffolding may also be modified by treating with plasma irradiation to impart charge to enhance adhesion of cells.

Any suitable method of sealing the capsules may be used, including the use of polymer adhesives or crimping, knotting and heat sealing. In addition, any suitable "dry" sealing method can also be used, as described, e.g., in U.S. Pat. No. 5,653,687.

The encapsulated cell devices are implanted according to known techniques. Many implantation sites are contemplated for the devices and methods of this invention. These implantation sites include, but are not limited to, the central nervous system, including the brain, spinal cord (see, U.S. Pat. Nos. 5,106,627, 5,156,844, and 5,554,148), and the aqueous and vitreous humors of the eye (see WO 97/34586).

The disclosed capsule may include an integral tether that extends from the capsule and which is of a length sufficient to reach at least from the treatment site to the proximity of the insertion site thereby facilitating fixation of the capsule at the insertion site, e.g. to the outer surface of the skull. The insertion site is subsequently covered by skin.

To facilitate removal of the capsule from the tissue, e.g. when the treatment comes to an end, or if the capsule must be replaced, the transition between the capsule and the tether could be smooth and without projections of any kind, or the dimension could be increased from the capsule towards the tether. This, obviously, creates an edge between the two parts but since the relatively small capsule forms the distal end of the therapy system, i.e. the end which is towards the body, ancillary damage may be prevented during removal of the capsule. If the capsule and the tether are tubular with circular cross sectional shapes, the radial size of the capsule may therefore preferably be smaller than the radial size of the tether, and the capsule and tether may preferably be joined coaxially to each other. Preferably the capsule of this invention will be similar in design to those described by WO 2006/122551 and WO 2005/095450.

Capsules may be filled by using a syringe or alternatively, automated or semi-automated filling may be used as described in WO2007/048413.

EXAMPLES

Example 1

Protein Purification

Mouse meteorin (Uniprot Accession # Q8C1Q4; SEQ ID NO:5) (aa22-291 (SEQ ID NO:6) with a signal peptide from hCD33) was cloned into an expression vector. The vector was transfected into the NS0 mouse myeloma cell line by electroporation.

Stable clones were isolated and screened for expression of mMeteorin by Western analysis using GtxmMETRN polyclonal antibody (AF3475). Conditioned medium from cultures containing mouse Meteorin was concentrated, supplemented with 20 mM MOPS, the pH was adjusted to 6.5, and filtered through a 0.2 um filter. The sample was applied to an anion exchange chromatography resin, equilibrated in 20 mM MOPS, 0.1 M NaCl, pH 6.5. The fractions containing mouse Meteorin were supplemented with 2 M NaCl, the pH was adjusted to 7.0, and then applied to a phenyl sepharose resin. Bound proteins were eluted with a decreasing gradient of NaCl. Fractions enriched in mouse Meteorin were pooled, concentrated and loaded onto a Superdex gel filtration column and then equilibrated in PBS. Mouse Meteorin eluted as an approximately 30 kDa molecular weight protein. Fractions of interest were pooled, concentrated, dialyzed against PBS and stored at –80 C.

Example 2

Photochemically Induced Sciatic Nerve Injury

The effect of systemically (sc) administered Meteorin was investigated in photochemically induced sciatic nerve injured rats known to develop allodynia to both mechanical and cold stimulation within one week after injury (Kupers, R., Yu, W., Persson, J. K., Xu, X. J., and Wiesenfeld-Hallin, Z. (1998); Photochemically-induced ischemia of the rat sciatic nerve produces a dose-dependent and highly reproducible mechanical, heat and cold allodynia, and signs of spontaneous pain. Pain 76, 45-59). Briefly, after unilateral photoinduced injury of the sciatic nerve, animals were randomly divided into four groups (n=8 per group) and injected with saline as negative control or Meteorin at three different concentrations (0.05, 0.2 and 0.8 mg/kg). Each rat received six injections over a two week period starting after seven days when a stable allodynia was developed. Behavioral assessments were conducted before each injection during the treatment period and for two additional weeks.

From FIG. 1 it is evident that saline and Meteorin at the low dose (0.05 mg/kg) did not affect the response to mechanical stimulation of the ipsilateral hind paw. 0.2 mg/kg Meteorin reduced mechanical allodynia moderately but this group was not statistically different from the saline control group. In contrast, repeated injection of 0.8 mg/kg Meteorin produced a significant and marked alleviation of mechanical allodynia. After treatment cessation on Day 21, this group stayed significantly different from vehicle for at least a week. Over time, mechanical allodynia was gradually reestablished.

Figure 2:
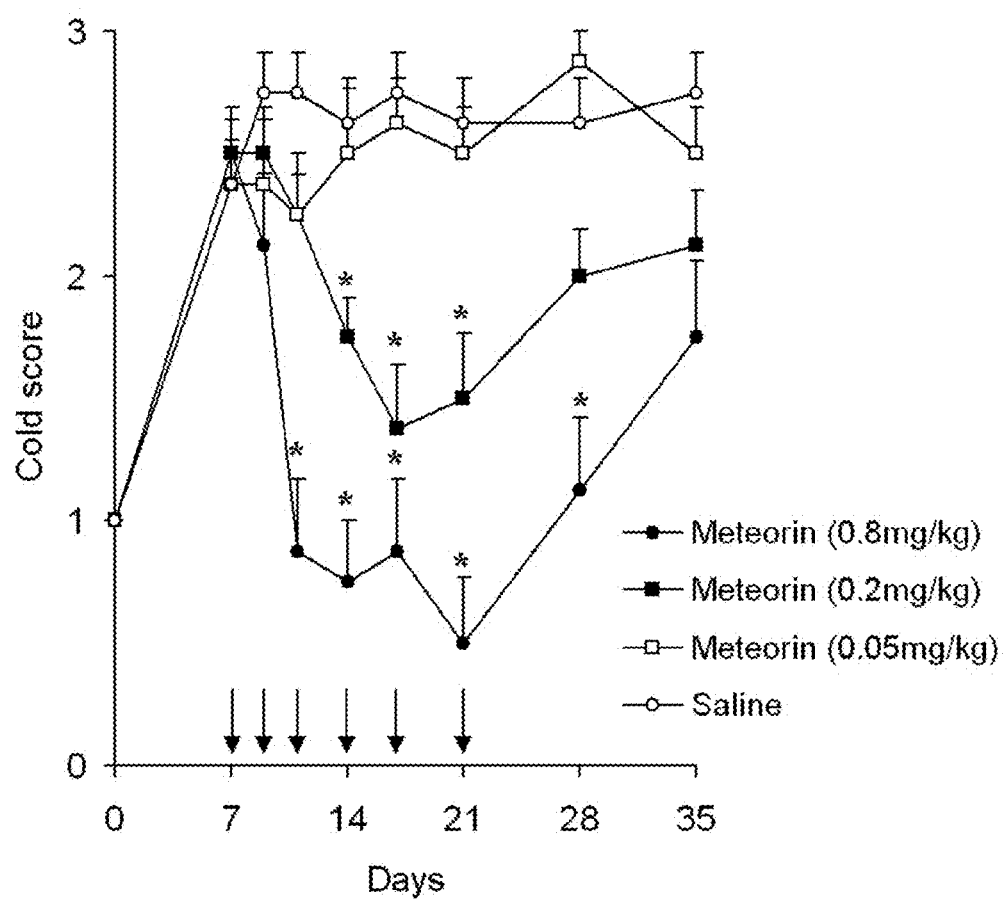
FIG. 2. Ipsilateral hind paw response score to cold stimulation following sciatic nerve injury. 0 is no response, 1 corresponds to a startle-like response seen in normal rats whereas 2 and 3 indicate mild and severe pain reactions. Note that Meteorin treatment dose-dependently alleviates cold allodynia. Arrows indicate treatment time points. Scoring was done blinded and data are shown as mean±SEM. *$p<0.05$.

The response to cold was evaluated by briefly spraying ethyl chloride on the plantar surface of the hind paw and scoring animal behavior accordingly. FIG. 2 shows that treatment with 0.8 mg/kg Meteorin potently alleviated cold allodynia stimulation and that the 0.2 mg/kg also has a significant positive effect. After treatment cessation, the group treated with 0.8 mg/kg Meteorin stayed significantly different from vehicle for at least a week and there was a trend towards improvement even after two weeks. The cold allodynia gradually reestablished over time but this was not complete at the end of the experiment. There was no effect of 0.05 mg/kg Meteorin which was similar to the control group thoughout the study.

Figure 3:
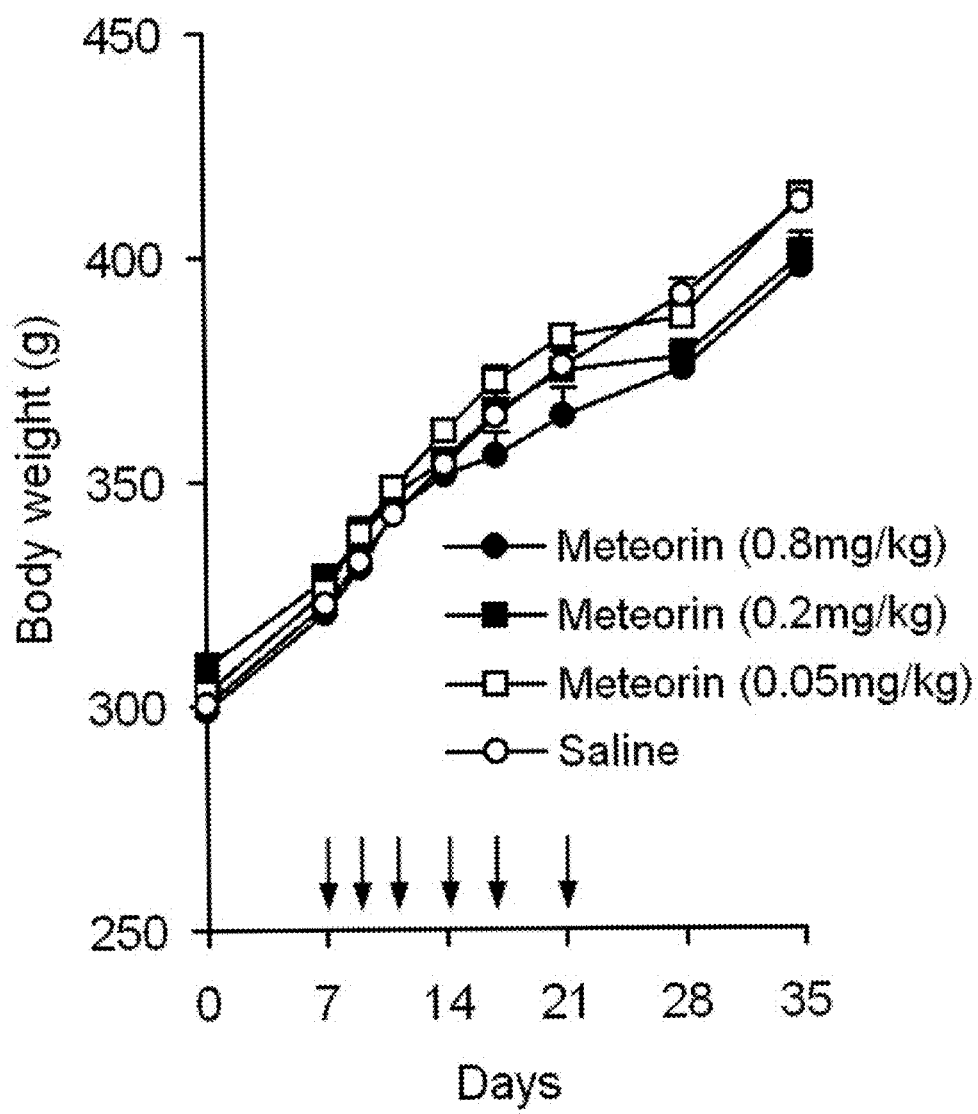
FIG. 3. Body weight changes in sciatic nerve injured rats. All animals gained weight normally throughout the study. Arrows indicate treatment time points. Scoring was done blinded and data are shown as mean±SEM. *$p<0.05$.
Figure 4:
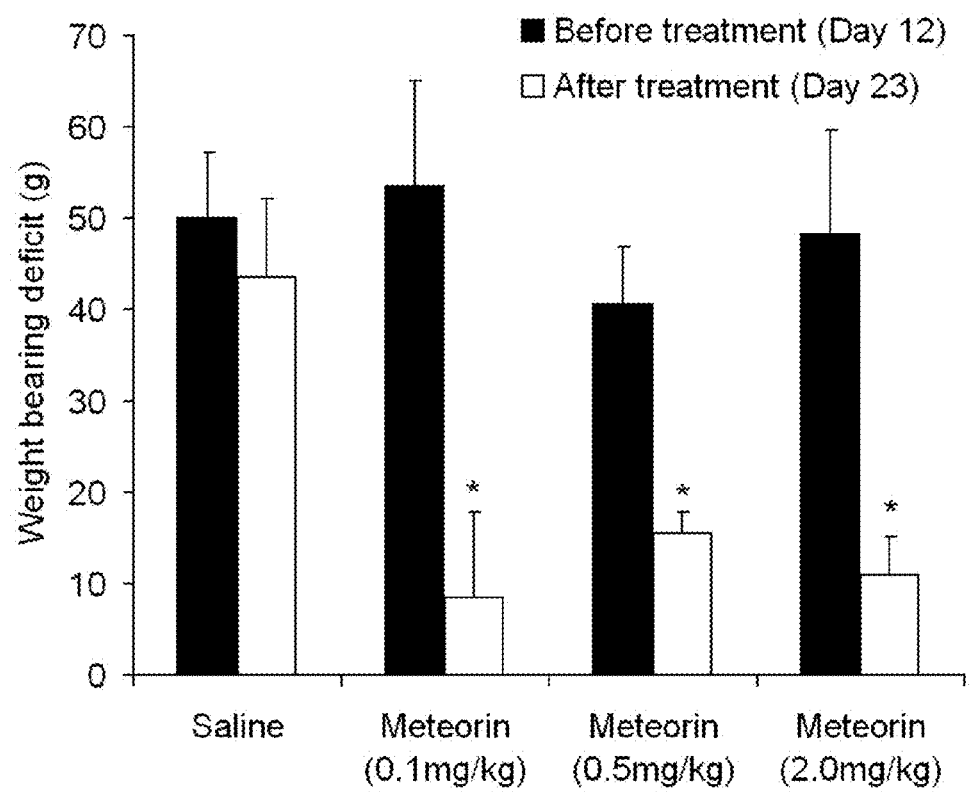
FIG. 4. Weight bearing deficits in rats after CCI (Chronic Constriction Injury). An incapacitance meter was used to assess the downward force applied by each hindlimb. Before surgery, there was no deficit as all animals carried weight equally on both hind-limbs. After 12 days, immediately before treatment begins, ~50 g more was put on the contralateral limp compared to the ipsilateral limp. Note that Meteorin treatment alleviates the weight bearing deficits. Scoring was done blinded and data are shown as mean±SEM. *$p<0.05$.
Figure 5:
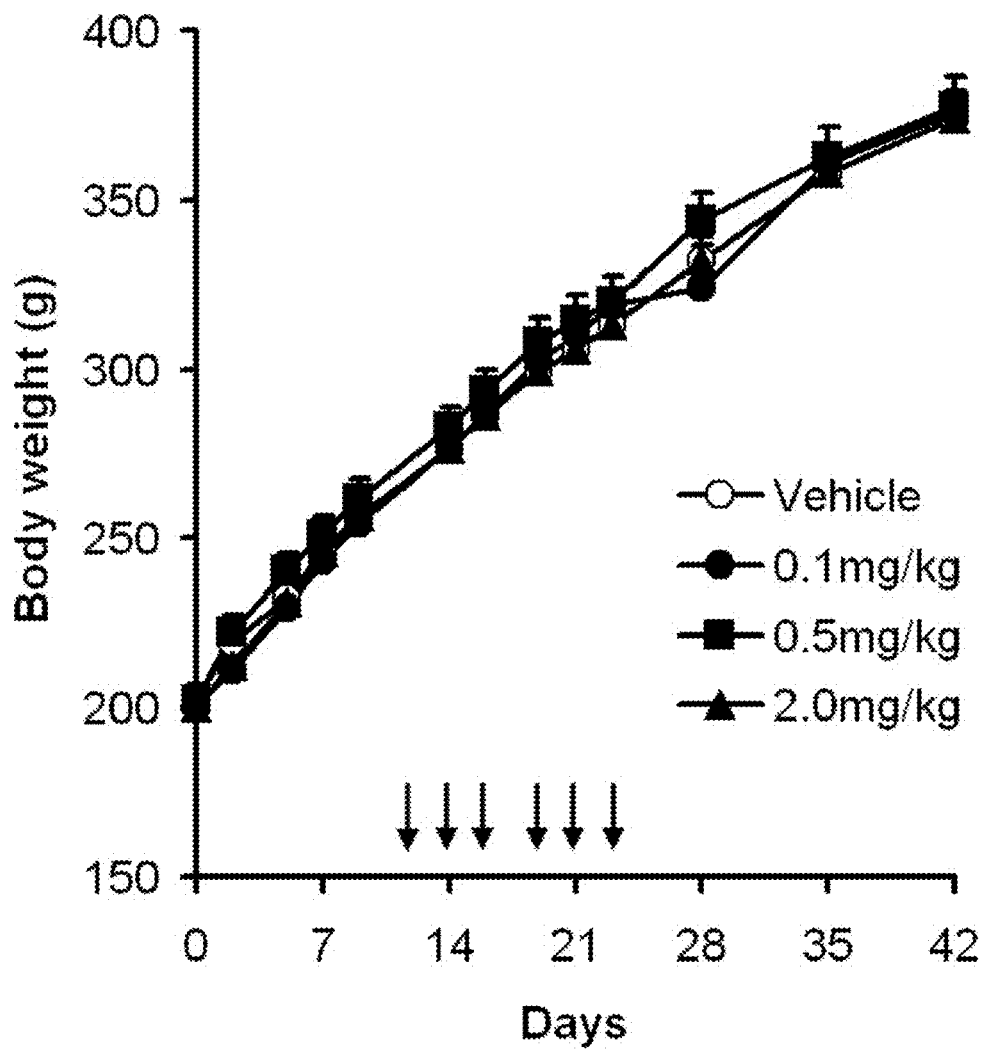
FIG. 5. Body weight changes in CCI rats. All animals gained weight normally throughout the study. Arrows indicate treatment time points. Scoring was done blinded and data are shown as mean±SEM. *$p<0.05$.

Importantly, all animals gained weight normally throughout the study and no side effects were observed (FIG. 3).

In conclusion, Meteorin dose-dependently reduced both mechanical and cold allodynia and the effect lasted for at least a week after treatment cessation. Two weeks after treatment cessation, hypersensivity seemed to gradually reestablish. No side effects were observed.

Example 3

Chronic Constriction Injury (CCI)

The effect of Meteorin was further investigated in the well established chronic constriction injury (CCI) model (Bennett, G. J., and Xie, Y. K. (1988); A peripheral mononeuropathy in rat that produces disorders of pain sensation like those seen in man. Pain 33, 87-107). Briefly, twelve days after injury, when a stable mechanical allodynia was established, animals received six subcutaneous injections of Meteorin (0.1, 0.5, 2.0 mg/kg) or vehicle distributed over the next two weeks (n=7-8 per group). Animal behavior was followed throughout the study up to three weeks after the last injection.

Weight bearing was evaluated immediately before and after treatment as a surrogate maker for spontaneous pain. Prior to treatment (Day 12), all groups had a side-to-side deficit of approximately 50 g which was reduced to 10-15 g for the groups treated with Meteorin. After treatment cessation, the effect was gradually reduced and there was no significant difference between the groups after three weeks.

Mechanical allodynia was also evaluated in the CCI animals. The average baseline paw withdrawal threshold to mechanical stimulation with calibrated von Frey hairs was 15 g which was gradually reduced to 2 g on Day 12 where treatment began. While the vehicle group remained hypersensitive throughout the study (−2 g), Meteorin effectively alleviated mechanical allodynia at all doses tested (8-11 g). After treatment cessation, animals in the Meteorin treatment group remained significantly different from the control group for approximately a week but allodynia was gradually reestablished and there was no difference between groups after three weeks. To evaluate the magnitude of the effect, animals in the control group were given a high dose of Gabapentin (200 mg/kg) for comparison. One hour after Gabapentin treatment the threshold to mechanical stimulation was 9.7±1.9 g compared to 1.9±0.7 g before treatment. It is clear that Meteorin and Gabapentin are similarly effective but importantly while Gabapentin is an analgesic, Meteorin has long lasting and potentially disease modifying effects.

Meteorin injections did not cause weight loss or general behavioral differences between control and treated animals.

Example 4

Chronic Constriction Injury (CCI)

Objective

This study was designed to investigate the efficacy of sub cutaneously (s.c) administered recombinant Meteorin to alleviating allodynia and spontaneous pain in rats produced by chronic constriction injury (CCI) (Bennett and Xie, "A peripheral mononeuropathy in rat that produces disorders of pain sensation like those seen in man", 1988, Pain 33; p. 87-107).

Methods

Recombinant Meteorin. Recombinant mouse Meteorin (Uniprot Accession # Q8C1Q4) was produced as described elsewhere in this application.

Surgery: 30 male Sprague-Dawley rats weighing 250-280 g underwent surgery to produce a chronic constriction of the left sciatic nerve using four loose ligatures of 4-0 chromic gut suture (CCI Model) (Bennett and Xie, "A peripheral mononeuropathy in rat that produces disorders of pain sensation like those seen in man", 1988, Pain 33; p. 87-107). Rats were anesthetized via inhalation of isofluorane gas. Rats received a skin incision just caudal to the biceps femoris at mid-thigh level on the left hindlimb. A small incision was then made into the underlying muscle layer and separated gently using hemostats with care taken not to disturb the sciatic nerve. The sciatic nerve was then identified, freed of adhering tissue and slightly elevated using 45° angle forceps. Four pieces of 4-0 chromic gut suture material (previously washed in sterile saline) were brought under the nerve and then each loosely tied around the nerve into a square knot. The knots were spaced 1 mm apart. These loose ligatures allowed for a chronic constriction of the nerve without cutting off blood supply. Muscle layers were sutured closed with 4-0 vicryl suture and skin closed with wound clips.

Grouping and Behavioral Analysis: At day 0 of the experiment, all rats were tested for mechanical allodynia using Von Frey Filaments, thermal allodynia using the Hargreaves' method and weight bearing on hind limbs using an incapacitance meter. 24 rats were selected to continue in the study and later divided into four treatment groups (n=6). Animals were injected five times s.c. with either vehicle, 0.1, 0.5 or 1.8 mg/kg of Meteorin protein on post surgical days 10, 12, 14, 17 and 19. Animals were further tested for mechanical and thermal allodynia as well as incapacitance at days 10, 12, 14, 17, 19, 21, 26, 32 and 39 post surgery. Importantly, behavioral analysis was done prior to injection of Meteorin in order to exclude immediate analgesic effects and to focus on long lasting potentially disease modifying effects. Animals were observed and body weight followed throughout the study. The experimenter was blind to treatment condition and no animals were removed from the study.

Assay for Meteorin in serum: Following behavioral testing on post-surgical day 39, animals were dosed at 0.1, 0.5 and 2 mg/kg of Meteorin and rat serum samples were collected at 2, 6, 24 hr following drug administration. Serum was also collected from non-treated control rats. There were two rats for each time point. All rat serum samples were assayed by mouse Meteorin ELISA (R&D Systems, DY3475).

Results

Figure 7:
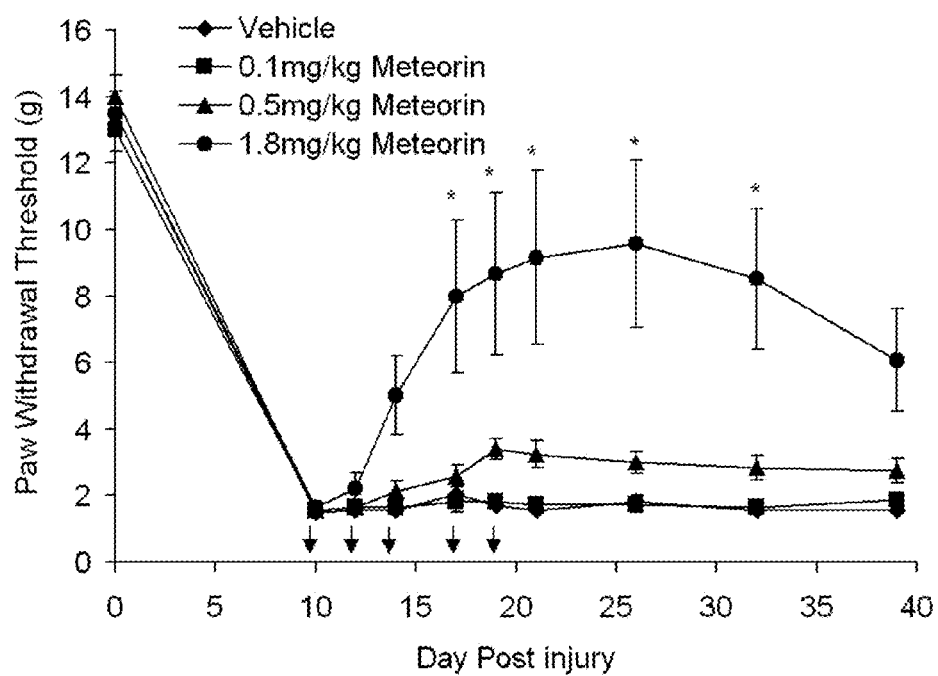
FIG. 7. Effect of Meteorin on mechanical hypersensitivity in CCI rats. Arrows indicate treatment days where animals were systemically injected with 0.1 mg/kg, 0.5 mg/kg or 1.8 mg/kg recombinant Meteorin or with vehicle as negative control. Rats were examined for altered nociception using von Frey filaments and results expressed as means±SEM. * denotes a significant difference ($p<0.05$) compared to vehicle treated animals.

Experimental allodynia and spontaneous pain were induced in rats by CCI (Bennett and Xie, 1988) and tactile allodynia evaluated using Von Frey Hairs (FIG. 7). Rats had a baseline withdrawal threshold of approximately 15 g which was reduced to 1.5 g 10 days after the CCI. It is evident that treatment with Meteorin rapidly reduced the allodynia and the force withstood by 1.8 mg/kg of Meteorin treated rats were significant at day 17, 19, 21, 26 and 32 compared to vehicle treated rats. As such, the significant difference was maintained at least 13 days after treatment cessation and a trend towards reduced allodynia was also observed after 20 days. Most animals in the group treated with 1.8 mg/kg of Meteorin reverted to 15 g but one animal did not respond which explains the increased standard error in this particular group.

With respect to thermal sensivity (FIG. 8), rats had a baseline withdrawal latency of 16.5 seconds which was reduced to approximately 7 seconds 10 days after CCI signifying a thermal allodynia. Vehicle treated animals stayed hypersensitive throughout the study while treatment with Meteorin at 1.8 mg/kg rapidly resulted in a significant decrease in paw withdrawal latency from day 14 which lasted for the rest of the experiment including at least three weeks after treatment cessation. Interestingly, instead of going back to the allodynia level of the vehicle group, the paw withdrawal latency levelled out at 10.5 seconds for this Meteorin group. The 0.5 mg/kg dose of Meteorin also resulted in decreased paw withdrawal latency becoming significant at days 19 and 21. There was also a trend towards decreased allodynia with 0.1 mg/kg Meteorin although this did not reach statistically significant levels. In summary, Meteorin dose-dependently reduced thermal allodynia with significant effects in the treatment period and beyond.

Figure 9:
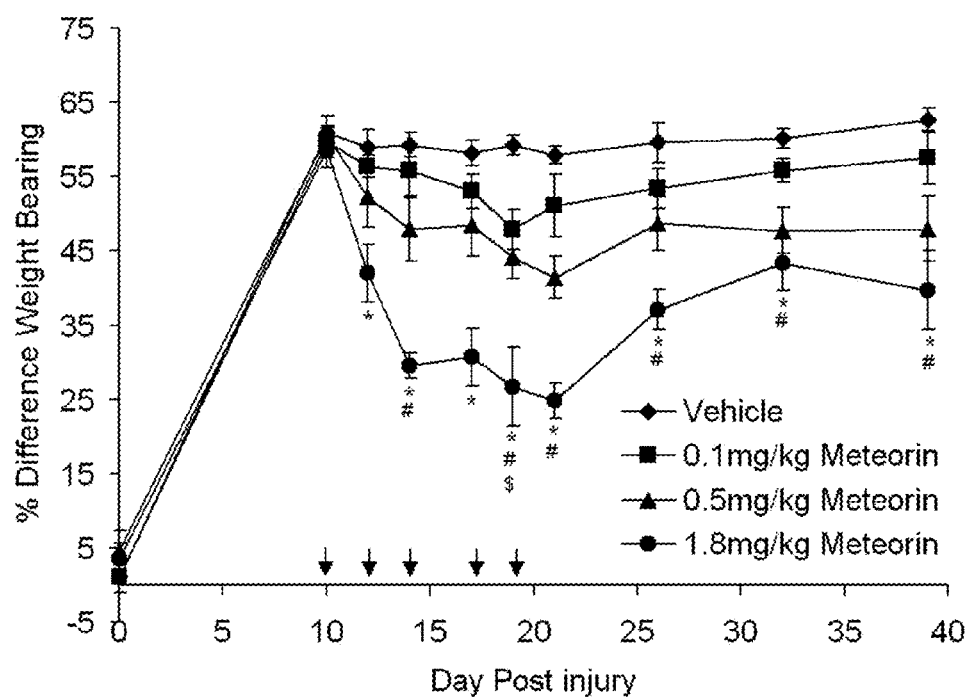
FIG. 9. Effect of Meteorin on differential weight bearing in CCI rats. Arrows indicate treatment days where animals were systemically injected with 0.1 mg/kg, 0.5 mg/kg or 1.8 mg/kg recombinant Meteorin or with vehicle as negative control. Differential weight bearing between the injured and non-injured limb was determined using an incapacitance meter and expressed as % difference. Data are shown as means±SEM. * denotes a significant difference ($p<0.05$) between 1.8 mg/kg Meteorin and vehicle treated animals. # denotes a significant difference ($p<0.05$) between 0.5 mg/kg Meteorin and vehicle treated animals. $ denotes a significant difference ($p<0.05$) between 0.1 mg/kg Meteorin and vehicle treated animals. Note that Meteorin significantly and dose-dependently reduced weight bearing deficits.

At the post-surgical baseline screen, rats distributed equal weight between both of their hindlimbs (FIG. 9). However, following the CCI injury there was approximately 60% less weight applied to the ipsilateral hindlimb which is taken as a surrogate marker for spontaneous pain. The weight bearing deficit of 60% was maintained in the vehicle group throughout the study. In contrast, both 0.5 and 1.8 mg/kg Meteorin quickly reduced the weight bearing deficit and in both cases did the positive effect remain significantly improved for at least three weeks after treatment cessation. A statistically significant effect was also seen with the low dose Meteorin at day 19. Generally, from day 26 to the end of the experiment, the weight bearing deficit settled in all Meteorin treated groups at steady levels lower than the vehicle group. Where the vehicle control group remained above 60%, the average weight bearing deficits for the Meteorin treated groups settled around 55%, 48% and 40% respectively for 0.1, 0.5 and 1.8 mg/kg Meteorin.

Figure 10:
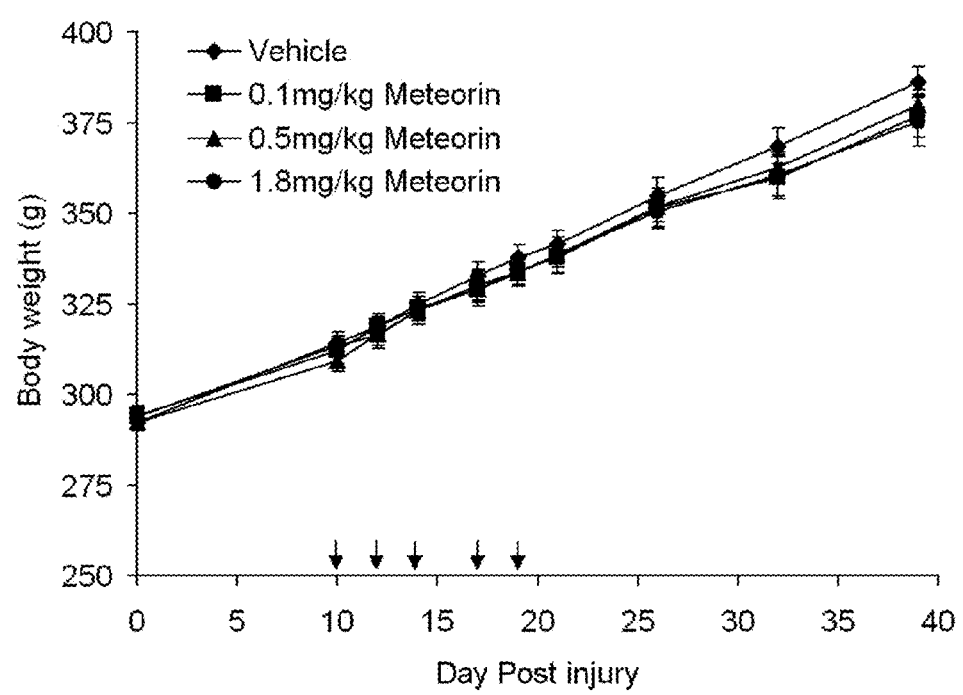
FIG. 10. Animal body weight during the CCI study. Arrows indicate treatment days where animals were systemically injected with 0.1 mg/kg, 0.5 mg/kg or 1.8 mg/kg recombinant Meteorin or with vehicle as negative control. There were no changes in body weight in the Meteorin treated groups compared to vehicle.

No immediate side effects were observed and all animals gained weight normally throughout the study (FIG. 10).

Figure 8:
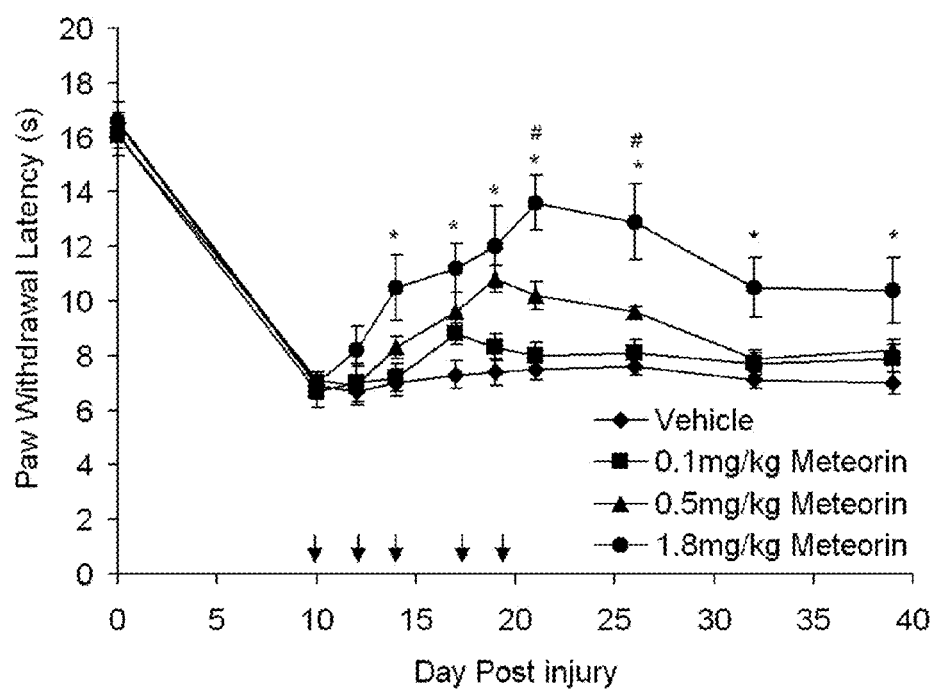
FIG. 8. Effect of Meteorin on thermal hypersensitivity in CCI rats. Arrows indicate treatment days where animals were systemically injected with 0.1 mg/kg, 0.5 mg/kg or 1.8 mg/kg recombinant Meteorin or with vehicle as negative control. A Hargreaves device was used to assess thermal withdrawal latency and results expressed as means±SEM. * denotes a significant difference ($p<0.05$) between 1.8 mg/kg Meteorin and vehicle treated animals. # denotes a significant difference ($p<0.05$) between 0.5 mg/kg Meteorin and vehicle treated animals. Note that Meteorin significantly and dose-dependently reduced thermal allodynia.

Following the last behavioral test on Day 39, animals were dosed with 0.1, 0.5 and 1.8 mg/kg Meteorin and serum samples collected 2, 6 and 24 hours later for pharmacokinetic evaluation (FIG. 11). Meteorin was barely detectable in serum after injection of 0.1 mg/kg but a good relationship between dose and serum concentration was observed between the two higher doses. It is furthermore clear from FIG. 11 that Meteorin is no longer detectable in serum 24 hours after injection. In relation to this, it is interesting that the observed beneficial effects last for several weeks after the last injection where Meteorin is no longer present in serum (FIGS. 7, 8 and 9). Also, instead of returning to the hypersensitive base line level, Meteorin treatment leads to a new less hypersensitive level. Taken all together, it is likely that Meteorin has disease modifying properties. As such, the long lasting effect may reflect normalization or restoration of neuronal function.

Conclusion

Administration of Meteorin to animals that were surgically prepared to exhibit a allodynia and spontaneous pain-like syndrome resulted in profound reduction of allodynia and spontaneous pain inferred by a reduction in both thermal and tactile allodynia and a normalization of differential weight bearing. Even though Meteorin is absent from serum 24 hours after injections, the positive effects last for several weeks thereby demonstrating disease modifying properties.

Example 5

Photochemically Induced Sciatic Nerve Injury, Intrathecal Administration

Methods

Surgery. Male Sprague-Dawley rats (Harlan, The Netherlands) weighing 380-450 g were fitted with a chronic intrathecal catheter with the tip at the lumbar enlargement (Storkson, R. V., Kjorsvik, A., Tjolsen, A., and Hole, K. (1996). Lumbar catheterization of the spinal subarachnoid space in the rat. J. Neurosci. Methods 65, 167-172). Three to five days after cathether implantation, ischemic sciatic nerve injury was produced using a photochemical method (Kupers, R., Yu, W., Persson, J. K., Xu, X. J., and Wiesenfeld-Hallin, Z. (1998); Pain 76, 45-59). Briefly, under general anesthesia (chloral hydrate 300 mg/kg), the left sciatic nerve was exposed at mid-thigh level and irradiated for 1.5 min with an argon laser operating at 514 nm at an average power of 0.17 W. Erythrosin B (32.5 mg/kg dissolved in 0.9% saline) was injected intravenously through the tail vein just prior to irradiation. This operation leads to a highly reproducible hypersensitivity within 7 days.

Evaluation of allodynia. For evaluation of mechanical allodynia, a set of calibrated nylon monofilaments (von Frey hairs, Stoelting, IL) was applied to the glabrous skin of the paws with increasing force until the animal withdraws the limb. Each monofilament was applied 5 times and withdrawal threshold was determined as the force at which the animal withdraws the paw from at least 3 out of 5 consecutive stimuli. The response to cold was tested with ethyl chloride, which was briefly (<1 s) sprayed on the plantar surface of the hind paw. The response was scored as the following: 0=no response, 1=startle-like response, no hindpaw withdrawal (normal), 2=brief withdrawal of the stimulated hindpaw (mild pain), 3=sustained or repeated withdrawal of the stimulated hindpaw, brief licking or shaking (severe pain). All tests were performed by an experimenter who was blind with respect to the experimental conditions.

Experimental setup. Baseline responses were evaluated after catheter implantation and again before sciatic nerve irradiation. Rats that developed allodynia to mechanical and cold stimulation 7 days after nerve injury were randomly divided into four groups (N=8) which were given vehicle as negative control and three doses of recombinant Meteorin (0.5, 2 and 6 ug) at a volume of 10 µl intrathecally. Each rat received six injections over a two week period (on day 7, 9, 11, 14, 16 and 18 counting from the time of nerve injury). Behavioral testing was conducted prior to intrathecal injection on respective treatment days and furthermore on days 21, 25, 28 and 35 following treatment cessation.

Results

Figure 12:
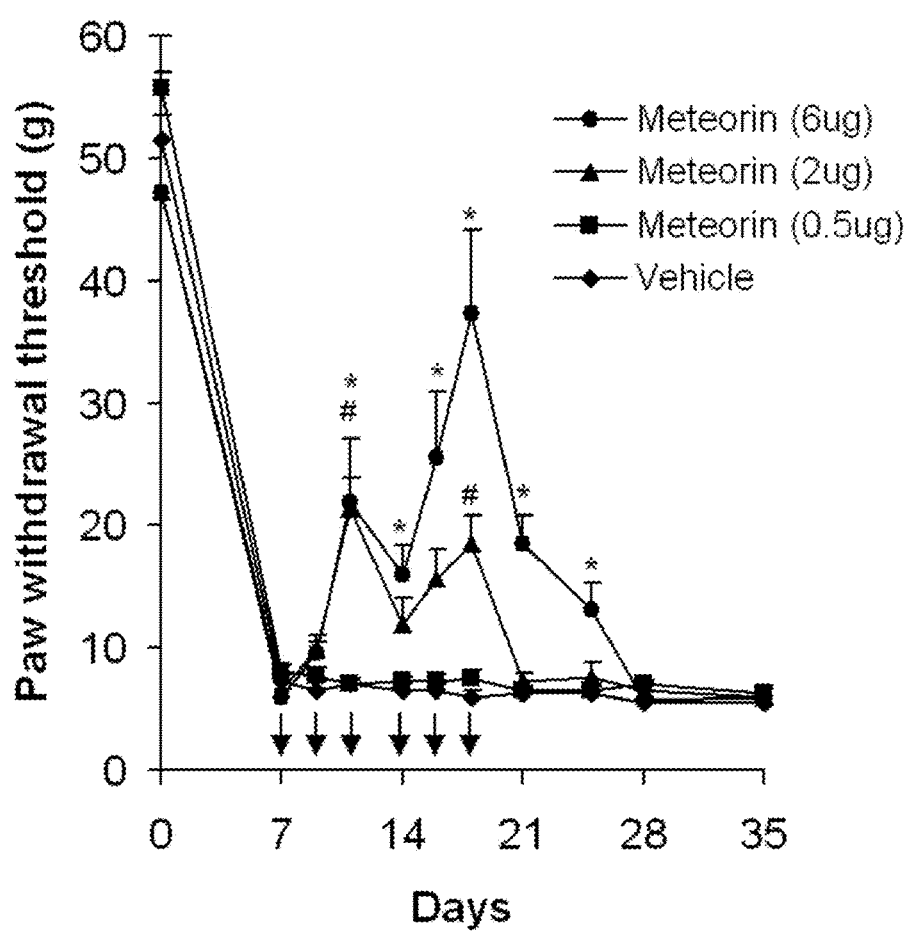
FIG. 12. Effect of Meteorin on paw withdrawal threshold to mechanical stimulation following ischemic sciatic nerve injury. Arrows indicate time points for intrathecal injection. Data are shown as means±SEM. * indicates a significant difference ($p<0.05$) between vehicle and 6 µg Meteorin whereas # indicates a significant difference ($p<0.05$) between vehicle and 2 µg Meteorin.

As seen in FIG. 12, the baseline paw withdrawal threshold to mechanical stimulation was about 50 g. 7 days after photochemically induced sciatic nerve injury, rats developed significant mechanical allodynia evident as a reduced paw withdrawal threshold of approximately 8 g. Rats were then randomly divided into four groups subsequently receiving either vehicle or Meteorin as six intrathecal injections in the space of two weeks. With respect to Meteorin, rats received 0.5 µg, 2 µg or 6 µg. It is clear that intrathecal injection of Meteorin significantly and dose-dependently reduced mechanical allodynia (FIG. 12). The mechanical allodynia was gradually reestablished within a week after treatment cessation. Intrathecal injection of vehicle did not affect the mechanical hypersensitivity throughout the experiment.

Figure 13:
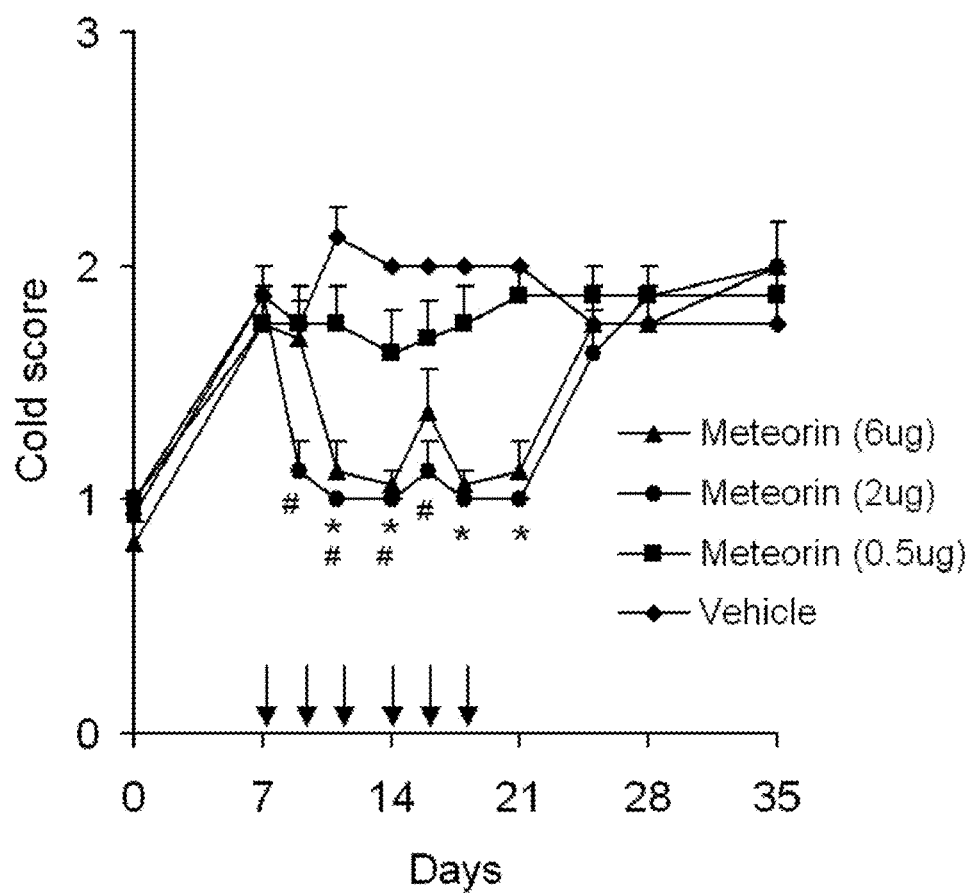
FIG. 13. Effect of Meteorin on response to cold stimulation following ischemic sciatic nerve injury. Arrows indicate time points for intrathecal injection. Data are shown as means±SEM. * indicates a significant difference ($p<0.05$) between vehicle and 6 µg Meteorin whereas # indicates a significant difference ($p<0.05$) between vehicle and 2 µg Meteorin

As seen in FIG. 13, the baseline cold response is 1 corresponding to a normal startle-like response. 7 days after photochemically induced sciatic nerve injury, rats developed a marked cold allodynia evident as a mild pain reaction. Treatment with 2 µg and 6 µg Meteorin quickly reversed the cold allodynia and animals had a near normal response to cold in the treatment period. A significant positive effect of 6 µg Meteorin was also observed three days after treatment cessation. However, cold allodynia was fully reestablished a week after the treatment ended. Vehicle had no effect on cold allodynia.

Conclusion

Repeated intrathecal injection of Meteorin significantly reduces mechanical and cold allodynia in rats after ischemic sciatic nerve injury.

Example 6

Sequence Listing

5  SEQ ID NO 1: human Meteorin cDNA
   SEQ ID NO 2: human Meteorin full length amino acid sequence
   SEQ ID NO 3: human Meteorin amino acid sequence without signal peptide
10 SEQ ID NO 4: mouse Meteorin cDNA
   SEQ ID NO 5: mouse Meteorin full length amino acid sequence
   SEQ ID NO 6: mouse Meteorin amino acid sequence without signal peptide
15 SEQ ID NO 7: rat Meteorin cDNA
   SEQ ID NO 8: rat Meteorin full length amino acid sequence
   SEQ ID NO 9: rat Meteorin amino acid sequence without signal peptide
20 SEQ ID NO 10: human codon optimized DNA sequence
   SEQ ID NO 11: mature Meteorin, consensus sequence

```
Human Meteorin cDNA (1109 bp; CDS = 118-999)
>gi|34147349|ref|NM_024042.2| Homo sapiens hypothetical protein
MGC2601 (MGC2601), mRNA
                                                            (SEQ ID NO 1)
GCTTCGCCGGGGCCGGGCGGCCGGCGCCCCCGGCTGCTCCCGCCGCCGCCCGGACCCGCGCCCCGCCGGG

GCAGCGGTGGTGAGAGCCCCGACTCCCCGGACGCCGCCCGCCGTGCCATGGGGTTCCCGGCCGCGGCGCT

GCTCTGCGCGCTGTGCTGCGGCCTCCTGGCCCCGGCTGCCCGCGCCGGCTACTCCGAGGAGCGCTGCAGC

TGGAGGGGCAGCGGCCTCACCCAGGAGCCCGGCAGCGTGGGGCAGCTGGCCCTGGCCTGTGCGGAGGGCG

CGGTTGAGTGGCTGTACCCGGCTGGGGCGCTGCGCCTGACCCTGGGCGGCCCCGATCCCAGAGCGCGGCC

CGGCATCGCCTGTCTGCGGCCGGTGCGGCCCTTCGCGGGCGCCCAGGTCTTCGCGGAGCGCGCAGGGGGC

GCCCTGGAGCTGCTGCTGGCCGAGGGCCCGGGCCCGGCAGGGGGCCGCTGCGTGCGCTGGGGTCCCCGCG

AGCGCCGGGCCCTCTTCCTGCAGGCCACGCCGCACCAGGACATCAGCCGCCGCGTGGCCGCCTTCCGCTT

TGAGCTGCGCGAGGACGGGCGCCCCGAGCTGCCCCCGCAGGCCCACGGTCTCGGCGTAGACGGTGCCTGC

AGGCCCTGCAGCGACGCTGAGCTGCTCCTGGCCGCATGCACCAGCGACTTCGTAATTCACGGGATCATCC

ATGGGGTCACCCATGACGTGGAGCTGCAGGAGTCTGTCATCACTGTGGTGGCCGCCCGTGTCCTCCGCCA

GACACCGCCGCTGTTCCAGGCGGGGCGATCCGGGGACCAGGGGCTGACCTCCATTCGTACCCCACTGCGC

TGTGGCGTCCACCCGGGCCCAGGCACCTTCCTCTTCATGGGCTGGAGCCGCTTTGGGGAGGCCCGGCTGG

GCTGTGCCCCACGATTCCAGGAGTTCCGCCGTGCCTACGAGGCTGCCCGTGCTGCCCACCTCCACCCCTG

CGAGGTGGCGCTGCACTGAGGGGCTGGGTGCTGGGGAGGGGCTGGTAGGAGGGAGGGTGGGCCCACTGCT

TTGGAGGTGATGGGACTATCAATAAGAACTCTGTTCACGCAAAAAAAAAAAAAAAAAAA

Human Meteorin full length amino acid sequence
>IPI00031531.1 REFSEQ_NP:NP_076947 TREMBL:Q9UJH9
ENSEMBL:ENSP00000219542 Tax_Id = 9606 C380A1.2.1 (Novel protein)
                                                            (SEQ ID NO 2)
MGFPAAALLC ALCCGLLAPA ARAGYSEERC SWRGSGLTQE PGSVGQLALA CAEGAVEWLY

PAGALRLTLG GPDPRARPGI ACLRPVRPFA GAQVFAERAG GALELLLAEG PGPAGGRCVR

WGPRERRALF LQATPHQDIS RRVAAFRFEL REDGRPELPP QAHGLGVDGA CRPCSDAELL

LAACTSDFVI HGIIHGVTHD VELQESVITV VAARVLRQTP PLFQAGRSGD QGLTSIRTPL

RCGVHPGPGT FLFMGWSRFG EARLGCAPRF QEFRRAYEAA RAAHLHPCEV ALH

Human Meteorin, protein without signal peptide
                                                            (SEQ ID NO 3)
GYSEERCSWR GSGLTQEPGS VGQLALACAE GAVEWLYPAG ALRLTLGGPD PRARPGIACL
```

RPVRPFAGAQ VFAERAGGAL ELLLAEGPGP AGGRCVRWGP RERRALFLQA TPHQDISRRV

AAFRFELRED GRPELPPQAH GLGVDGACRP CSDAELLLAA CTSDFVIHGI IHGVTHDVEL

QESVITVVAA RVLRQTPPLF QAGRSGDQGL TSIRTPLRCG VHPGPGTFLF MGWSRFGEAR

LGCAPRFQEF RRAYEAARAA HLHPCEVALH

Mouse Meteorin cDNA, 1363 bp, CDS 84..959
NM_133719. *Mus musculus* meteorin.[gi: 56550040]
(SEQ ID NO 4)

gggcagccgc gccgcgggct gctcgcgctg cggccccgac cctcccgggg cagcagtccg aggccccggc gcgtccccta accatgctgg tagccacgct tctttgcgcg ctctgttgcg gcctcctggc cgcgtccgct cacgctggct actcggaaga ccgctgcagc tggaggggca gcggtttgac ccaggagcct ggcagcgtgg ggcagctgac cctggactgt actgagggcg ctatcgagtg gctgtaccca gctggggcgc tgcgcctgac cctgggcggc ccgatccgg gcacacggcc cagcatcgtc tgtctgcgcc cagagcggcc cttcgctggt gcccaggtct tcgctgaacg tatgaccggc aatctagagt tgctactggc cgaggcccg gacctggctg ggggccgctg catgcgctgg ggtccccgcg agcgccgagc ccttttcctg caggccacac cacaccgcga catcagccgc agagttgctg ccttccgttt tgaactgcac gaggaccaac gtgcagaaat gtctccccag gctcaaggtc ttggtgtgga tggtgcctgc aggccctgca gtgatgccga gctcctcctg gctgcatgca ccagtgattt tgtgatccac gggaccatcc atggggtcgc ccatgacaca gagctgcaag aatcagtcat cactgtggtg gttgctcgtg tcatccgcca gacactgcca ctgttcaagg aagggagctc ggaggggcaa ggccgggcct ccattcgtac cttgctgcgc tgtggtgtgc gtcctggccc aggctccttc ctcttcatgg gctggagccg atttggcgaa gcttggctgg gctgtgctcc ccgcttccaa gagttcagcc gtgtctattc agctgctctc acgacccatc tcaacccatg tgagatggca ctggactgag agacctggga gcaagccctg gatggaccct cttctggaga tgggtgttg gggagggtga tgggagggtg ggtgagaagg gtgtggctcg gatggcatcc tggtacccac agtgagctgg tagaatacta agtaatctgg accataccag ccactgtagt catggtcttc tgtggcaggc agcataccca gctctgtgcc tgcctcactt tgtctactct ccagtctgct gcccttctaa cccttcttag cctgctgacc agtgagctca tgttttcctc gaattccagg gtgctgctgg ggttcagagc aaccgtgccg tagtttggaa gacttgagct aattgttttt ttttgtttg ttttttttgtt tgtttaaagg tggcctgggg ggggcggcaa aca Mouse Meteorin full length amino acid sequence
ref|NP_598480.1| meteorin [*Mus musculus*]
(SEQ ID NO 5)
MLVATLLCAL CCGLLAASAH AGYSEDRCSW RGSGLTQEPG SVGQLTLDCT EGAIEWLYPA

GALRLTLGGP DPGTRPSIVC LRPERPFAGA QVFAERMTGN LELLLAEGPD LAGGRCMRWG

PRERRALFLQ ATPHRDISRR VAAFRFELHE DQRAEMSPQA QGLGVDGACR PCSDAELLLA

ACTSDFVIHG TIHGVAHDTE LQESVITVVV ARVIRQTLPL FKEGSSEGQG RASIRTLLRC

GVRPGPGSFL FMGWSRFGEA WLGCAPRFQE FSRVYSAALT THLNPCEMAL D

Mouse Meteorin protein without signal peptide
(SEQ ID NO 6)
GYSEDRCSWR GSGLTQEPGS VGQLTLDCTE GAIEWLYPAG ALRLTLGGPD PGTRPSIVCL RPERPFAGAQ

VFAERMTGNL ELLLAEGPDL AGGRCMRWGP RERRALFLQA TPHRDISRRV AAFRFELHED QRAEMSPQAQ

GLGVDGACRP CSDAELLLAA CTSDFVIHGT IHGVAHDTEL QESVITVVVA RVIRQTLPLF KEGSSEGQGR

ASIRTLLRCG VRPGPGSFLF MGWSRFGEAW LGCAPRFQEF SRVYSAALTT HLNPCEMALD

Rat Meteorin cDNA (1026 bp; CDS = 1-876)

-continued

\>gi|34870570|ref|XM_213261.2| *Rattus norvegicus* similar to 1810034B16Rik protein (LOC287151), mRNA (SEQ ID NO 7)

```
ATGCTGGTAGCGGCGCTTCTCTGCGCGCTGTGCTGCGGCCTCTTGGCTGCGTCCGCTCGAGCTGGCTACT
CCGAGGACCGCTGCAGCTGGAGGGGCAGCGGTTTGACCCAGGAACCTGGCAGCGTGGGGCAGCTGACCCT
GGATTGTACTGAGGGTGCTATCGAGTGGCTGTATCCAGCTGGGGCGCTGCGCCTGACTCTAGGCGGCTCT
GATCCGGGCACGCGGCCCAGCATCGTCTGTCTGCGCCCAACACGGCCCTTCGCTGGTGCCCAGGTCTTCG
CTGAACGGATGGCCGGCAACCTAGAGTTGCTACTGGCCGAGGGCCAAGGCCTGGCTGGGGGCCGCTGCAT
GCGCTGGGGTCCTCGCGAGCGCCGAGCCCTTTTCCTGCAGGCCACGCCACACCGGGACATCAGCCGCAGA
GTTGCTGCCTTCCAATTTGAACTGCACGAGGACCAACGTGCAGAAATGTCTCCCCAGGCCCAAGGTTTTG
GTGTGGATGGTGCCTGCAGGCCCTGCAGTGATGCCGAGCTCCTTCTGACTGCATGCACCAGTGACTTTGT
GATCCATGGGACCATCCATGGGGTCGTCCATGACATGGAGCTGCAAGAATCAGTCATCACTGTGGTGGCC
ACTCGTGTCATCCGCCAGACACTGCCACTGTTCCAGGAAGGGAGCTCGGAGGGCCGGGGCCAGGCCTCCG
TTCGTACCTTGTTGCGCTGTGGTGCGTCCTGGCCCAGGCTCCTTCCTCTTCATGGGCTGGAGCCGATT
TGGCGAAGCTTGGCTGGGCTGCGCTCCCCGCTTCCAAGAGTTCAGCCGTGTCTATTCAGCTGCTCTCGCG
GCCCACCTCAACCCATGTGAGGTGGCACTGGACTGAGAGACCTGGGAGCAAGCCCTGGATGGATCTTCCT
CTGGGGATGGGGTGTTGGGAGGGGTGATAGGAGGGTGGGTGGGAAGGGTGTGGCTCAGATGGCATCCTG
GTACCCACAGTGAGGTGGTAGAATACTAAATAACCTGGATCACACC
```

Rat Meteorin full length amino acid sequence
\>IPI00369281.1 |REFSEQ_XP:XP_213261|ENSEMBL:ENSRNOP00000026676

(SEQ ID NO 8)

MLVAALLCAL CCGLLAASAR AGYSEDRCSW RGSGLTQEPG SVGQLTLDCT EGAIEWLYPA

GALRLTLGGS DPGTRPSIVC LRPTRPFAGA QVFAERMAGN LELLLAEGQG LAGGRCMRWG

PRERRALFLQ ATPHRDISRR VAAFQFELHE DQRAEMSPQA QGFGVDGACR PCSDAELLLT

ACTSDFVIHG TIHGVVHDME LQESVITVVA TRVIRQTLPL FQEGSSEGRG QASVRTLLRC

GVRPGPGSFL FMGWSRFGEA WLGCAPRFQE FSRVYSAALA AHLNPCEVAL D

Rat Meteorin, protein without signal peptide (SEQ ID NO 9)

GYSEDRCSWR GSGLTQEPGS VGQLTLDCTE GAIEWLYPAG ALRLTLGGSD PGTRPSIVCL

RPTRPFAGAQ VFAERMAGNL ELLLAEGQGL AGGRCMRWGP RERRALFLQA TPHRDISRRV

AAFQFELHED QRAEMSPQAQ GFGVDGACRP CSDAELLLTA CTSDFVIHGT IHGVVHDMEL

QESVITVVAT RVIRQTLPLF QEGSSEGRGQ ASVRTLLRCG VRPGPGSFLF MGWSRFGEAW

LGCAPRFQEF SRVYSAALAA HLNPCEVALD

Codon optimized Meteorin nucleotide sequence present in constructs pCAn.Meteorin and pT2.CAn.Meteorin (SEQ ID NO 10)

```
ATGGGCTTTCCCGCTGCCGCCCTGCTGTGCGCTCTGTGCTGCGGACTGCT
GGCTCCTGCAGCCAGAGCCGGCTACAGCGAGGAACGGTGCAGCTGGCGGG
GCAGCGGCCTGACCCAGGAACCTGGCAGCGTCGGCCAGCTCGCACTGGCC
TGTGCAGAAGGCGCCGTGGAGTGGCTGTACCCCGCAGGCGCCCTGAGACT
GACCCTGGGCGGACCCGACCCCAGAGCCAGACCCGGCATTGCCTGTCTGA
GGCCCGTGCGGCCTTTCGCTGGCGCCCAGGTGTTCGCCGAGAGAGCCGGC
GGAGCCCTGGAACTCCTGCTCGCCGAAGGCCCTGGTCCAGCCGGCGGAAG
ATGCGTGAGATGGGGCCCAAGAGAGCGGAGAGCCCTGTTCCTGCAAGCCA
CCCCCCACCAGGACATCAGCAGACGGGTGGCCGCCTTCAGATTCGAGCTG
CGGGAGGACGGTAGACCCGAGCTGCCACCTCAGGCCCACGGACTGGGAGT
```

-continued

```
GGACGGCGCCTGCAGACCCTGTAGCGACGCCGAGCTGCTGCTCGCCGCCT

GCACCAGCGACTTCGTGATCCACGGCATCATCCACGGCGTGACCCACGAC

GTGGAGCTGCAGGAAAGCGTCATCACCGTCGTCGCCGCCAGAGTGCTGAG

ACAGACCCCCCCTCTGTTCCAGGCCGGCAGAAGCGGCGACCAGGGCCTGA

CCAGCATCCGGACCCCCCTGAGATGCGGCGTGCATCCCGGACCCGGCACC

TTCCTGTTCATGGGCTGGTCCAGATTCGGCGAGGCCCGGCTGGGCTGCGC

TCCCCGGTTCCAGGAATTCAGACGGGCCTACGAGGCCGCCAGGGCCGCTC

ATCTGCACCCCTGCGAGGTGGCCCTGCATTGA
```

Consensus sequence, mature Meteorin
(SEQ ID NO 11)
```
GYSEXRCSWR GSGLTQEPGS VGQLXLXCXE GAXEWLYPAG ALRLTLGGXD PXXRPXIXCL    60

RPXRPFAGAQ VFAERXXGXL ELLLAEGXXX AGGRCXRWGP RERRALFLQA TPHXDISRRV   120

AAFXFELXED XRXEXXPQAX GXGVDGACRP CSDAELLLXA CTSDFVIHGX IHGVXHDXEL   180

QESVITVVXX RVXRQTXPLF XXGXSXXXGX XSXRTXLRCG VXPGPGXFLF MGWSRFGEAX   240

LGCAPRFQEF XRXYXAAXXX HLXPCEXALX                                    270
```
X is any of the 21 amino acids that can be encoded by DNA.

---

The invention claimed is:

1. A method of treatment of allodynia in a subject comprising administering to said subject in need thereof therapeutically effective amounts of a neurotrophic polypeptide comprising an amino acid sequence having at least 95% sequence identity to SEQ ID NO: 3 and comprising the consensus sequence of SEQ ID NO: 11, wherein the neurotrophic polypeptide has cysteine residues at positions 7, 28, 59, 95, 148, 151, 161, 219, 243, and 265 relative to the amino acid sequence of SEQ ID NO: 3.

2. The method of claim 1, wherein said polypeptide has at least 98% sequence identity to SEQ ID NO: 3.

3. The method of claim 1, wherein any amino acid substitutions relative to SEQ ID NO: 3 are conservative substitutions.

4. The method of claim 1, wherein said polypeptide is capable of forming at least one intramolecular cysteine bridge.

5. The method according to claim 1, wherein said allodynia is thermal allodynia.

6. The method according to claim 1, wherein said allodynia is cold allodynia.

7. The method according to claim 1, wherein said allodynia is heat allodynia.

8. The method according to claim 1, wherein said allodynia is mechanical allodynia.

9. The method according to claim 1, wherein the subject to be treated is human.

10. The method according to claim 1, wherein the treatment is administered by systemic administration.

11. The method according to claim 1, wherein the treatment is administered by parenteral injection.

12. The method of claim 11, wherein said parenteral injection is subcutaneous injection or intrathecal injection.

13. The method according to claim 1, wherein the treatment is administered in dosages of 1 µg/kg -10,000 µg/kg.

14. The method according to claim 1, wherein said administration is repeated daily.

15. The method according to claim 1, wherein said administration is repeated at least 1-3 times weekly.

16. The method of claim 1, wherein said allodynia is caused by painful diabetic neuropathy, post-herpetic neuralgia, or sciatica.

17. The method according to claim 1, wherein said treatment results in substantially full reversal of allodynia in at least a subset of subjects.

18. The method of claim 1, wherein said polypeptide has the sequence of SEQ ID NO: 3.

19. A method of treating neuropathic pain in a human subject in need thereof comprising administering to the subject a therapeutically effective amount of a neurotrophic polypeptide comprising an amino acid sequence having at least 95% sequence identity to SEQ ID NO: 3 and comprising the consensus sequence of SEQ ID NO: 11, wherein the neurotrophic polypeptide has cysteine residues at positions 7, 28, 59, 95, 148, 151, 161, 219, 243, and 265 relative to the amino acid sequence of SEQ ID NO: 3, and said administration does not occur more than three times per week.

20. The method of claim 19, wherein said administration does not occur more than once a week.

21. The method of claim 19, wherein said administration does not occur more than once every two weeks.

22. The method of claim 19, wherein the therapeutic effect of said treatment ameliorates at least one symptom of neuropathic pain for the entire period between polypeptide administrations.

23. The method of claim 22, wherein said symptom is selected from the group consisting of allodynia, hyperalgesia, spontaneous pain, phantom pain, sensations of burning, tingling, electricity, pins and needles, paresthesia, dysesthesia, stiffness, numbness in the extremities, feelings of bodily distortion, and hyperpathia.

24. The method of claims 19, wherein said treatment does not maintain measurable levels of said polypeptide in the serum of said subject for the entire period between polypeptide administrations.

25. The method of claim 24, wherein the levels of said polypeptide in the serum of said subject falls below 10 ng/mL between polypeptide administrations.

26. The method of claim 19, wherein said administration occurs at least once every three weeks.

27. The method of claim 19, wherein said administration occurs at least once a month.

28. The method of claim 19, wherein said polypeptide has at least 98% sequence identity to SEQ ID NO: 3.

29. The method of claim 19, wherein said polypeptide has the sequence of SEQ ID NO: 3.

30. A method of treating neuropathic pain in a human subject in need thereof comprising administering to the subject a therapeutically effective amount of a neurotrophic polypeptide comprising an amino acid sequence having at least 95% sequence identity to SEQ ID NO: 3 and comprising the consensus sequence of SEQ ID NO: 11, wherein the neurotrophic polypeptide has cysteine residues at positions 7, 28, 59, 95, 148, 151, 161, 219, 243, and 265 relative to the amino acid sequence of SEQ ID NO: 3, said treatment comprises multiple administrations of said neurotrophic polypeptide, and said neurotrophic polypeptide is no longer detectable in the serum of said subject at the time of a second, or subsequent, administration of said neurotrophic polypeptide.

31. The method of claim 30, wherein said administration occurs at least once every three weeks.

32. The method of claim 30, wherein said administration occurs at least once a month.

33. The method of claim 30, wherein said polypeptide has at least 98% sequence identity to SEQ ID NO: 3.

34. The method of claim 30, wherein said polypeptide has the sequence of SEQ ID NO: 3.

35. A method of treating neuropathic pain in a human subject in need thereof comprising administering to the subject a therapeutically effective amount of a neurotrophic polypeptide comprising an amino acid sequence having at least 95% sequence identity to SEQ ID NO: 3 and comprising the consensus sequence of SEQ ID NO: 11, wherein the neurotrophic polypeptide has cysteine residues at positions 7, 28, 59, 95, 148, 151, 161, 219, 243, and 265 relative to the amino acid sequence of SEQ ID NO: 3, said treatment comprises multiple administrations of said neurotrophic polypeptide, and the level of said polypeptide in the serum of said subject falls below 10 ng/mL at the time of a second, or subsequent, administration of said neurotrophic polypeptide.

36. The method of claim 35, wherein said administration occurs at least once every three weeks.

37. The method of claim 35, wherein said administration occurs at least once a month.

38. The method of claim 35, wherein said polypeptide has at least 98% sequence identity to SEQ ID NO: 3.

39. The method of claim 35, wherein said polypeptide has the sequence of SEQ ID NO: 3.

* * * * *

UNITED STATES PATENT AND TRADEMARK OFFICE
CERTIFICATE OF CORRECTION

PATENT NO. : 8,404,642 B2
APPLICATION NO. : 13/251630
DATED : March 26, 2013
INVENTOR(S) : Jesper Roland Jørgensen, Lars Ulrik Wahlberg and Teit E. Johansen Page 1 of 1

It is certified that error appears in the above-identified patent and that said Letters Patent is hereby corrected as shown below:

Title Page
Under "Foreign Patent Documents", replace "WO 2005/095460" with --WO 2005/095450--.

Title Page
Under "Foreign Patent Documents", replace "WO 2007/100808" with --WO 2007/100898--.

In the Claims

Column 66
Line 43, Claim 24, replace "claims" with --claim--.

Signed and Sealed this
Fourth Day of February, 2014

Michelle K. Lee
*Deputy Director of the United States Patent and Trademark Office*

SEQUENCE LISTING

<160> NUMBER OF SEQ ID NOS: 11

<210> SEQ ID NO 1
<211> LENGTH: 1109
<212> TYPE: DNA
<213> ORGANISM: Homo sapiens
<220> FEATURE:
<221> NAME/KEY: CDS
<222> LOCATION: (118)..(999)

<400> SEQUENCE: 1

```
gcttcgccgg ggccgggcgg ccggcgcccc cggctgctcc cgccgccgcc cggacccgcg      60
ccccgccggg gcagcggtgg tgagagcccc gactccccgg acgccgcccg ccgtgcc        117 atg ggg ttc ccg gcc gcg gcg ctg ctc tgc gcg ctg tgc tgc ggc ctc      165
Met Gly Phe Pro Ala Ala Ala Leu Leu Cys Ala Leu Cys Cys Gly Leu
1               5                   10                  15 ctg gcc ccg gct gcc cgc gcc ggc tac tcc gag gag cgc tgc agc tgg     213
Leu Ala Pro Ala Ala Arg Ala Gly Tyr Ser Glu Glu Arg Cys Ser Trp
                20                  25                  30 agg ggc agc ggc ctc acc cag gag ccc ggc agc gtg ggg cag ctg gcc     261
Arg Gly Ser Gly Leu Thr Gln Glu Pro Gly Ser Val Gly Gln Leu Ala
            35                  40                  45 ctg gcc tgt gcg gag ggc gcg gtt gag tgg ctg tac ccg gct ggg gcg     309
Leu Ala Cys Ala Glu Gly Ala Val Glu Trp Leu Tyr Pro Ala Gly Ala
        50                  55                  60 ctg cgc ctg acc ctg ggc ggc ccc gat ccc aga gcg cgg ccc ggc atc     357
Leu Arg Leu Thr Leu Gly Gly Pro Asp Pro Arg Ala Arg Pro Gly Ile
65                  70                  75                  80 gcc tgt ctg cgg ccg gtg cgg ccc ttc gcg ggc gcc cag gtc ttc gcg     405
Ala Cys Leu Arg Pro Val Arg Pro Phe Ala Gly Ala Gln Val Phe Ala
                85                  90                  95 gag cgc gca ggg ggc gcc ctg gag ctg ctg ctg gcc gag ggc ccg ggc     453
Glu Arg Ala Gly Gly Ala Leu Glu Leu Leu Leu Ala Glu Gly Pro Gly
            100                 105                 110 ccg gca ggg ggc cgc tgc gtg cgc tgg ggt ccc cgc gag cgc cgg gcc     501
```

```
Pro Ala Gly Gly Arg Cys Val Arg Trp Gly Pro Arg Glu Arg Arg Ala
        115                 120                 125 ctc ttc ctg cag gcc acg ccg cac cag gac atc agc cgc cgc gtg gcc    549
Leu Phe Leu Gln Ala Thr Pro His Gln Asp Ile Ser Arg Arg Val Ala
130                 135                 140 gcc ttc cgc ttt gag ctg cgc gag gac ggg cgc ccc gag ctg ccc ccg    597
Ala Phe Arg Phe Glu Leu Arg Glu Asp Gly Arg Pro Glu Leu Pro Pro
145                 150                 155                 160 cag gcc cac ggt ctc ggc gta gac ggt gcc tgc agg ccc tgc agc gac    645
Gln Ala His Gly Leu Gly Val Asp Gly Ala Cys Arg Pro Cys Ser Asp
                165                 170                 175 gct gag ctg ctc ctg gcc gca tgc acc agc gac ttc gta att cac ggg    693
Ala Glu Leu Leu Leu Ala Ala Cys Thr Ser Asp Phe Val Ile His Gly
            180                 185                 190 atc atc cat ggg gtc acc cat gac gtg gag ctg cag gag tct gtc atc    741
Ile Ile His Gly Val Thr His Asp Val Glu Leu Gln Glu Ser Val Ile
        195                 200                 205 act gtg gtg gcc gcc cgt gtc ctc cgc cag aca ccg ccg ctg ttc cag    789
Thr Val Val Ala Ala Arg Val Leu Arg Gln Thr Pro Pro Leu Phe Gln
210                 215                 220 gcg ggg cga tcc ggg gac cag ggg ctg acc tcc att cgt acc cca ctg    837
Ala Gly Arg Ser Gly Asp Gln Gly Leu Thr Ser Ile Arg Thr Pro Leu
225                 230                 235                 240 cgc tgt ggc gtc cac ccg ggc cca ggc acc ttc ctc ttc atg ggc tgg    885
Arg Cys Gly Val His Pro Gly Pro Gly Thr Phe Leu Phe Met Gly Trp
                245                 250                 255 agc cgc ttt ggg gag gcc cgg ctg ggc tgt gcc cca cga ttc cag gag    933
Ser Arg Phe Gly Glu Ala Arg Leu Gly Cys Ala Pro Arg Phe Gln Glu
            260                 265                 270 ttc cgc cgt gcc tac gag gct gcc cgt gct gcc cac ctc cac ccc tgc    981
Phe Arg Arg Ala Tyr Glu Ala Ala Arg Ala Ala His Leu His Pro Cys
        275                 280                 285 gag gtg gcg ctg cac tga ggggctgggt gctggggagg ggctggtagg           1029
Glu Val Ala Leu His
        290 agggagggtg ggcccactgc tttggaggtg atgggactat caataagaac tctgttcacg   1089 caaaaaaaaa aaaaaaaaaa                                               1109

<210> SEQ ID NO 2
<211> LENGTH: 293
<212> TYPE: PRT
<213> ORGANISM: Homo sapiens

<400> SEQUENCE: 2

Met Gly Phe Pro Ala Ala Ala Leu Leu Cys Ala Leu Cys Cys Gly Leu
1               5                   10                  15

Leu Ala Pro Ala Ala Arg Ala Gly Tyr Ser Glu Glu Arg Cys Ser Trp
            20                  25                  30

Arg Gly Ser Gly Leu Thr Gln Glu Pro Gly Ser Val Gly Gln Leu Ala
        35                  40                  45

Leu Ala Cys Ala Glu Gly Ala Val Glu Trp Leu Tyr Pro Ala Gly Ala
    50                  55                  60

Leu Arg Leu Thr Leu Gly Gly Pro Asp Pro Arg Ala Arg Pro Gly Ile
65                  70                  75                  80

Ala Cys Leu Arg Pro Val Arg Pro Phe Ala Gly Ala Gln Val Phe Ala
                85                  90                  95

Glu Arg Ala Gly Gly Ala Leu Glu Leu Leu Leu Ala Glu Gly Pro Gly
            100                 105                 110
```

```
Pro Ala Gly Gly Arg Cys Val Arg Trp Gly Pro Arg Glu Arg Arg Ala
            115                 120                 125

Leu Phe Leu Gln Ala Thr Pro His Gln Asp Ile Ser Arg Arg Val Ala
130                 135                 140

Ala Phe Arg Phe Glu Leu Arg Glu Asp Gly Arg Pro Glu Leu Pro Pro
145                 150                 155                 160

Gln Ala His Gly Leu Gly Val Asp Gly Ala Cys Arg Pro Cys Ser Asp
                165                 170                 175

Ala Glu Leu Leu Leu Ala Ala Cys Thr Ser Asp Phe Val Ile His Gly
            180                 185                 190

Ile Ile His Gly Val Thr His Asp Val Glu Leu Gln Glu Ser Val Ile
        195                 200                 205

Thr Val Val Ala Ala Arg Val Leu Arg Gln Thr Pro Pro Leu Phe Gln
    210                 215                 220

Ala Gly Arg Ser Gly Asp Gln Gly Leu Thr Ser Ile Arg Thr Pro Leu
225                 230                 235                 240

Arg Cys Gly Val His Pro Gly Pro Gly Thr Phe Leu Phe Met Gly Trp
                245                 250                 255

Ser Arg Phe Gly Glu Ala Arg Leu Gly Cys Ala Pro Arg Phe Gln Glu
            260                 265                 270

Phe Arg Arg Ala Tyr Glu Ala Ala Arg Ala Ala His Leu His Pro Cys
        275                 280                 285

Glu Val Ala Leu His
    290

<210> SEQ ID NO 3
<211> LENGTH: 270
<212> TYPE: PRT
<213> ORGANISM: Homo sapiens

<400> SEQUENCE: 3

Gly Tyr Ser Glu Glu Arg Cys Ser Trp Arg Gly Ser Gly Leu Thr Gln
1               5                   10                  15

Glu Pro Gly Ser Val Gly Gln Leu Ala Leu Ala Cys Ala Glu Gly Ala
            20                  25                  30

Val Glu Trp Leu Tyr Pro Ala Gly Ala Leu Arg Leu Thr Leu Gly Gly
        35                  40                  45

Pro Asp Pro Arg Ala Arg Pro Gly Ile Ala Cys Leu Arg Pro Val Arg
    50                  55                  60

Pro Phe Ala Gly Ala Gln Val Phe Ala Glu Arg Ala Gly Gly Ala Leu
65                  70                  75                  80

Glu Leu Leu Leu Ala Glu Gly Pro Gly Pro Ala Gly Gly Arg Cys Val
                85                  90                  95

Arg Trp Gly Pro Arg Glu Arg Arg Ala Leu Phe Leu Gln Ala Thr Pro
            100                 105                 110

His Gln Asp Ile Ser Arg Arg Val Ala Ala Phe Arg Phe Glu Leu Arg
        115                 120                 125

Glu Asp Gly Arg Pro Glu Leu Pro Pro Gln Ala His Gly Leu Gly Val
    130                 135                 140

Asp Gly Ala Cys Arg Pro Cys Ser Asp Ala Glu Leu Leu Leu Ala Ala
145                 150                 155                 160

Cys Thr Ser Asp Phe Val Ile His Gly Ile His Gly Val Thr His
                165                 170                 175

Asp Val Glu Leu Gln Glu Ser Val Ile Thr Val Val Ala Ala Arg Val
            180                 185                 190
```

```
Leu Arg Gln Thr Pro Pro Leu Phe Gln Ala Gly Arg Ser Gly Asp Gln
        195                 200                 205

Gly Leu Thr Ser Ile Arg Thr Pro Leu Arg Cys Gly Val His Pro Gly
    210                 215                 220

Pro Gly Thr Phe Leu Phe Met Gly Trp Ser Arg Phe Gly Glu Ala Arg
225                 230                 235                 240

Leu Gly Cys Ala Pro Arg Phe Gln Glu Phe Arg Arg Ala Tyr Glu Ala
                245                 250                 255

Ala Arg Ala Ala His Leu His Pro Cys Glu Val Ala Leu His
        260                 265                 270

<210> SEQ ID NO 4
<211> LENGTH: 1363
<212> TYPE: DNA
<213> ORGANISM: Mus musculus
<220> FEATURE:
<221> NAME/KEY: CDS
<222> LOCATION: (84)..(959)

<400> SEQUENCE: 4
gggcagccgc gccgcgggct gctcgcgctg cggccccgac cctcccgggg cagcagtccg    60
aggccccggc gcgtccccta acc atg ctg gta gcc acg ctt ctt tgc gcg ctc   113
                          Met Leu Val Ala Thr Leu Leu Cys Ala Leu
                            1               5                  10 tgt tgc ggc ctc ctg gcc gcg tcc gct cac gct ggc tac tcg gaa gac   161
Cys Cys Gly Leu Leu Ala Ala Ser Ala His Ala Gly Tyr Ser Glu Asp
                 15                  20                  25 cgc tgc agc tgg agg ggc agc ggt ttg acc cag gag cct ggc agc gtg   209
Arg Cys Ser Trp Arg Gly Ser Gly Leu Thr Gln Glu Pro Gly Ser Val
         30                  35                  40 ggg cag ctg acc ctg gac tgt act gag ggc gct atc gag tgg ctg tac   257
Gly Gln Leu Thr Leu Asp Cys Thr Glu Gly Ala Ile Glu Trp Leu Tyr
     45                  50                  55 cca gct ggg gcg ctg cgc ctg acc ctg ggc ggc ccc gat ccg ggc aca   305
Pro Ala Gly Ala Leu Arg Leu Thr Leu Gly Gly Pro Asp Pro Gly Thr
 60                  65                  70 cgg ccc agc atc gtc tgt ctg cgc cca gag cgg ccc ttc gct ggt gcc   353
Arg Pro Ser Ile Val Cys Leu Arg Pro Glu Arg Pro Phe Ala Gly Ala
 75                  80                  85                  90 cag gtc ttc gct gaa cgt atg acc ggc aat cta gag ttg cta ctg gcc   401
Gln Val Phe Ala Glu Arg Met Thr Gly Asn Leu Glu Leu Leu Leu Ala
                 95                 100                 105 gag ggc ccg gac ctg gct ggg ggc cgc tgc atg cgc tgg ggt ccc cgc   449
Glu Gly Pro Asp Leu Ala Gly Gly Arg Cys Met Arg Trp Gly Pro Arg
             110                 115                 120 gag cgc cga gcc ctt ttc ctg cag gcc aca cca cac cgc gac atc agc   497
Glu Arg Arg Ala Leu Phe Leu Gln Ala Thr Pro His Arg Asp Ile Ser
         125                 130                 135 cgc aga gtt gct gcc ttc cgt ttt gaa ctg cac gag gac caa cgt gca   545
Arg Arg Val Ala Ala Phe Arg Phe Glu Leu His Glu Asp Gln Arg Ala
     140                 145                 150 gaa atg tct ccc cag gct caa ggt ctt ggt gtg gat ggt gcc tgc agg   593
Glu Met Ser Pro Gln Ala Gln Gly Leu Gly Val Asp Gly Ala Cys Arg
155                 160                 165                 170 ccc tgc agt gat gcc gag ctc ctc ctg gct gca tgc acc agt gat ttt   641
Pro Cys Ser Asp Ala Glu Leu Leu Leu Ala Ala Cys Thr Ser Asp Phe
                 175                 180                 185 gtg atc cac ggg acc atc cat ggg gtc gcc cat gac aca gag ctg caa   689
Val Ile His Gly Thr Ile His Gly Val Ala His Asp Thr Glu Leu Gln
             190                 195                 200
```

-continued

```
gaa tca gtc atc act gtg gtg gtt gct cgt gtc atc cgc cag aca ctg    737
Glu Ser Val Ile Thr Val Val Val Ala Arg Val Ile Arg Gln Thr Leu
        205                 210                 215 cca ctg ttc aag gaa ggg agc tcg gag ggc caa ggc cgg gcc tcc att    785
Pro Leu Phe Lys Glu Gly Ser Ser Glu Gly Gln Gly Arg Ala Ser Ile
    220                 225                 230 cgt acc ttg ctg cgc tgt ggt gtg cgt cct ggc cca ggc tcc ttc ctc    833
Arg Thr Leu Leu Arg Cys Gly Val Arg Pro Gly Pro Gly Ser Phe Leu
235                 240                 245                 250 ttc atg ggc tgg agc cga ttt ggc gaa gct tgg ctg ggc tgt gct ccc    881
Phe Met Gly Trp Ser Arg Phe Gly Glu Ala Trp Leu Gly Cys Ala Pro
                255                 260                 265 cgc ttc caa gag ttc agc cgt gtc tat tca gct gct ctc acg acc cat    929
Arg Phe Gln Glu Phe Ser Arg Val Tyr Ser Ala Ala Leu Thr Thr His
            270                 275                 280 ctc aac cca tgt gag atg gca ctg gac tga gagacctggg agcaagccct     979
Leu Asn Pro Cys Glu Met Ala Leu Asp
        285                 290 ggatggacct tcttctggag atgggtgtt ggggagggtg atgggagggt gggtgagaag   1039
ggtgtggctc ggatggcatc ctggtaccca cagtgagctg gtagaatact aagtaatctg  1099
gaccatacca gccactgtag tcatggtctt ctgtggcagg cagcataccc agctctgtgc  1159
ctgcctcact tgtctactc tccagtctgc tgcccttcta acccttctta gcctgctgac   1219
cagtgagctc atgttttcct cgaattccag ggtgctgctg gggttcagag caaccgtgcc  1279
gtagtttgga agacttgagc taattgtttt tttttgttt gttttttgt ttgtttaaag   1339 gtggcctggg gggggcggca aaca                                        1363

<210> SEQ ID NO 5
<211> LENGTH: 291
<212> TYPE: PRT
<213> ORGANISM: Mus musculus

<400> SEQUENCE: 5

Met Leu Val Ala Thr Leu Leu Cys Ala Leu Cys Cys Gly Leu Leu Ala
1               5                   10                  15

Ala Ser Ala His Ala Gly Tyr Ser Glu Asp Arg Cys Ser Trp Arg Gly
            20                  25                  30

Ser Gly Leu Thr Gln Glu Pro Gly Ser Val Gly Gln Leu Thr Leu Asp
        35                  40                  45

Cys Thr Glu Gly Ala Ile Glu Trp Leu Tyr Pro Ala Gly Ala Leu Arg
    50                  55                  60

Leu Thr Leu Gly Gly Pro Asp Pro Gly Thr Arg Pro Ser Ile Val Cys
65                  70                  75                  80

Leu Arg Pro Glu Arg Pro Phe Ala Gly Ala Gln Val Phe Ala Glu Arg
                85                  90                  95

Met Thr Gly Asn Leu Glu Leu Leu Ala Glu Gly Pro Asp Leu Ala
            100                 105                 110

Gly Gly Arg Cys Met Arg Trp Gly Pro Arg Glu Arg Ala Leu Phe
        115                 120                 125

Leu Gln Ala Thr Pro His Arg Asp Ile Ser Arg Arg Val Ala Ala Phe
    130                 135                 140

Arg Phe Glu Leu His Glu Asp Gln Arg Ala Glu Met Ser Pro Gln Ala
145                 150                 155                 160

Gln Gly Leu Gly Val Asp Gly Ala Cys Arg Pro Cys Ser Asp Ala Glu
                165                 170                 175

Leu Leu Leu Ala Ala Cys Thr Ser Asp Phe Val Ile His Gly Thr Ile
```

```
                        180                 185                 190
His Gly Val Ala His Asp Thr Glu Leu Gln Glu Ser Val Ile Thr Val
            195                 200                 205
Val Val Ala Arg Val Ile Arg Gln Thr Leu Pro Leu Phe Lys Glu Gly
        210                 215                 220
Ser Ser Glu Gly Gln Gly Arg Ala Ser Ile Arg Thr Leu Leu Arg Cys
225                 230                 235                 240
Gly Val Arg Pro Gly Pro Gly Ser Phe Leu Phe Met Gly Trp Ser Arg
                245                 250                 255
Phe Gly Glu Ala Trp Leu Gly Cys Ala Pro Arg Phe Gln Glu Phe Ser
            260                 265                 270
Arg Val Tyr Ser Ala Ala Leu Thr Thr His Leu Asn Pro Cys Glu Met
        275                 280                 285
Ala Leu Asp
    290

<210> SEQ ID NO 6
<211> LENGTH: 270
<212> TYPE: PRT
<213> ORGANISM: Mus musculus

<400> SEQUENCE: 6

Gly Tyr Ser Glu Asp Arg Cys Ser Trp Arg Gly Ser Gly Leu Thr Gln
1               5                   10                  15
Glu Pro Gly Ser Val Gly Gln Leu Thr Leu Asp Cys Thr Glu Gly Ala
            20                  25                  30
Ile Glu Trp Leu Tyr Pro Ala Gly Ala Leu Arg Leu Thr Leu Gly Gly
        35                  40                  45
Pro Asp Pro Gly Thr Arg Pro Ser Ile Val Cys Leu Arg Pro Glu Arg
    50                  55                  60
Pro Phe Ala Gly Ala Gln Val Phe Ala Glu Arg Met Thr Gly Asn Leu
65                  70                  75                  80
Glu Leu Leu Leu Ala Glu Gly Pro Asp Leu Ala Gly Gly Arg Cys Met
                85                  90                  95
Arg Trp Gly Pro Arg Glu Arg Arg Ala Leu Phe Leu Gln Ala Thr Pro
            100                 105                 110
His Arg Asp Ile Ser Arg Arg Val Ala Ala Phe Arg Phe Glu Leu His
        115                 120                 125
Glu Asp Gln Arg Ala Glu Met Ser Pro Gln Ala Gln Gly Leu Gly Val
    130                 135                 140
Asp Gly Ala Cys Arg Pro Cys Ser Asp Ala Glu Leu Leu Leu Ala Ala
145                 150                 155                 160
Cys Thr Ser Asp Phe Val Ile His Gly Thr Ile His Gly Val Ala His
                165                 170                 175
Asp Thr Glu Leu Gln Glu Ser Val Ile Thr Val Val Ala Arg Val
            180                 185                 190
Ile Arg Gln Thr Leu Pro Leu Phe Lys Glu Gly Ser Ser Glu Gly Gln
        195                 200                 205
Gly Arg Ala Ser Ile Arg Thr Leu Leu Arg Cys Gly Val Arg Pro Gly
    210                 215                 220
Pro Gly Ser Phe Leu Phe Met Gly Trp Ser Arg Phe Gly Glu Ala Trp
225                 230                 235                 240
Leu Gly Cys Ala Pro Arg Phe Gln Glu Phe Ser Arg Val Tyr Ser Ala
                245                 250                 255
Ala Leu Thr Thr His Leu Asn Pro Cys Glu Met Ala Leu Asp
```

<210> SEQ ID NO 7
<211> LENGTH: 1026
<212> TYPE: DNA
<213> ORGANISM: Rattus norvegicus
<220> FEATURE:
<221> NAME/KEY: CDS
<222> LOCATION: (1)..(876)

<400> SEQUENCE: 7

| | | | | | | | | | | | | | | | | |
|---|---|---|---|---|---|---|---|---|---|---|---|---|---|---|---|---|
| atg | ctg | gta | gcg | gcg | ctt | ctc | tgc | gcg | ctg | tgc | tgc | ggc | ctc | ttg | gct | 48 |
| Met | Leu | Val | Ala | Ala | Leu | Leu | Cys | Ala | Leu | Cys | Cys | Gly | Leu | Leu | Ala | |
| 1 | | | | 5 | | | | | 10 | | | | | 15 | | |
| gcg | tcc | gct | cga | gct | ggc | tac | tcc | gag | gac | cgc | tgc | agc | tgg | agg | ggc | 96 |
| Ala | Ser | Ala | Arg | Ala | Gly | Tyr | Ser | Glu | Asp | Arg | Cys | Ser | Trp | Arg | Gly | |
| | | | 20 | | | | | 25 | | | | | 30 | | | |
| agc | ggt | ttg | acc | cag | gaa | cct | ggc | agc | gtg | ggg | cag | ctg | acc | ctg | gat | 144 |
| Ser | Gly | Leu | Thr | Gln | Glu | Pro | Gly | Ser | Val | Gly | Gln | Leu | Thr | Leu | Asp | |
| | | 35 | | | | | 40 | | | | | 45 | | | | |
| tgt | act | gag | ggt | gct | atc | gag | tgg | ctg | tat | cca | gct | ggg | gcg | ctg | cgc | 192 |
| Cys | Thr | Glu | Gly | Ala | Ile | Glu | Trp | Leu | Tyr | Pro | Ala | Gly | Ala | Leu | Arg | |
| 50 | | | | | 55 | | | | | 60 | | | | | | |
| ctg | act | cta | ggc | ggc | tct | gat | ccg | ggc | acg | cgg | ccc | agc | atc | gtc | tgt | 240 |
| Leu | Thr | Leu | Gly | Gly | Ser | Asp | Pro | Gly | Thr | Arg | Pro | Ser | Ile | Val | Cys | |
| 65 | | | | | 70 | | | | | 75 | | | | | 80 | |
| ctg | cgc | cca | aca | cgg | ccc | ttc | gct | ggt | gcc | cag | gtc | ttc | gct | gaa | cgg | 288 |
| Leu | Arg | Pro | Thr | Arg | Pro | Phe | Ala | Gly | Ala | Gln | Val | Phe | Ala | Glu | Arg | |
| | | | | 85 | | | | | 90 | | | | | 95 | | |
| atg | gcc | ggc | aac | cta | gag | ttg | cta | ctg | gcc | gag | ggc | caa | ggc | ctg | gct | 336 |
| Met | Ala | Gly | Asn | Leu | Glu | Leu | Leu | Leu | Ala | Glu | Gly | Gln | Gly | Leu | Ala | |
| | | | 100 | | | | | 105 | | | | | 110 | | | |
| ggg | ggc | cgc | tgc | atg | cgc | tgg | ggt | cct | cgc | gag | cgc | cga | gcc | ctt | ttc | 384 |
| Gly | Gly | Arg | Cys | Met | Arg | Trp | Gly | Pro | Arg | Glu | Arg | Arg | Ala | Leu | Phe | |
| | | 115 | | | | | 120 | | | | | 125 | | | | |
| ctg | cag | gcc | acg | cca | cac | cgg | gac | atc | agc | cgc | aga | gtt | gct | gcc | ttc | 432 |
| Leu | Gln | Ala | Thr | Pro | His | Arg | Asp | Ile | Ser | Arg | Arg | Val | Ala | Ala | Phe | |
| | 130 | | | | | 135 | | | | | 140 | | | | | |
| caa | ttt | gaa | ctg | cac | gag | gac | caa | cgt | gca | gaa | atg | tct | ccc | cag | gcc | 480 |
| Gln | Phe | Glu | Leu | His | Glu | Asp | Gln | Arg | Ala | Glu | Met | Ser | Pro | Gln | Ala | |
| 145 | | | | | 150 | | | | | 155 | | | | | 160 | |
| caa | ggt | ttt | ggt | gtg | gat | ggt | gcc | tgc | agg | ccc | tgc | agt | gat | gcc | gag | 528 |
| Gln | Gly | Phe | Gly | Val | Asp | Gly | Ala | Cys | Arg | Pro | Cys | Ser | Asp | Ala | Glu | |
| | | | | 165 | | | | | 170 | | | | | 175 | | |
| ctc | ctt | ctg | act | gca | tgc | acc | agt | gac | ttt | gtg | atc | cat | ggg | acc | atc | 576 |
| Leu | Leu | Leu | Thr | Ala | Cys | Thr | Ser | Asp | Phe | Val | Ile | His | Gly | Thr | Ile | |
| | | | 180 | | | | | 185 | | | | | 190 | | | |
| cat | ggg | gtc | gtc | cat | gac | atg | gag | ctg | caa | gaa | tca | gtc | atc | act | gtg | 624 |
| His | Gly | Val | Val | His | Asp | Met | Glu | Leu | Gln | Glu | Ser | Val | Ile | Thr | Val | |
| | | 195 | | | | | 200 | | | | | 205 | | | | |
| gtg | gcc | act | cgt | gtc | atc | cgc | cag | aca | ctg | cca | ctg | ttc | cag | gaa | ggg | 672 |
| Val | Ala | Thr | Arg | Val | Ile | Arg | Gln | Thr | Leu | Pro | Leu | Phe | Gln | Glu | Gly | |
| | 210 | | | | | 215 | | | | | 220 | | | | | |
| agc | tcg | gag | ggc | cgg | ggc | cag | gcc | tcc | gtt | cgt | acc | ttg | ttg | cgc | tgt | 720 |
| Ser | Ser | Glu | Gly | Arg | Gly | Gln | Ala | Ser | Val | Arg | Thr | Leu | Leu | Arg | Cys | |
| 225 | | | | | 230 | | | | | 235 | | | | | 240 | |
| ggt | gtg | cgt | cct | ggc | cca | ggc | tcc | ttc | ctc | ttc | atg | ggc | tgg | agc | cga | 768 |
| Gly | Val | Arg | Pro | Gly | Pro | Gly | Ser | Phe | Leu | Phe | Met | Gly | Trp | Ser | Arg | |
| | | | | 245 | | | | | 250 | | | | | 255 | | |
| ttt | ggc | gaa | gct | tgg | ctg | ggc | tgc | gct | ccc | cgc | ttc | caa | gag | ttc | agc | 816 |
| Phe | Gly | Glu | Ala | Trp | Leu | Gly | Cys | Ala | Pro | Arg | Phe | Gln | Glu | Phe | Ser | |
| | | | 260 | | | | | 265 | | | | | 270 | | | |

-continued

```
cgt gtc tat tca gct gct ctc gcg gcc cac ctc aac cca tgt gag gtg      864
Arg Val Tyr Ser Ala Ala Leu Ala Ala His Leu Asn Pro Cys Glu Val
        275                 280                 285 gca ctg gac tga gagacctggg agcaagccct ggatggatct tcctctgggg          916
Ala Leu Asp
    290 atggggtgtt gggagggggt gataggaggg tgggtgggaa gggtgtggct cagatggcat    976 cctggtaccc acagtgaggt ggtagaatac taaataacct ggatcacacc              1026
```

<210> SEQ ID NO 8
<211> LENGTH: 291
<212> TYPE: PRT
<213> ORGANISM: Rattus norvegicus

<400> SEQUENCE: 8

```
Met Leu Val Ala Ala Leu Leu Cys Ala Leu Cys Cys Gly Leu Leu Ala
1               5                   10                  15

Ala Ser Ala Arg Ala Gly Tyr Ser Glu Asp Arg Cys Ser Trp Arg Gly
            20                  25                  30

Ser Gly Leu Thr Gln Glu Pro Gly Ser Val Gly Gln Leu Thr Leu Asp
        35                  40                  45

Cys Thr Glu Gly Ala Ile Glu Trp Leu Tyr Pro Ala Gly Ala Leu Arg
    50                  55                  60

Leu Thr Leu Gly Gly Ser Asp Pro Gly Thr Arg Pro Ser Ile Val Cys
65                  70                  75                  80

Leu Arg Pro Thr Arg Pro Phe Ala Gly Ala Gln Val Phe Ala Glu Arg
                85                  90                  95

Met Ala Gly Asn Leu Glu Leu Leu Ala Glu Gly Gln Gly Leu Ala
            100                 105                 110

Gly Gly Arg Cys Met Arg Trp Gly Pro Arg Glu Arg Ala Leu Phe
        115                 120                 125

Leu Gln Ala Thr Pro His Arg Asp Ile Ser Arg Arg Val Ala Ala Phe
    130                 135                 140

Gln Phe Glu Leu His Glu Asp Gln Arg Ala Glu Met Ser Pro Gln Ala
145                 150                 155                 160

Gln Gly Phe Gly Val Asp Gly Ala Cys Arg Pro Cys Ser Asp Ala Glu
                165                 170                 175

Leu Leu Leu Thr Ala Cys Thr Ser Asp Phe Val Ile His Gly Thr Ile
            180                 185                 190

His Gly Val Val His Asp Met Glu Leu Gln Glu Ser Val Ile Thr Val
        195                 200                 205

Val Ala Thr Arg Val Ile Arg Gln Thr Leu Pro Leu Phe Gln Glu Gly
    210                 215                 220

Ser Ser Glu Gly Arg Gly Gln Ala Ser Val Arg Thr Leu Leu Arg Cys
225                 230                 235                 240

Gly Val Arg Pro Gly Pro Gly Ser Phe Leu Phe Met Gly Trp Ser Arg
                245                 250                 255

Phe Gly Glu Ala Trp Leu Gly Cys Ala Pro Arg Phe Gln Glu Phe Ser
            260                 265                 270

Arg Val Tyr Ser Ala Ala Leu Ala Ala His Leu Asn Pro Cys Glu Val
        275                 280                 285

Ala Leu Asp
    290
```

<210> SEQ ID NO 9

<211> LENGTH: 270
<212> TYPE: PRT
<213> ORGANISM: Rattus norvegicus

<400> SEQUENCE: 9

```
Gly Tyr Ser Glu Asp Arg Cys Ser Trp Arg Gly Ser Gly Leu Thr Gln
  1               5                  10                  15
Glu Pro Gly Ser Val Gly Gln Leu Thr Leu Asp Cys Thr Glu Gly Ala
             20                  25                  30
Ile Glu Trp Leu Tyr Pro Ala Gly Ala Leu Arg Leu Thr Leu Gly Gly
         35                  40                  45
Ser Asp Pro Gly Thr Arg Pro Ser Ile Val Cys Leu Arg Pro Thr Arg
 50                  55                  60
Pro Phe Ala Gly Ala Gln Val Phe Ala Glu Arg Met Ala Gly Asn Leu
 65                  70                  75                  80
Glu Leu Leu Leu Ala Glu Gly Gln Gly Leu Ala Gly Gly Arg Cys Met
                 85                  90                  95
Arg Trp Gly Pro Arg Glu Arg Arg Ala Leu Phe Leu Gln Ala Thr Pro
            100                 105                 110
His Arg Asp Ile Ser Arg Arg Val Ala Ala Phe Gln Phe Glu Leu His
        115                 120                 125
Glu Asp Gln Arg Ala Glu Met Ser Pro Gln Ala Gln Gly Phe Gly Val
    130                 135                 140
Asp Gly Ala Cys Arg Pro Cys Ser Asp Ala Glu Leu Leu Leu Thr Ala
145                 150                 155                 160
Cys Thr Ser Asp Phe Val Ile His Gly Thr Ile His Gly Val Val His
                165                 170                 175
Asp Met Glu Leu Gln Glu Ser Val Ile Thr Val Val Ala Thr Arg Val
            180                 185                 190
Ile Arg Gln Thr Leu Pro Leu Phe Gln Glu Gly Ser Ser Glu Gly Arg
        195                 200                 205
Gly Gln Ala Ser Val Arg Thr Leu Leu Arg Cys Gly Val Arg Pro Gly
    210                 215                 220
Pro Gly Ser Phe Leu Phe Met Gly Trp Ser Arg Phe Gly Glu Ala Trp
225                 230                 235                 240
Leu Gly Cys Ala Pro Arg Phe Gln Glu Phe Ser Arg Val Tyr Ser Ala
                245                 250                 255
Ala Leu Ala Ala His Leu Asn Pro Cys Glu Val Ala Leu Asp
            260                 265                 270
```

<210> SEQ ID NO 10
<211> LENGTH: 882
<212> TYPE: DNA
<213> ORGANISM: Artificial sequence
<220> FEATURE:
<223> OTHER INFORMATION: Codon optimised

<400> SEQUENCE: 10

```
atgggctttc ccgctgccgc cctgctgtgc gctctgtgct gcggactgct ggctcctgca    60
gccagagccg gctacagcga ggaacggtgc agctggcggg gcagcggcct gacccaggaa   120
cctggcagcg tcggccagct cgcactggcc tgtgcagaag cgccgtggag tggctgtac    180
cccgcaggcg ccctgagact gaccctgggc ggacccgacc ccagccagac ccggcatt    240
gcctgtctga ggcccgtgcg gccttttcgc tggcgcccagg tgttcgccga gagagcggc    300
ggagccctgg aactcctgct cgccgaaggc cctggtccag ccggcggaag atgcgtgaga    360
tgggcccaa gagagcggag agccctgttc ctgcaagcca ccccccacca ggacatcagc    420
```

-continued

```
agacgggtgg ccgccttcag attcgagctg cgggaggacg gtagacccga gctgccacct    480
caggcccacg gactgggagt ggacggcgcc tgcagaccct gtagcgacgc cgagctgctg    540
ctcgccgcct gcaccagcga cttcgtgatc cacggcatca tccacggcgt gacccacgac    600
gtggagctgc aggaaagcgt catcaccgtc gtcgccgcca gagtgctgag acagaccccc    660
cctctgttcc aggccggcag aagcggcgac cagggcctga ccagcatccg accccccctg    720
agatgcggcg tgcatcccgg acccggcacc ttcctgttca tgggctggtc cagattcggc    780
gaggcccggc tgggctgcgc tccccggttc caggaattca gacgggccta cgaggccgcc    840
agggccgctc atctgcaccc ctgcgaggtg gccctgcatt ga                       882
```

```
<210> SEQ ID NO 11
<211> LENGTH: 270
<212> TYPE: PRT
<213> ORGANISM: Artificial sequence
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (76)..(77)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (88)..(90)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
```

```
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (124)..(124)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (131)..(131)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid
<220> FEATURE:
<221> NAME/KEY: misc_feature
<222> LOCATION: (135)..(136)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid
<220> FEATURE:
<221> NAME/KEY: misc_feature
<222> LOCATION: (178)..(178)
<223> OTHER INFORMATION: Xaa can be any naturally occurring amino acid
<220> FEATURE:
<221> NAME/KEY: misc_feature
<222> LOCATION: (189)..(190)
<223> OTHER INFORMATION: Xaa can be any naturally occurring amino acid
<220> FEATURE:
<221> NAME/KEY: misc_feature
<222> LOCATION: (193)..(193)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (201)..(202)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (206)..(208)
<223> OTHER INFORMATION: Xaa can be any naturally occurring amino acid
<220> FEATURE:
<221> NAME/KEY: misc_feature
<222> LOCATION: (210)..(211)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
```

```
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (251)..(251)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid
<220> FEATURE:
<221> NAME/KEY: misc_feature
<222> LOCATION: (255)..(255)
<223> OTHER INFORMATION: Xaa can be any naturally occurring amino acid
<220> FEATURE:
<221> NAME/KEY: misc_feature
<222> LOCATION: (258)..(260)
<223> OTHER INFORMATION: Xaa can be any naturally occurring amino acid
<220> FEATURE:
<221> NAME/KEY: misc_feature
<222> LOCATION: (263)..(263)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (270)..(270)
<223> OTHER INFORMATION: Xaa can be any naturally occurring amino acid

<400> SEQUENCE: 11

Gly Tyr Ser Glu Xaa Arg Cys Ser Trp Arg Gly Ser Gly Leu Thr Gln
1               5                   10                  15

Glu Pro Gly Ser Val Gly Gln Leu Xaa Leu Xaa Cys Xaa Glu Gly Ala
            20                  25                  30

Xaa Glu Trp Leu Tyr Pro Ala Gly Ala Leu Arg Leu Thr Leu Gly Gly
        35                  40                  45

Xaa Asp Pro Xaa Xaa Arg Pro Xaa Ile Xaa Cys Leu Arg Pro Xaa Arg
    50                  55                  60

Pro Phe Ala Gly Ala Gln Val Phe Ala Glu Arg Xaa Xaa Gly Xaa Leu
65                  70                  75                  80

Glu Leu Leu Leu Ala Glu Gly Xaa Xaa Xaa Ala Gly Gly Arg Cys Xaa
                85                  90                  95

Arg Trp Gly Pro Arg Glu Arg Arg Ala Leu Phe Leu Gln Ala Thr Pro
            100                 105                 110

His Xaa Asp Ile Ser Arg Arg Val Ala Ala Phe Xaa Phe Glu Leu Xaa
        115                 120                 125

Glu Asp Xaa Arg Xaa Glu Xaa Xaa Pro Gln Ala Xaa Gly Xaa Gly Val
    130                 135                 140

Asp Gly Ala Cys Arg Pro Cys Ser Asp Ala Glu Leu Leu Leu Xaa Ala
145                 150                 155                 160

Cys Thr Ser Asp Phe Val Ile His Gly Xaa Ile His Gly Val Xaa His
                165                 170                 175
```

```
                     -continued
Asp Xaa Glu Leu Gln Glu Ser Val Ile Thr Val Val Xaa Xaa Arg Val
            180                 185                 190

Xaa Arg Gln Thr Xaa Pro Leu Phe Xaa Xaa Gly Xaa Ser Xaa Xaa Xaa
        195             200                 205

Gly Xaa Xaa Ser Xaa Arg Thr Xaa Leu Arg Cys Gly Val Xaa Pro Gly
    210             215                 220

Pro Gly Xaa Phe Leu Phe Met Gly Trp Ser Arg Phe Gly Glu Ala Xaa
225             230                 235                 240

Leu Gly Cys Ala Pro Arg Phe Gln Glu Phe Xaa Arg Xaa Tyr Xaa Ala
                245             250                 255

Ala Xaa Xaa Xaa His Leu Xaa Pro Cys Glu Xaa Ala Leu Xaa
            260             265                 270
```